United States Patent
Green et al.

(10) Patent No.: US 7,566,772 B2
(45) Date of Patent: Jul. 28, 2009

(54) ANTIBODIES AGAINST INTERLEUKIN-1β

(75) Inventors: Larry Green, San Francisco, CA (US); Raffaella Faggioni, Pleasanton, CA (US); Orit Foord, Foster City, CA (US); Scott L. Klakamp, Fremont, CA (US); Giorgio Senaldi, Dublin, CA (US); Amy K. Schneider, Dublin, CA (US)

(73) Assignee: Amgen Fremont Inc., Fremont, CA (US)

( * ) Notice: Subject to any disclaimer, the term of this patent is extended or adjusted under 35 U.S.C. 154(b) by 129 days.

(21) Appl. No.: 11/335,907

(22) Filed: Jan. 19, 2006

(65) Prior Publication Data

US 2007/0065439 A1 Mar. 22, 2007

Related U.S. Application Data

(60) Provisional application No. 60/647,643, filed on Jan. 26, 2005, provisional application No. 60/753,800, filed on Dec. 22, 2005.

(51) Int. Cl.
*C07K 16/24* (2006.01)

(52) U.S. Cl. .................. 530/388.15; 530/867; 530/351; 424/142.1; 424/801; 435/69.1; 435/320.1; 435/325

(58) Field of Classification Search ........................ None
See application file for complete search history.

(56) References Cited

U.S. PATENT DOCUMENTS

| | | | |
|---|---|---|---|
| 4,935,343 A | 6/1990 | Allison et al. | |
| 5,217,714 A | 6/1993 | Imura et al. | |
| 5,348,858 A | 9/1994 | Uetsuki et al. | |
| 5,484,887 A | 1/1996 | Kronheim et al. | |
| 5,681,933 A | 10/1997 | Auron et al. | |
| 5,686,246 A | 11/1997 | Kornman et al. | |
| 5,686,576 A | 11/1997 | Avraham et al. | |
| 5,789,188 A | 8/1998 | Rothstein et al. | |
| 6,528,051 B2 | 3/2003 | Tamarkin et al. | |
| 6,822,072 B1 * | 11/2004 | Edwards et al. | 530/300 |
| 2001/0034032 A1 | 10/2001 | diGiovine et al. | |
| 2002/0004061 A1 | 1/2002 | Panayotatos | |
| 2002/0182612 A1 | 12/2002 | Duff et al. | |
| 2003/0026806 A1 | 2/2003 | Witte et al. | |
| 2003/0124617 A1 | 7/2003 | Gram et al. | |
| 2004/0063913 A1 | 4/2004 | Gram et al. | |

FOREIGN PATENT DOCUMENTS

| | | |
|---|---|---|
| EP | 0267611 B1 | 5/1993 |
| EP | 0364778 B1 | 3/1996 |
| EP | 0374510 B1 | 1/1997 |
| EP | 0761688 A2 | 3/1997 |
| EP | 0541920 B1 | 4/2002 |
| WO | WO 88/09508 | 12/1988 |
| WO | WO 90/06371 | 6/1990 |
| WO | WO 92/10210 | 6/1992 |
| WO | WO 95/01997 | 1/1995 |
| WO | WO 01/53353 A | 7/2001 |
| WO | WO 02/02773 | 1/2002 |
| WO | WO 02/16436 A | 2/2002 |
| WO | WO 03/010282 A | 2/2003 |
| WO | WO 03/010282 A2 | 2/2003 |
| WO | WO 2004/067568 A | 8/2004 |
| WO | WO 2004/072116 A | 8/2004 |

OTHER PUBLICATIONS

MacCallum et al. Antibody-antigen Interactions: Contact Analysis and Binding Site Topography. J. Mol. Biol., 1996, 262:732-745.*
Padlan et al. Structure of an antibody-antigen complex: Crystal structure of the HyHEL-10 Fab-lysozyme complex. Proc. Natl. Acad. Sci. USA, 1989, 86 : 5938-5942.*
Sequence alignment between SEQ ID No. 76 of the present application and SEQ ID No. 972 of US6,822,072.*
Boder et al., "Directed Evolution of Antibody Fragments with Monovalent Femtomolar Antigen-Binding Affinity", *Proc Natl Acad Scienc. USA* (2000) 97(20): 10701-10705.
Jackson et al., "In Vitro Antibody Maturation Improvement of a High Affinity, Neutralizing Antibody Against IL-1β", *J Immunol.* (1995) 154(7): 3310-3319.

* cited by examiner

*Primary Examiner*—Dong Jiang
(74) *Attorney, Agent, or Firm*—Mary K. Hehman

(57) ABSTRACT

Antibodies directed to the antigen IL-1β and uses of such antibodies are described. In particular, fully human monoclonal antibodies directed to the antigen IL-1β. Nucleotide sequences encoding, and amino acid sequences comprising, heavy and light chain immunoglobulin molecules, particularly sequences corresponding to contiguous heavy and light chain sequences spanning the framework regions and/or complementarity determining regions (CDR's), specifically from FR1 through FR4 or CDR1 through CDR3. Hybridomas or other cell lines expressing such immunoglobulin molecules and monoclonal antibodies.

19 Claims, 11 Drawing Sheets

Blocking R4 on IL-1β neutralizes binding to IL-1R type I

*FIG. 6*

ANTIBODIES AGAINST INTERLEUKIN-1β

This application claims benefit to U.S. Provisional Application Ser. No. 60/647,643, filed Jan. 26, 2005, and U.S. Provisional Application Ser. No. 60/753,800, filed Dec. 22, 2005, which are incorporated herein by reference.

FIELD

The invention relates to targeted binding agents, such as monoclonal antibodies and fragments thereof, with binding affinity for interleukin-1β (IL-1β) and uses of such antibodies. More specifically, the invention relates to fully human monoclonal antibodies directed to IL-1β and uses of these antibodies.

BACKGROUND

The normal immune system is under a balance in which proinflammatory and anti-inflammatory cells and molecules are carefully regulated to promote normal host immune defense without the destruction of host's tissues. Once this careful regulatory balance is disturbed, nonspecific stimulation and activation can lead to increased amounts of potent destructive immunological and inflammatory molecules being produced and released. Thus, excess production of proinflammatory cytokines or production of cytokines in the wrong biological context, are associated with morbidity and mortality in a wide range of diseases.

Cytokines are pluripotent polypeptides that act by binding to specific cellular receptors. Their secretion is important in determining the duration and intensity of an immune response. Cytokines have pleiotropic effects and mediate a number of symptoms associated with inflammation.

IL-1β is involved in a wide variety of biological pathways, and is a potent molecule, able to induce its effects by triggering as few as one or two receptors per cell. As a signaling agent, IL-1β is effective at very low concentrations, even in the femtomolar range. IL-1β was first noted for inducing fever, augmenting lymphocyte responses, and stimulating the acute-phase response. IL-1β has a known role in inducint an inflammatory reaction in response to infection.

SUMMARY

Embodiments of the invention relate to targeted binding agents that specifically bind to interleukin-1β (IL-1β) and neutralize IL-1β activity. In one embodiment of the invention, the targeted binding agent is a fully human antibody, or binding fragment thereof, that neutralizes interleukin-1β (IL-1β) activity. In one aspect, the fully human antibody or binding fragment neutralizes interleukin-1β (IL-1β) and binds to IL-1β with a $K_D$ of 400 pM, 100 pM, 10 pM, 1 pM, 500 fM, 300 fM, 200 fM, 50 fm or less. In some embodiments, the antibody has an IgG2 isotype, while in other embodiments the antibody is an IgG4 isotype. In some embodiments, the antibody is isotype switched from one isotype to another. In some embodiments, the antibody is in association with a pharmaceutically acceptable carrier or diluent.

In some embodiments, the antibody binds to a particular epitope of IL-1β, such as amino acids 1-34 of the N terminal domain. In other embodiments, the targeted binding agent binds to IL-1β in part via an arginine at the fourth amino acid of the mature IL-1β polypeptide. In some embodiments, the targeted binding agent binds to IL-1β in part via an arginine at the eleventh amino acid of the mature IL-1β polypeptide.

In some embodiments, the targeted binding agent is an antibody which comprises a heavy chain amino acid sequence having a complementarity determining region (CDR) with the same sequence as a CDR of SEQ ID NO: 74. In some embodiments, the antibody further comprises a light chain amino acid sequence having a CDR with the same sequence as a CDR of SEQ ID NO: 76. In some embodiments, the antibody comprises a light chain polypeptide having the sequence of SEQ ID NO: 76. In some embodiments, the antibody comprises a heavy chain polypeptide having the sequence of SEQ ID NO: 74. In some embodiments, the antibody is antibody 5.5.1. In other embodiments, the antibody is antibody 9.5.2.

Another embodiment of the invention is an antibody that competes for binding with any of the antibodies described above.

Still another embodiment is an isolated polynucleotide that encodes a heavy chain variable domain of an antibody, wherein the heavy chain variable domain comprises a complementarity determining region from the amino acid sequence of SEQ ID NO: 74. Another embodiment is an isolated polynucleotide that encodes a light chain variable domain of an antibody, wherein the light chain variable domain comprises a complementarity determining region from the amino acid sequence of SEQ ID NO: 76. In some embodiments, the invention includes a vector comprising a polynucleotide described above. In other embodiments, the invention includes a host cell comprising one of the above described vectors.

Another aspect of the invention is a method of effectively treating an animal suffering from an IL-1β related disorder, the method comprising: selecting an animal in need of treatment for an IL-1β related disorder; and administering to the animal a therapeutically effective dose of a targeted binding agent that neutralizes the biological activity of IL-1β. In some embodiments, the treatable IL-1β related disorder is selected from the group consisting of inflammatory disorders, cachexia and chronic fatigue syndrome, osteoporosis, atherosclerosis, pain related disorders, congestive heart failure, leukemias, multiple myelomas, tumor growth and metastatic spreading. In some embodiments of the above described method, the targeted binding agent comprises a neutralizing fully human monoclonal antibody that binds to amino acids 1-34 of the N-terminal domain of IL-1β.

Yet another embodiment of the invention is a method of effectively treating an animal suffering from an IL-1β related disorder. The method includes selecting an animal in need of treatment for an IL-1β related disorder, and administering to the animal a therapeutically effective dose of a neutralizing fully human monoclonal antibody that binds to interleukin-1β (IL-1β) with a $K_D$ of 200 fin or less. In some embodiments, the treatable IL-1β related disorder is an inflammatory disorder such as cachexia and chronic fatigue syndrome, osteoporosis, atherosclerosis, pain related disorders, congestive heart failure, leukemia, multiple myeloma, tumor growth or metastatic spreading.

Still another embodiment of the invention is a polynucleotide that encodes a polypeptide from at least one chain of a fully human monoclonal antibody that binds to interleukin-1β (IL-1β) with a $K_D$ of 200 fM or less. In some embodiments, the polynucleotide encodes the heavy chain of the monoclonal antibody, and the nucleotide sequence has the sequence of SEQ ID NO: 73. In some embodiments, the polynucleotide encodes the light chain of the monoclonal antibody, and the nucleotide sequence has the sequence of SEQ ID NO: 75. In some embodiment, the invention includes a vector comprising a polynucleotide described above. In other embodiments, the invention includes a host cell comprising one of the above described vectors.

Yet another embodiment includes methods for treating diseases or conditions associated with the expression of IL-1β in a patient, by administering to the patient an effective amount of an anti-IL-1β antibody in combination with additional antibodies or chemotherapeutic drug or radiation therapy. For example, a monoclonal, oligoclonal or polyclonal mixture of IL-1β antibodies that block inflammation can be administered in combination with a drug shown to inhibit inflammation directly. The method can be performed in vivo and the patient is preferably a human patient. In a preferred embodiment, the method concerns the treatment of inflammatory disorders such as cachexia and chronic fatigue syndrome, osteoporosis, atherosclerosis.

BRIEF DESCRIPTION OF THE DRAWINGS

Figure 6:
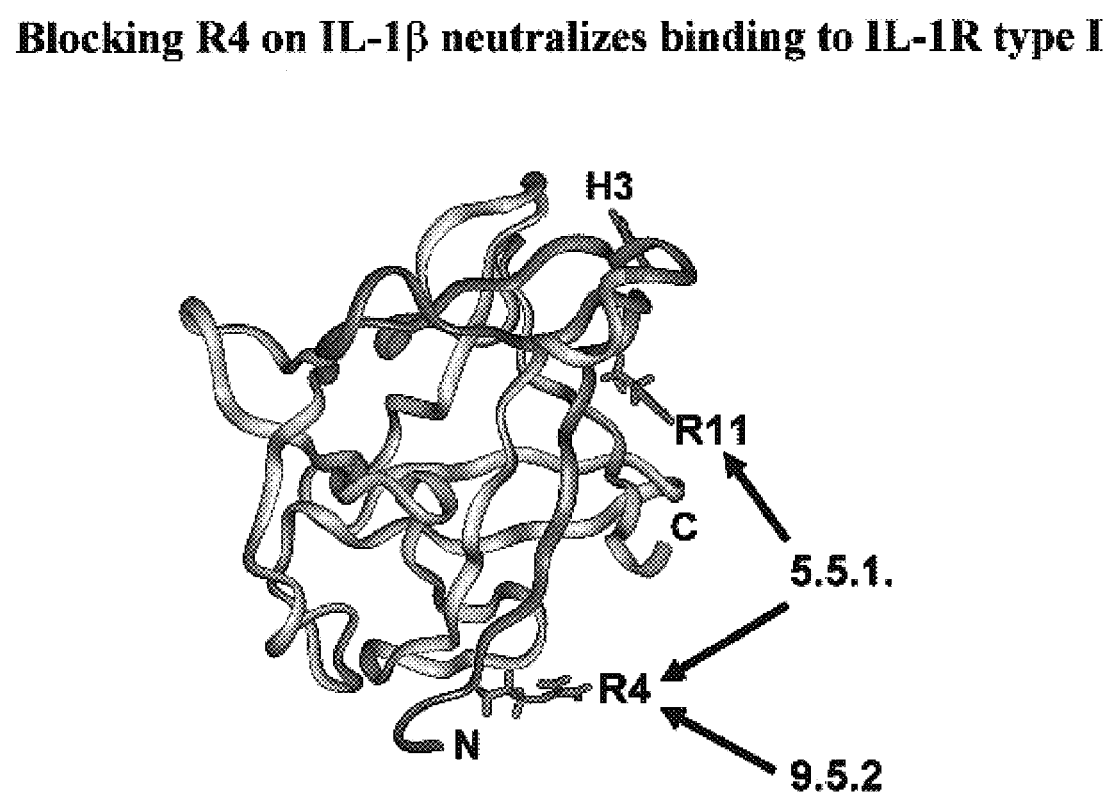

FIG. 6 is a structural model depicting the areas of antibody 9.5.2 and antibody 5.5.1 interaction with IL-1 beta.

DETAILED DESCRIPTION

Figure 1A:
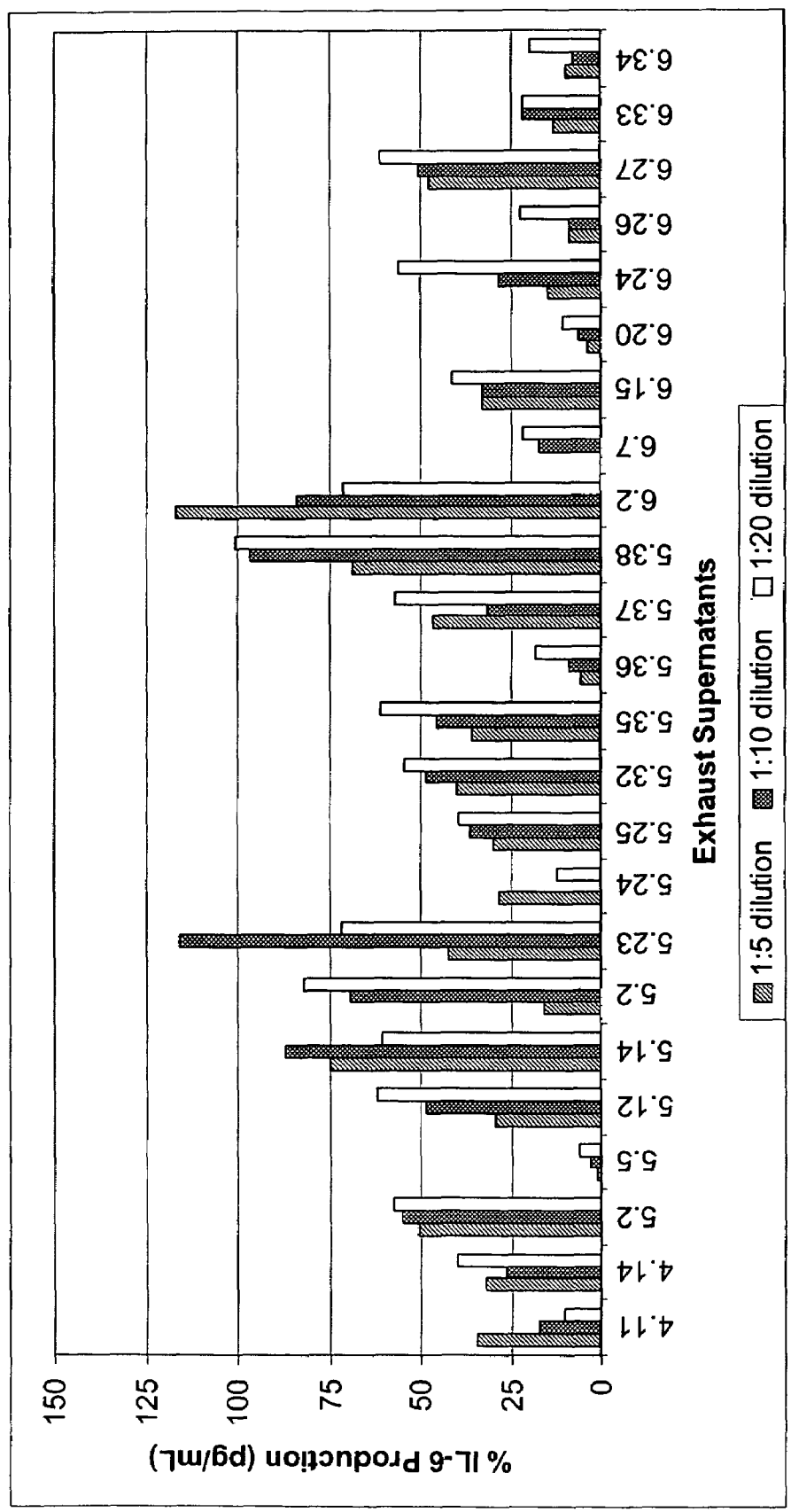
FIG. 1A is a bar graph displaying the percent of IL-6 production induced by IL-1β (4 pM) in MRC-5 cells in the presence of various amounts of the given antibodies.
Figure 1B:
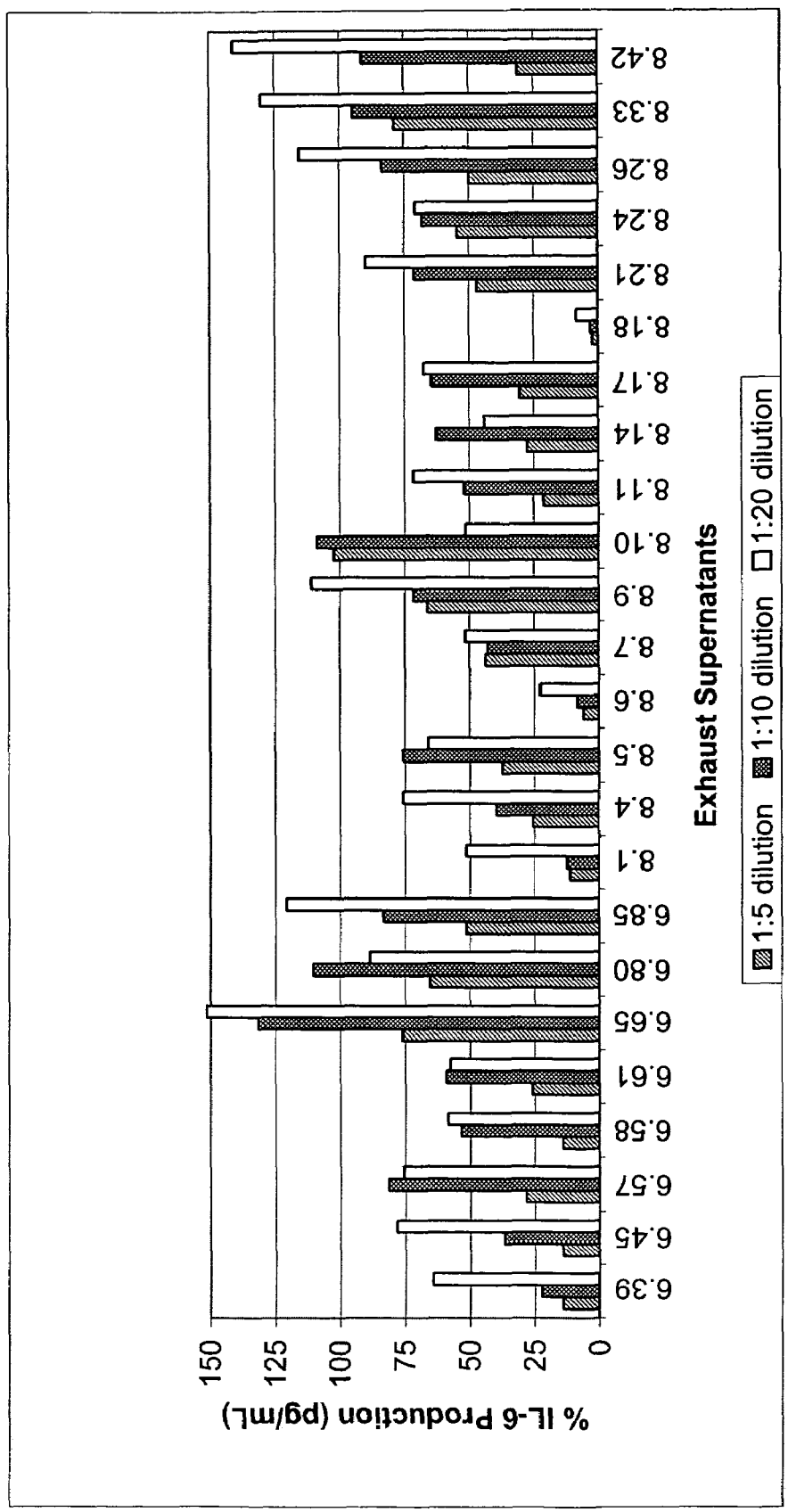
FIG. 1B is a bar graph displaying the percent of IL-6 production induced by IL-1β (4 pM) in MRC-5 cells in the presence of various amounts of the given antibodies.
Figure 1C:
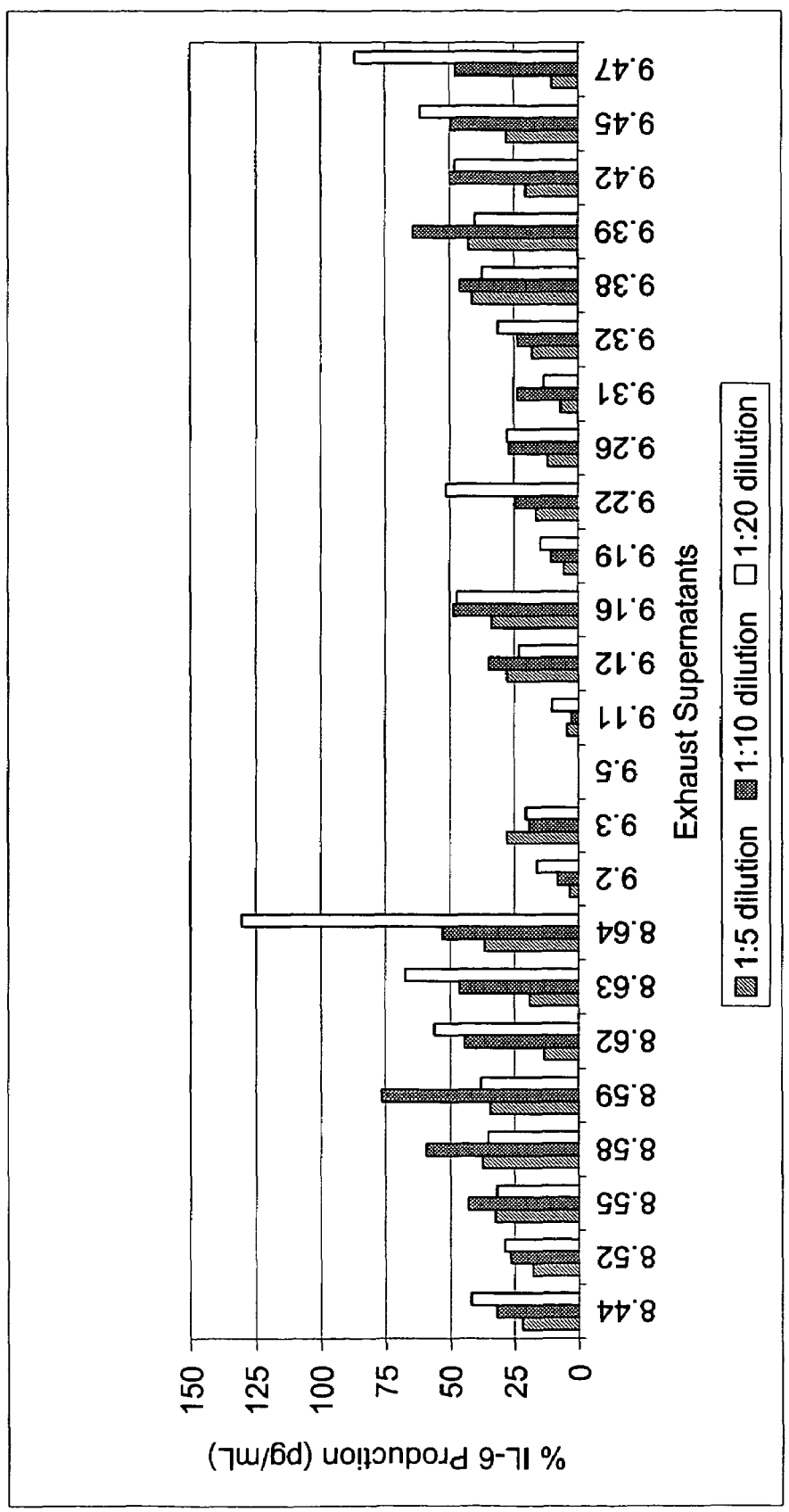
FIG. 1C is a bar graph displaying the percent of IL-6 production induced by IL-1β (4 pM) in MRC-5 cells in the presence of various amounts of the given antibodies.
Figure 1D:
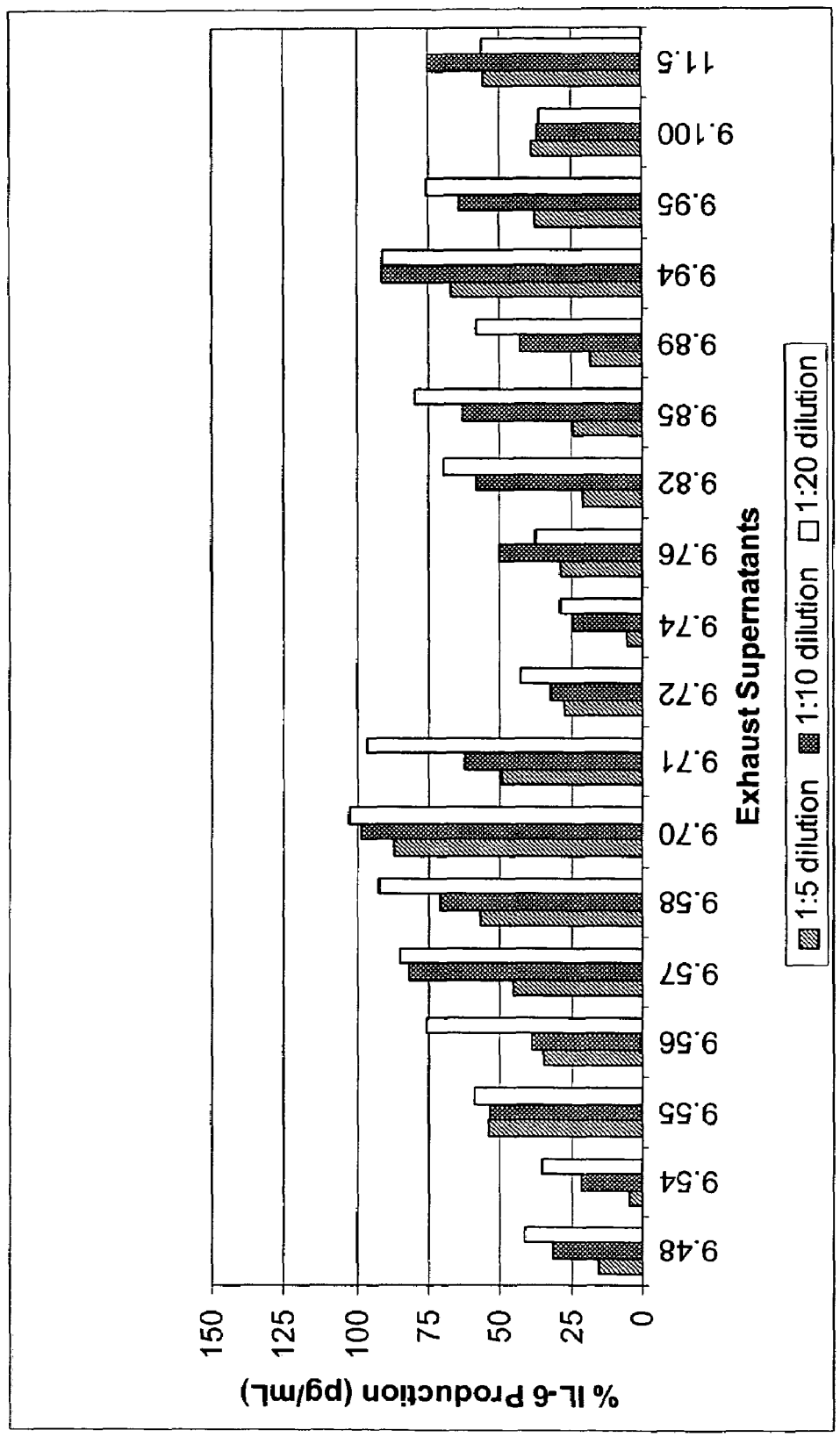
FIG. 1D is a bar graph displaying the percent of IL-6 production induced by IL-1β (4 pM) in MRC-5 cells in the presence of various amounts of the given antibodies.

Interleukin-1β (IL-1β) is a pro-inflammatory cytokine that plays a major role in a wide range of diseases, including inflammatory diseases. Disclosed are targeted binding agents, such as monoclonal antibodies, that bind to and neutralize the activity of IL-1β. In one embodiment, the targeted binding agent is a fully human monoclonal antibody that specifically binds to IL-1β. In some embodiments the antibodies bind to IL-1β with a particularly high affinity. In some embodiments the antibodies are highly potent, either in vitro, in vivo, or under both situations. In some embodiments, treatment with such antibodies can result in inhibition of IL-6 production and/or IL-8 production in vitro, in vivo, or under both situations.

In some embodiments, the disclosed antibodies are more potent, more selective, have a longer half-life, or some combination thereof, than recombinant IL-1 receptor antagonists (IL-1Ra) or anakinra (e.g., KINERET™). This can be advantageous as the therapeutic efficacy of anakinra may be limited by its biological and pharmacokinetic properties. For instance, anakinra prevents the binding of IL-1 to its receptor via a mechanism of receptor antagonism. In order for anakinra to be effective, it has to compete with IL-1 at the level of all receptors, which are ubiquitous and numerous. Moreover, anakinra has a short circulating half-life (4-6 hours) in humans.

As described in detail below, a panel of fully human IL-1β monoclonal antibodies (mAbs) was generated and examined. One example of such an antibody is termed herein "9.5.2". Antibody 9.5.2 is a high-affinity ($K_D$=204 fM for IgG2 and 181 fM for IgG4) IgG2λ mAb that binds to N-terminal residues 1-34 of the IL-1β molecule. Antibody 9.5.2 potently neutralizes IL-1β dependent effects in vitro and in vivo. 9.5.2 mAb inhibits IL-1β-induced IL-6 production by MRC-5 cells and IL-8 production in whole blood. In mice, 9.5.2 mAb inhibited IL-1β-induced IL-6 and MPO production. The 9.5.2 mAb had in vitro and in vivo potencies superior to anakinra. This established that blockade of IL-1β with a mAb is a valid neutralizing approach that can be useful in the treatment of inflammatory diseases.

A further embodiment of the invention is an antibody that cross-competes for binding to IL-1β with the fully human antibodies of the invention, preferably an antibody comprising a heavy chain amino acid sequence having one of the CDR sequences shown in Table 25 and a light chain amino acid sequence having one of the CDR sequences shown in Table 26. A further embodiment of the invention is an antibody that binds to the same epitope on IL-1β as a fully human antibodies of the invention, preferably an antibody comprising a heavy chain amino acid sequence having one of the CDR sequences shown in Table 25 and a light chain amino acid sequence having one of the CDR sequences shown in Table 26.

Further embodiments, features, and the like regarding IL-1β antibodies are provided in detail below.

Sequence Listing

Embodiments of the invention include the specific IL-1β antibodies listed below in Table 1. This table reports the identification number ("mAb ID No.") of each IL-1β antibody, along with the SEQ ID number of the corresponding heavy chain and light chain for the nucleic acid and amino acid sequences. The mAb ID No. is used to identify the various antibodies. When mAb ID Nos. begin with the same first two sets of numbers (e.g., 9.5.2 and 9.5) this denotes that the antibodies are clones and are thus identical. The complete sequences can be found in the sequence listing and a comparison of the sequences can be found in Table 25 and Table 26.

TABLE 1

| mAb ID No.: | Sequence | SEQ ID NO: |
|---|---|---|
| 4.20.1 | Nucleotide sequence encoding the variable region of the heavy chain | 1 |
| | Amino acid sequence encoding the variable region of the heavy chain | 2 |
| | Nucleotide sequence encoding the variable region of the light chain | 3 |
| | Amino acid sequence encoding the variable region of the light chain | 4 |

TABLE 1-continued

| mAb ID No.: | Sequence | SEQ ID NO: |
|---|---|---|
| 5.36.1 | Nucleotide sequence encoding the variable region of the heavy chain | 5 |
|  | Amino acid sequence encoding the variable region of the heavy chain | 6 |
|  | Nucleotide sequence encoding the variable region of the light chain | 7 |
|  | Amino acid sequence encoding the variable region of the light chain | 8 |
| 5.5.1 | Nucleotide sequence encoding the variable region of the heavy chain | 9 |
|  | Amino acid sequence encoding the variable region of the heavy chain | 10 |
|  | Nucleotide sequence encoding the variable region of the light chain | 11 |
|  | Amino acid sequence encoding the variable region of the light chain | 12 |
| 6.20.1 | Nucleotide sequence encoding the variable region of the heavy chain | 13 |
|  | Amino acid sequence encoding the variable region of the heavy chain | 14 |
|  | Nucleotide sequence encoding the variable region of the light chain | 15 |
|  | Amino acid sequence encoding the variable region of the light chain | 16 |
| 6.26.1 | Nucleotide sequence encoding the variable region of the heavy chain | 17 |
|  | Amino acid sequence encoding the variable region of the heavy chain | 18 |
|  | Nucleotide sequence encoding the variable region of the light chain | 19 |
|  | Amino acid sequence encoding the variable region of the light chain | 20 |
| 6.33.1 | Nucleotide sequence encoding the variable region of the heavy chain | 21 |
|  | Amino acid sequence encoding the variable region of the heavy chain | 22 |
|  | Nucleotide sequence encoding the variable region of the light chain | 23 |
|  | Amino acid sequence encoding the variable region of the light chain | 24 |
| 6.34.1 | Nucleotide sequence encoding the variable region of the heavy chain | 25 |
|  | Amino acid sequence encoding the variable region of the heavy chain | 26 |
|  | Nucleotide sequence encoding the variable region of the light chain | 27 |
|  | Amino acid sequence encoding the variable region of the light chain | 28 |
| 6.7.1 | Nucleotide sequence encoding the variable region of the heavy chain | 29 |
|  | Amino acid sequence encoding the variable region of the heavy chain | 30 |
|  | Nucleotide sequence encoding the variable region of the light chain | 31 |
|  | Amino acid sequence encoding the variable region of the light chain | 32 |
| 8.18.1 | Nucleotide sequence encoding the variable region of the heavy chain | 33 |
|  | Amino acid sequence encoding the variable region of the heavy chain | 34 |
|  | Nucleotide sequence encoding the variable region of the light chain | 35 |
|  | Amino acid sequence encoding the variable region of the light chain | 36 |
| 8.50.1 | Nucleotide sequence encoding the variable region of the heavy chain | 37 |
|  | Amino acid sequence encoding the variable region of the heavy chain | 38 |
|  | Nucleotide sequence encoding the variable region of the light chain | 39 |
|  | Amino acid sequence encoding the variable region of the light chain | 40 |
| 8.59.1 | Nucleotide sequence encoding the variable region of the heavy chain | 41 |
|  | Amino acid sequence encoding the variable region of the heavy chain | 42 |
|  | Nucleotide sequence encoding the variable region of the light chain | 43 |
|  | Amino acid sequence encoding the variable region of the light chain | 44 |
| 8.6.1 | Nucleotide sequence encoding the variable region of the heavy chain | 45 |
|  | Amino acid sequence encoding the variable region of the heavy chain | 46 |
|  | Nucleotide sequence encoding the variable region of the light chain | 47 |
|  | Amino acid sequence encoding the variable region of the light chain | 48 |
| 9.11.1 | Nucleotide sequence encoding the variable region of the heavy chain | 49 |
|  | Amino acid sequence encoding the variable region of the heavy chain | 50 |
|  | Nucleotide sequence encoding the variable region of the light chain | 51 |
|  | Amino acid sequence encoding the variable region of the light chain | 52 |
| 9.19.1 | Nucleotide sequence encoding the variable region of the heavy chain | 53 |
|  | Amino acid sequence encoding the variable region of the heavy chain | 54 |
|  | Nucleotide sequence encoding the variable region of the light chain | 55 |
|  | Amino acid sequence encoding the variable region of the light chain | 56 |
| 9.26.1 | Nucleotide sequence encoding the variable region of the heavy chain | 57 |
|  | Amino acid sequence encoding the variable region of the heavy chain | 58 |
|  | Nucleotide sequence encoding the variable region of the light chain | 59 |
|  | Amino acid sequence encoding the variable region of the light chain | 60 |
| 9.2.1 | Nucleotide sequence encoding the variable region of the heavy chain | 61 |
|  | Amino acid sequence encoding the variable region of the heavy chain | 62 |
|  | Nucleotide sequence encoding the variable region of the light chain | 63 |
|  | Amino acid sequence encoding the variable region of the light chain | 64 |
| 9.31.1 | Nucleotide sequence encoding the variable region of the heavy chain | 65 |
|  | Amino acid sequence encoding the variable region of the heavy chain | 66 |
|  | Nucleotide sequence encoding the variable region of the light chain | 67 |
|  | Amino acid sequence encoding the variable region of the light chain | 68 |
| 9.54.1 | Nucleotide sequence encoding the variable region of the heavy chain | 69 |
|  | Amino acid sequence encoding the variable region of the heavy chain | 70 |
|  | Nucleotide sequence encoding the variable region of the light chain | 71 |
|  | Amino acid sequence encoding the variable region of the light chain | 72 |
| 9.5.2 | Nucleotide sequence encoding the variable region of the heavy chain | 73 |
|  | Amino acid sequence encoding the variable region of the heavy chain | 74 |
|  | Nucleotide sequence encoding the variable region of the light chain | 75 |
|  | Amino acid sequence encoding the variable region of the light chain | 76 |

Definitions

Unless otherwise defined, scientific and technical terms used herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art.

Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. *Molecular Cloning: A Laboratory Manual* (3rd ed., Cold Spring Harbor Laboratory Press, Cold Spring Harbor, N.Y. (2001)), which is incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

The terms "IL-1B," "IL-1b," "IL-1β," "IL-1Beta," "IL-1β," and similar such terms refer to the molecule interleukin-1β. In some embodiments, included in this definition are precursors of IL-1β, such as pro-IL-1β. An example of a mature form of IL-1B is shown in SEQ ID NO: 77. An "IL-1 beta antibody" is an antibody that binds to IL-1 beta. This can also be referred to as an anti-IL-1 beta, or, somewhat redundantly, an anti-IL-1 beta antibody. These antibodies can also be referred to with their "mAb ID No," shown above in Table 1. Thus, "mAb 9.5.2," "9.5.2," or "9.5.2 mAb," where appropriate, refer to the antibody. Antibodies can be named with either numerals separated by periods or numerals separated by dashes, nothing is implied by this difference.

The term "neutralizing" when referring to an antibody relates to the ability of an antibody to eliminate, or significantly reduce, the activity of a target antigen. Accordingly, a "neutralizing" IL-1β antibody is capable of eliminating or significantly reducing the activity of IL-1β. A neutralizing IL-1β antibody may, for example, act by blocking the binding of IL-1β to a type I IL-1 receptor ("IL-1R"). By blocking this binding, the IL-1β mediated signal transduction is significantly, or completely, eliminated. Ideally, a neutralizing antibody against IL-1β inhibits IL-1β related disorders. In another embodiment, the neutralizing antibody prevents the IL-1β molecule from binding to the type II IL-1 receptor. The type II receptor is also known as a decoy receptor. Thus, a neutralizing antibody that prevents IL-1β from binding to the type II receptor, but still allows IL-1β to bind to the type I receptor would result in an effective increase in IL-1β activity. Unless denoted otherwise, the IL-1 receptor shall refer to the type I receptor. As will be appreciated by one of skill in the art, the antibody can be neutralizing for any and all functions of the protein. Thus, for example, an IL-1β antibody may alter the production of IL-6, IL-8, or both. Antibodies can have differing levels of potency for different assays. Contemplated potencies include any effective potency, for example, $IC_{50}$s of less than 14 nM to 1 nM, 1 nM to 500 pM, 500 pM to 1 pM for IL-6 inhibition; less than 2.3 nM to 100 pM, 100 pM to 70 pM, or 70 to 4 pM for IL-8 inhibition; and less than 51-8,8-5, or 5 pmoles/mouse for in vivo IL-6 production.

The term "isolated polynucleotide" as used herein shall mean a polynucleotide that has been isolated from its naturally occurring environment. Such polynucleotides may be genomic, cDNA, or synthetic. Isolated polynucleotides preferably are not associated with all or a portion of the polynucleotides they associate with in nature. The isolated polynucleotides may be operably linked to another polynucleotide to which it is not linked in nature. In addition, isolated polynucleotides preferably do not occur in nature as part of a larger sequence.

The term "isolated protein" referred to herein means a protein that has been isolated from its naturally occurring environment. Such proteins may be derived from genomic DNA, cDNA, recombinant DNA, recombinant RNA, or synthetic origin or some combination thereof, which by virtue of its origin, or source of derivation, the "isolated protein" (1) is not associated with proteins found in nature, (2) is free of other proteins from the same source, e.g. free of murine proteins, (3) is expressed by a cell from a different species, or (4) does not occur in nature.

The term "polypeptide" is used herein as a generic term to refer to native protein, fragments, or analogs of a polypeptide sequence. Hence, native protein, fragments, and analogs are species of the polypeptide genus. Preferred polypeptides in accordance with the invention comprise the human heavy chain immunoglobulin molecules and the human kappa light chain immunoglobulin molecules, the human heavy chain immunoglobulin molecules and the human lambda light chain immunoglobulin molecules, as well as antibody molecules formed by combinations comprising the heavy chain immunoglobulin molecules with light chain immunoglobulin molecules, such as the kappa or lambda light chain immunoglobulin molecules, and vice versa, as well as fragments and analogs thereof. Preferred polypeptides in accordance with the invention may also comprise solely the human heavy chain immunoglobulin molecules or fragments thereof.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to positions of components so described that are in a relationship permitting them to function in their intended manner. For example, a control sequence "operably linked" to a coding sequence is connected in such a way that expression of the coding sequence is achieved under conditions compatible with the control sequences.

The term "control sequence" as used herein refers to polynucleotide sequences that are necessary either to effect or to affect the expression and processing of coding sequences to which they are connected. The nature of such control sequences differs depending upon the host organism; in prokaryotes, such control sequences generally include promoter, ribosomal binding site, and transcription termination sequence; in eukaryotes, generally, such control sequences may include promoters, introns and transcription termination sequence. The term "control sequences" is intended to include, at a minimum, all components whose presence is essential for expression and processing, and can also include additional components whose presence is advantageous, for example, leader sequences and fusion partner sequences.

The term "polynucleotide" as referred to herein means a polymeric form of nucleotides of at least 10 bases in length, either ribonucleotides or deoxynucleotides or a modified form of either type of nucleotide. The term includes single- and double-stranded forms of DNA.

The term "oligonucleotide" referred to herein includes naturally occurring, and modified nucleotides linked together by naturally occurring, and non-naturally occurring linkages. Oligonucleotides are a polynucleotide subset generally comprising a length of 200 bases or fewer. Preferably, oligonucleotides are 10 to 60 bases in length and most preferably 12, 13, 14, 15, 16, 17, 18, 19, or 20 to 40 bases in length. Oligonucleotides are usually single stranded, e.g. for probes; although oligonucleotides may be double stranded, e.g. for use in the construction of a gene mutant. Oligonucleotides can be either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phosphoraniladate, phosphoroamidate, and the like. See e.g., LaPlanche et al. *Nucl. Acids Res.* 14:9081 (1986); Stec et al. *J. Am. Chem. Soc.* 106:6077 (1984); Stein et al. *Nucl. Acids Res.* 16:3209 (1988); Zon et al. *Anti-Cancer Drug Design* 6:539 (1991); Zon et al *Oligonucleotides and Analogues: A Practical Approach*, pp. 87-108 (F. Eckstein, Ed., Oxford University Press, Oxford England (1991)); Stec et al. U.S. Pat. No. 5,151,510; Uhlmann and Peyman *Chemical Reviews* 90:543 (1990), the disclosures of which are hereby incorporated by reference. An oligonucleotide can include a label for detection, if desired.

The term "selectively hybridize" referred to herein means to detectably and specifically bind. Polynucleotides, oligonucleotides and fragments thereof selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, or antibody fragments and a nucleic acid sequence of interest will be at least 80%, and more typically with preferably increasing homologies of at least 85%, 90%, 95%, 99%, and 100%.

Two amino acid sequences are "homologous" if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least about 30 amino acids in length) are homologous, as this term is used herein, if they have an alignment score of, or more than, 5 (in standard deviation units) using the program ALIGN with the mutation data matrix and a gap penalty of 6 or greater. See Dayhoff, M. O., in *Atlas of Protein Sequence and Structure*, pp. 101-110 (Volume 5, National Biomedical Research Foundation (1972)) and Supplement 2 to this volume, pp. 1-10. The two sequences or parts thereof are more preferably homologous if their amino acids are greater than or equal to 50% identical when optimally aligned using the ALIGN program.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence.

In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotide or amino acid sequences: "reference sequence", "comparison window", "sequence identity", "percentage of sequence identity", and "substantial identity". A "reference sequence" is a defined sequence used as a basis for a sequence comparison. A reference sequence may be a subset of a larger sequence, for example, as a segment of a full-length cDNA or gene sequence given in a sequence listing or may comprise a complete cDNA or gene sequence. Generally, a reference sequence is at least 18 nucleotides or 6 amino acids in length, frequently at least 24 nucleotides or 8 amino acids in length, and often at least 48 nucleotides or 16 amino acids in length. Since two polynucleotides or amino acid sequences may each (1) comprise a sequence (i.e., a portion of the complete polynucleotide or amino acid sequence) that is similar between the two molecules, and (2) may further comprise a sequence that is divergent between the two polynucleotides or amino acid sequences, sequence comparisons between two (or more) molecules are typically performed by comparing sequences of the two molecules over a "comparison window" to identify and compare local regions of sequence similarity. A "comparison window", as used herein, refers to a conceptual segment of at least about 18 contiguous nucleotide positions or about 6 amino acids wherein the polynucleotide sequence or amino acid sequence is compared to a reference sequence of at least 18 contiguous nucleotides or 6 amino acid sequences and wherein the portion of the polynucleotide sequence in the comparison window may include additions, deletions, substitutions, and the like (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman *Adv. Appl. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci.* (*U.S.A.*) 85:2444 (1988), by computerized implementations of these algorithms (GAP, BESTFIT, FASTA, and TFASTA in the Wisconsin Genetics Software Package Release 7.0, (Genetics Computer Group, 575 Science Dr., Madison, Wis.), GENEWORKS™, or MACVECTOR® software packages), or by inspection, and the best alignment (i.e., resulting in the highest percentage of homology over the comparison window) generated by the various methods is selected.

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U, or I) or amino acid residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more preferably at least 99 percent sequence identity, as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As used herein, the twenty conventional amino acids and their abbreviations follow conventional usage. See *Immunology—A Synthesis* ($2^{nd}$ Edition, E. S. Golub and D. R. Gren, Eds., Sinauer Associates, Sunderland, Mass. (1991)), which is incorporated herein by reference. Stereoisomers (e.g., D-amino acids) of the twenty conventional amino acids, unnatural amino acids such as α-,α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, σ-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention. Additionally, the short hand notation for amino acids and amino acid substitutions is also used. As such, "amino acid, amino acid position, amino acid" represents the wild-type amino acid, the position of that amino acid, and the residue that the amino acid has been replaced with. Thus, A472Y means that the original alanine at position 472 has been replaced with a tryptophan.

Similarly, unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity. Preferably, residue positions that are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, glutamic-aspartic, and asparagine-glutamine.

As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99% sequence identity to the antibodies or immunoglobulin molecules described herein. In particular, conservative amino acid replacements are contemplated. Conservative replacements are those that take place within a family of amino acids that have related side chains. Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine, which form an aliphatic-hydroxy family; asparagine and glutamine, which form an amide-containing family; alanine, valine, leucine and isoleucine, which form an aliphatic family; and phenylalanine, tryptophan, and tyrosine, which form an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding function or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. *Science* 253:164 (1991). Thus, the foregoing examples demonstrate that those of skill in the art can recognize sequence motifs and structural conformations that may be used to define structural and functional domains in accordance with the antibodies described herein.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in *Proteins, Structures and Molecular Principles* (Creighton, Ed., W. H. Freeman and Company, New York (1984)); *Introduction to Protein Structure* (C. Branden and J. Tooze, eds., Garland Publishing, New York, N.Y. (1991)); and Thornton et at. *Nature* 354:105 (1991), which are each incorporated herein by reference.

The term "polypeptide fragment" as used herein refers to a polypeptide that has an amino-terminal and/or carboxy-terminal deletion, but where the remaining amino acid sequence is identical to the corresponding positions in the naturally-occurring sequence deduced, for example, from a full-length cDNA sequence. Fragments typically are at least 5, 6, 8 or 10 amino acids long, preferably at least 14 amino acids long, more preferably at least 20 amino acids long, usually at least 50 amino acids long, and even more preferably at least 70 amino acids long. The term "analog" as used herein refers to polypeptides which are comprised of a segment of at least 25 amino acids that has substantial identity to a portion of a deduced amino acid sequence and which has at least one of the following properties: (1) specific binding to a IL-1β, under suitable binding conditions, (2) ability to block appropriate IL-1β binding, or (3) ability to inhibit IL-1β activity. Typically, polypeptide analogs comprise a conservative amino acid substitution (or addition or deletion) with respect to the naturally-occurring sequence. Analogs typically are at least 20 amino acids long, preferably at least 50 amino acids long or longer, and can often be as long as a full-length naturally-occurring polypeptide.

Peptide analogs are commonly used in the pharmaceutical industry as non-peptide drugs with properties analogous to those of the template peptide. These types of non-peptide compound are termed "peptide mimetics" or "peptidomimetics". Fauchere, *J. Adv. Drug Res.* 15:29 (1986); Veber and Freidinger *TINS* p.392 (1985); and Evans et al. *J. Med. Chem.* 30:1229 (1987), which are incorporated herein by reference. Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: —$CH_2NH$—, —$CH_2S$—, —$CH_2$—$CH_2$—, —$CH=CH$— (cis and trans), —$COCH_2$—, —$CH(OH)CH_2$—, and —$CH_2SO$—, by methods well known in the art. Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch *Ann. Rev. Biochem.* 61:387 (1992), incorporated herein by reference); for example, by adding internal cysteine residues capable of forming intramolecular disulfide bridges which cyclize the peptide.

As used herein, the term "antibody" refers to a polypeptide or group of polypeptides which are comprised of at least one binding domain, where an antibody binding domain is formed from the folding of variable domains of an antibody molecule to form three-dimensional binding spaces with an internal surface shape and charge distribution complementary to the features of an antigenic determinant of an antigen. An antibody typically has a tetrameric form, comprising two identical pairs of polypeptide chains, each pair having one "light" and one "heavy" chain. The variable regions of each light/heavy chain pair form an antibody binding site.

As used herein, the term "unit dose" refers to an amount of a substance sufficient to achieve a desired result in a particular subject. Thus, unit doses can vary depending upon the particular substance in the unit dose, who will be taking the substance, and what the desired result will be.

As used herein, a "targeted binding agent" is an antibody, or binding fragment thereof, that preferentially binds to a target site. In one embodiment, the targeted binding agent is specific for only one target site. In other embodiments, the targeted binding agent is specific for more than one target site. In one embodiment, the targeted binding agent may be a monoclonal antibody and the target site may be an epitope.

"Binding fragments" of an antibody are produced by recombinant DNA techniques, or by enzymatic or chemical cleavage of intact antibodies. Binding fragments include Fab, Fab', F(ab')$_2$, Fv, and single-chain antibodies. An antibody other than a "bispecific" or "bifunctional" antibody is understood to have each of its binding sites identical. An antibody substantially inhibits adhesion of a receptor to a counter-receptor when an excess of antibody reduces the quantity of receptor bound to counterreceptor by at least about 20%, 40%, 60% or 80%, and more usually greater than about 85% (as measured in an in vitro competitive binding assay). A "complete" antibody refers to an antibody that has all of the parts that make up an antibody, as defined by the definition of "antibody," above. Of course, variants or insubstantial modifications of the antibody can result in antibodies that are smaller than the full antibody sequence.

The term "epitope" includes any protein determinant capable of specific binding to an immunoglobulin or T-cell receptor. Epitopic determinants usually consist of chemically active surface groupings of molecules such as amino acids or sugar side chains and can, but not always, have specific three-dimensional structural characteristics, as well as specific charge characteristics. An antibody is said to bind an antigen when the dissociation constant ($K_D$ or $K_d$) is less than or equal to 1 µM, 100 nM, 10 nM, 1 M, 100 pM, 10 pM, 1 pM, 100 nM, 10 nM, 1 nM, 500 fM, 100 fM, 10 fM, or less. Antibodies that compete for binding with the herein disclosed antibodies are also contemplated. Competition can be direct, for the entire epitope, or a fraction of the epitope, or competition can be indirect, where binding of the antibody prevents the binding of the herein disclosed antibodies.

The terms "selectively bind" or "specifically bind" are used herein to denote that the antibody will bind to one substance more strongly than it will bind to another substance. It is not meant to denote that the antibody will only bind to one substance. When binding only occurs between a single substance and the antibody, the antibody is said to "exclusively" bind to the substance.

The term "agent" is used herein to denote a chemical compound, a mixture of chemical compounds, a biological macromolecule, or an extract made from biological materials.

"Active" or "activity" in regard to an IL-1β polypeptide refers to a portion of an IL-1β polypeptide that has a biological or an immunological activity of a native IL-1β polypeptide. "Biological" when used herein refers to a biological function that results from the activity of the native IL-1β polypeptide. A preferred IL-1β biological activity includes, for example, IL-1β induced inflammatory disorders.

"Mammal" when used herein refers to any animal that is considered a mammal. Preferably, the mammal is human.

Digestion of antibodies with the enzyme, papain, results in two identical antigen-binding fragments, known also as "Fab" fragments, and a "Fc" fragment, having no antigen-binding activity but having the ability to crystallize. Digestion of antibodies with the enzyme, pepsin, results in the a F(ab')$_2$ fragment in which the two arms of the antibody molecule remain linked and comprise two-antigen binding sites. The F(ab')$_2$ fragment has the ability to crosslink antigen.

"Fv" when used herein refers to the minimum fragment of an antibody that retains both antigen-recognition and antigen-binding sites.

"Fab" when used herein refers to a fragment of an antibody that comprises the constant domain of the light chain and the CH1 domain of the heavy chain.

The term "mAb" refers to monoclonal antibody.

"Liposome" when used herein refers to a small vesicle that may be useful for delivery of drugs that may include the IL-1β polypeptide of the invention or antibodies to such an IL-1β polypeptide to a mammal.

"Label" or "labeled" as used herein refers to the addition of a detectable moiety to a polypeptide, for example, a radiolabel, fluorescent label, enzymatic label chemiluminescent labeled or a biotinyl group. Radioisotopes or radionuclides may include $^3$H, $^{14}$C, $^{15}$N, $^{35}$S, $^{90}$Y, $^{99}$Tc, $^{111}$In, $^{125}$I, $^{131}$I, fluorescent labels may include rhodamine, lanthanide phosphors or FITC and enzymatic labels may include horseradish peroxidase, β-galactosidase, luciferase, alkaline phosphatase.

The term "pharmaceutical agent or drug" as used herein refers to a chemical compound or composition capable of inducing a desired therapeutic effect when properly administered to a patient. Other chemistry terms herein are used according to conventional usage in the art, as exemplified by *The McGraw-Hill Dictionary of Chemical Terms* (Parker, S., Ed., McGraw-Hill, San Francisco (1985)), incorporated herein by reference.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise, more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The term "patient" includes human and veterinary subjects.

Human Antibodies and Humanization of Antibodies

Human antibodies avoid some of the problems associated with antibodies that possess murine or rat variable and/or constant regions. The presence of such murine or rat derived proteins can lead to the rapid clearance of the antibodies or can lead to the generation of an immune response against the antibody by a patient. In order to avoid the utilization of murine or rat derived antibodies, fully human antibodies can be generated through the introduction of functional human antibody loci into a rodent, other mammal or animal so that the rodent, other mammal or animal produces fully human antibodies.

One method for generating fully human antibodies is through the use of XENOMOUSE® strains of mice that have been engineered to contain 245 kb and 190 kb-sized germline configuration fragments of the human heavy chain locus and kappa light chain locus. Other XenoMouse strains of mice contain 980 kb and 800 kb-sized germline configuration fragments of the human heavy chain locus and kappa light chain locus. Still other XenoMouse strains of mice contain 980 kb and 800 kb-sized germline configuration fragments of the human heavy chain locus and kappa light chain locus plus a 740 kb-sized germline configured complete human lambda light chain locus. See Mendez et al. *Nature Genetics* 15:146-156 (1997) and Green and Jakobovits *J. Exp. Med.* 188:483-495 (1998). The XENOMOUSE® strains are available from Abgenix, Inc. (Fremont, Calif.).

The production of the XENOMOUSE® is further discussed and delineated in U.S. patent application Ser. No. 07/466,008, filed Jan. 12, 1990, Ser. No. 07/610,515, filed Nov. 8, 1990, Ser. No. 07/919,297, filed Jul. 24, 1992, Ser. No. 07/922,649, filed Jul. 30, 1992, filed 08/031,801, filed Mar. 15, 1993, Ser. No. 08/112,848, filed Aug. 27, 1993, Ser. No. 08/234,145, filed Apr. 28, 1994, Ser. No. 08/376,279, filed Jan. 20, 1995, Ser. No. 08/430,938, Apr. 27, 1995, Ser. No. 08/464,584, filed Jun. 5, 1995, Ser. No. 08/464,582, filed Jun. 5, 1995, Ser. No. 08/463,191, filed Jun. 5, 1995, Ser. No. 08/462,837, filed Jun. 5, 1995, Ser. No. 08/486,853, filed Jun. 5, 1995, Ser. No. 08/486,857, filed Jun. 5, 1995, Ser. No. 08/486,859, filed Jun. 5, 1995, Ser. No. 08/462,513, filed Jun. 5, 1995, Ser. No. 08/724,752, filed Oct. 2, 1996, and Ser. No. 08/759,620, filed Dec. 3, 1996, U.S. Patent Publication 2003/0217373, filed Nov. 20, 2002, and U.S. Pat. Nos. 6,833,268, 6,162,963, 6,150,584, 6,114,598, 6,075,181, and 5,939,598 and Japanese Patent Nos. 3 068 180 B2, 3 068 506 B2, and 3 068 507 B2. See also European Patent No., EP 0 463 151 B1, grant published Jun. 12, 1996, International Patent Application No., WO 94/02602, published Feb. 3, 1994, International Patent Application No., WO 96/34096, published Oct. 31, 1996, WO 98/24893, published Jun. 11, 1998, WO 00/76310, published Dec. 21, 2000. The disclosures of each of the above-cited patents, applications, and references are hereby incorporated by reference in their entirety.

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more V$_H$ genes, one or more D$_H$ genes, one or more J$_H$ genes, a mu constant region, and a second constant region (preferably a gamma constant region) are formed into a construct for insertion into an animal. This approach is described in U.S. Pat. No. 5,545,807 to Surani et al. and U.S. Pat. Nos. 5,545,806, 5,625,825, 5,625,126, 5,633,425, 5,661,016, 5,770,429, 5,789,650, 5,814,318, 5,877,397, 5,874,299, and 6,255,458 each to Lonberg and Kay, U.S. Pat. Nos. 5,591,669 and 6,023.010 to Krimpenfort and Berns, U.S. Pat. Nos. 5,612,205, 5,721,367, and 5,789,215 to Berns et al., and U.S. Pat. No. 5,643,763 to Choi and Dunn, and GenPharm International U.S. patent application Ser. No. 07/574,748, filed Aug. 29, 1990, Ser. No. 07/575,962, filed Aug. 31, 1990, Ser. No. 07/810,279, filed Dec. 17, 1991, Ser. No. 07/853,408, filed Mar. 18, 1992, Ser. No. 07/904,068, filed Jun. 23, 1992, Ser. No. 07/990,860, filed Dec. 16, 1992, Ser. No. 08/053, 131, filed Apr. 26, 1993, Ser. No. 08/096,762, filed Jul. 22, 1993, Ser. No. 08/155,301, filed Nov. 18, 1993, Ser. No. 08/161,739, filed Dec. 3, 1993, Ser. No. 08/165,699, filed Dec. 10, 1993, Ser. No. 08/209,741, filed Mar. 9, 1994, the disclosures of which are hereby incorporated by reference. See also European Patent No. 0 546 073 B1, International Patent Application Nos. WO 92/03918, WO 92/22645, WO 92/22647, WO 92/22670, WO 93/12227, WO 94/00569, WO 94/25585, WO 96/14436, WO 97/13852, and WO 98/24884 and U.S. Pat. No. 5,981,175, the disclosures of which are hereby incorporated by reference in their entirety. See further Taylor et al., 1992, Chen et al., 1993, Tuaillon et al., 1993, Choi et al., 1993, Lonberg et al., (1994), Taylor et al., (1994), and Tuaillon et al., (1995), Fishwild et al., (1996), the disclosures of which are hereby incorporated by reference in their entirety.

Kirin has also demonstrated the generation of human antibodies from mice in which, through microcell fusion, large pieces of chromosomes, or entire chromosomes, have been introduced. See European Patent Application Nos. 773 288 and 843 961, the disclosures of which are hereby incorporated by reference. Additionally, KM™—mice, which are the result of cross-breeding of Kirin's Tc mice with Medarex's minilocus (Humab) mice have been generated. These mice possess the HC transchromosome of the Kirin mice and the kappa chain transgene of the Genpharm mice (Ishida et al., Cloning Stem Cells, (2002) 4:91-102).

Human antibodies can also be derived by in vitro methods. Suitable examples include, but are not limited to, phage display (CAT, Morphosys, Dyax, Biosite/Medarex, Xoma, Symphogen, Alexion (formerly Proliferon), Affimed) ribosome display (CAT), yeast display, and the like.

Preparation of Antibodies

Antibodies, as described herein, were prepared through the utilization of the XENOMOUSE® technology, as described below. Such mice, then, are capable of producing human immunoglobulin molecules and antibodies and are deficient in the production of murine immunoglobulin molecules and antibodies. Technologies utilized for achieving the same are disclosed in the patents, applications, and references disclosed in the background section herein. In particular, however, a preferred embodiment of transgenic production of mice and antibodies therefrom is disclosed in U.S. patent application Ser. No. 08/759,620, filed Dec. 3, 1996 and International Patent Application Nos. WO 98/24893, published Jun. 11, 1998 and WO 00/76310, published Dec. 21, 2000, the disclosures of which are hereby incorporated by reference. See also Mendez et al. *Nature Genetics* 15:146-156 (1997), the disclosure of which is hereby incorporated by reference.

Through the use of such technology, fully human monoclonal antibodies to a variety of antigens have been produced. Essentially, XENOMOUSE® lines of mice are immunized with an antigen of interest (e.g. IL-1β), lymphatic cells (such as B-cells) are recovered from the mice that expressed antibodies, and the recovered cell lines are fused with a myeloid-type cell line to prepare immortal hybridoma cell lines. These hybridoma cell lines are screened and selected to identify hybridoma cell lines that produced antibodies specific to the antigen of interest. Provided herein are methods for the production of multiple hybridoma cell lines that produce antibodies specific to IL-1β. Further, provided herein are characterization of the antibodies produced by such cell lines, including nucleotide and amino acid sequence analyses of the heavy and light chains of such antibodies.

Alternatively, instead of being fused to myeloma cells to generate hybridomas, B cells can be directly assayed. For example, CD19+B cells can be isolated from hyperimmune XENOMOUSE® mice and allowed to proliferate and differentiate into antibody-secreting plasma cells. Antibodies from the cell supernatants are then screened by ELISA for reactivity against the IL-1β immunogen. The supernatants might also be screened for immunoreactivity against fragments of IL-1β to further map the different antibodies for binding to domains of functional interest on IL-1β. The antibodies may also be screened against other related human interleukins and against the rat, the mouse, and non-human primate, such as cynomolgus monkey, orthologues of IL-1β, the last to determine species cross-reactivity. B cells from wells containing antibodies of interest may be immortalized by fusion to make hybridomas either from individual or from pooled wells, or immortalized by infection with EBV or transfection by known immortalizing genes and then plating in suitable medium. Alternatively, single plasma cells secreting antibodies with the desired specificities are then isolated using an IL-1β-specific hemolytic plaque assay (Babcook et al., *Proc. Natl. Acad. Sci. USA* 93:7843-48 (1996)). Cells targeted for lysis are preferably sheep red blood cells (SRBCs) coated with the IL-1β antigen.

In the presence of a B-cell culture containing plasma cells secreting the immunoglobulin of interest and complement, the formation of a plaque indicates specific IL-1β-mediated lysis of the sheep red blood cells surrounding the plasma cell of interest. The single antigen-specific plasma cell in the center of the plaque can be isolated and the genetic information that encodes the specificity of the antibody is isolated from the single plasma cell. Using reverse-transcriptase followed by PCR (RT-PCR), the DNA encoding the heavy and light chain variable regions of the antibody can be cloned. Such cloned DNA can then be further inserted into a suitable expression vector, preferably a vector cassette such as a pcDNA, more preferably such a pcDNA vector containing the constant domains of immunoglobulin heavy and light chain. The generated vector can then be transfected into host cells, e.g., HEK293 cells, CHO cells, and cultured in conventional nutrient media modified as appropriate for inducing promoters, selecting transformants, or amplifying the genes encoding the desired sequences.

In general, antibodies produced by the fused hybridomas were human IgG4 heavy chains with fully human kappa or lambda light chains. Antibodies described herein possess human IgG4 heavy chains as well as IgG2 heavy chains. Antibodies can also be of other human isotypes, including IgG1. The antibodies possessed high affinities, typically possessing a $K_D$ of from about $10^{-6}$ through about $10^{-13}$ M or below, when measured by solid phase and solution phase techniques. Antibodies possessing a $K_D$ of no more than $10^{-11}$ M are preferred to inhibit the activity of IL-1β.

As will be appreciated, anti-IL-1β antibodies can be expressed in cell lines other than hybridoma cell lines. Sequences encoding particular antibodies can be used to transform a suitable mammalian host cell. Transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216, 4,912,040, 4,740,461, and 4,959,455 (which patents are hereby incorporated herein by reference). The transformation procedure used depends upon the host to be transformed. Methods for introducing heterologous polynucleotides into mammalian cells are well known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. Cell lines of particular preference are selected through determining which cell lines have high expression levels and produce antibodies with constitutive IL-1β binding properties.

Anti-IL-1β antibodies are useful in the detection of IL-1β in patient samples and accordingly are useful as diagnostics for disease states as described herein. In addition, based on their ability to significantly neutralize IL-1β activity (as demonstrated in the Examples below), anti-IL-1β antibodies have therapeutic effects in treating symptoms and conditions resulting from IL-1β. In specific embodiments, the antibodies and methods herein relate to the treatment of symptoms resulting from IL-1β induced disorders or IL-1β related disorders. Further embodiments involve using the antibodies and methods described herein to treat IL-1β-related disorders. IL-1β-related disorders can include inflammatory disorders, such as immune-mediated inflammatory disorders (IMID), which are inflammatory conditions caused and sustained by an antigen-specific, pathological immune response. Among these disorders are various types of arthritis, such as rheumatoid arthritis and juvenile rheumatoid arthritis, ankylosing spondylitis, Still's disease, and Behcet's disease. Other IMID are allergic diseases, such as asthma, hay fever, and urticaria; diseases caused by immune complexes, e.g., systemic lupus erythematosus, glomerulonephritis, pemphigus; vasculitis, such as Wegener's granulomatosis and Kawasaki's syndrome; different types of connective tissue disorders; inflammatory bowel disease (e.g., Crohn's disease and ulcerative colitis); insulin-dependent diabetes; multiple sclerosis; psoriasis; uveitis; retinitis; graft rejection; and graft-versus host-disease. IL-1β-related disorders can also include the pathogenesis of systemic inflammatory disorders, e.g., sepsis or familial Mediterranean fever and the Muckle-Wells syndrome. Also included are tissue inflammation in infectious, ischemic, hemorrhagic, and traumatic conditions, e.g., fasciitis, stroke, infarction of the myocardium and other organs (e.g., lung and intestine), ARDS; hepatitis, (e.g., infectious and non-infectious, acute and chronic); acute and chronic pancreatitis; reperfusion injuries; radiation injuries; vascular restenosis of different types (e.g., coronary restenosis); and orthopedic and dental injuries ranging from muscle strain, to ligament sprain, to periodontal disease. IL-1β related disorders further can include the pathogenesis of systemic disturbances of less obvious inflammatory nature, such as cachexia, chronic fatigue syndrome, anorexia and sleep and mental alterations (e.g., learning impairment), osteoarthritis, osteoporosis, atherosclerosis, organ fibrosis (e.g., lung and liver fibrosis), Alzheimer's disease, Parkinson's syndromes, amyelolateroschlerosis, and various myopathies, which are considered chiefly degenerative in nature but whose pathogenesis includes inflammatory components. IL-1β related disorders can include hyperalgesia of various types and cancer-related pain. IL-1β related disorders can include congestive heart failure, independently of primary heart disease. IL-1β related disorders can include cancer, blood malignancies, e.g., leukemias and multiple myelomas; the development of a number of solid tumors, tumor growth, and metastatic spreading. As will be appreciated by one of skill in the art, in some embodiments, the antibodies disclosed herein can be used to not only identify the above disorders, but to also treat, cure, or prevent such disorders. As such, methods and compositions for the detection, treatment, prevention, etc. of such disorders involving the herein disclosed antibodies are contemplated for the above disorders and related disorders. The above list can also serve as examples of treatable IL-1β related disorders.

In some embodiments, the general production of antibodies can involve the immunization of the animal with IL-1β, antibody generation (hybridoma, electrocell fusion), confirming human IgG IL-1β antibodies, producing antibodies for the assays, inhibiting IL-1β induced IL-6 production, running the top neutralizers on a BIACORE device to determine affinity, cloning the leads and sequencing them, determining the potency of inhibition by the antibodies, assessing the $K_D$, epitope mapping, mAb production, and in vivo testing.

Therapeutic Administration and Formulations

Embodiments of the invention include sterile pharmaceutical formulations of anti-IL-1β antibodies that are useful as treatments for diseases. Such formulations can inhibit the binding of IL-1β to its receptor, thereby effectively treating pathological conditions where, e.g., serum IL-1β is abnormally elevated. Anti-IL-1β antibodies preferably possess adequate affinity to potently neutralize IL-1β, and preferably have an adequate duration of action to allow for infrequent dosing in humans. A prolonged duration of action will allow for less frequent and more convenient dosing schedules by alternate parenteral routes such as subcutaneous or intramuscular injection.

Sterile formulations can be created, for example, by filtration through sterile filtration membranes, prior to or following lyophilization and reconstitution of the antibody. The antibody ordinarily will be stored in lyophilized form or in solution. Therapeutic antibody compositions generally are placed into a container having a sterile access port, for example, an intravenous solution bag or vial having an adapter that allows retrieval of the formulation, such as a stopper pierceable by a hypodermic injection needle.

The route of antibody administration is in accord with known methods, e.g., injection or infusion by intravenous, intraperitoneal, intracerebral, intramuscular, intraocular, intraarterial, intrathecal, inhalation or intralesional routes, or by sustained release systems as noted below. The antibody is preferably administered continuously by infusion or by bolus injection.

An effective amount of antibody to be employed therapeutically will depend, for example, upon the therapeutic objectives, the route of administration, and the condition of the patient. Accordingly, it is preferred that the therapist titer the dosage and modify the route of administration as required to obtain the optimal therapeutic effect. Typically, the clinician will administer antibody until a dosage is reached that achieves the desired effect. The progress of this therapy is easily monitored by conventional assays or by the assays described herein.

Antibodies, as described herein, can be prepared in a mixture with a pharmaceutically acceptable carrier. This therapeutic composition can be administered intravenously or through the nose or lung, preferably as a liquid or powder aerosol (lyophilized). The composition may also be administered parenterally or subcutaneously as desired. When administered systemically, the therapeutic composition should be sterile, pyrogen-free and in a parenterally acceptable solution having due regard for pH, isotonicity, and stability. These conditions are known to those skilled in the art. Briefly, dosage formulations of the compounds described herein are prepared for storage or administration by mixing the compound having the desired degree of purity with physiologically acceptable carriers, excipients, or stabilizers. Such materials are non-toxic to the recipients at the dosages and concentrations employed, and include buffers such as TRIS HCl, phosphate, citrate, acetate and other organic acid salts; antioxidants such as ascorbic acid; low molecular weight (less than about ten residues) peptides such as polyarginine, proteins, such as serum albumin, gelatin, or immunoglobulins; hydrophilic polymers such as polyvinylpyrrolidinone; amino acids such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium and/or nonionic surfactants such as TWEEN, PLURONICS or polyethyleneglycol.

Sterile compositions for injection can be formulated according to conventional pharmaceutical practice as described in Remington: *The Science and Practice of Pharmacy* (20$^{th}$ ed, Lippincott Williams & Wilkens Publishers (2003)). For example, dissolution or suspension of the active compound in a vehicle such as water or naturally occurring vegetable oil like sesame, peanut, or cottonseed oil or a synthetic fatty vehicle like ethyl oleate or the like may be desired. Buffers, preservatives, antioxidants, and the like can be incorporated according to accepted pharmaceutical practice.

Suitable examples of sustained-release preparations include semipermeable matrices of solid hydrophobic polymers containing the polypeptide, which matrices are in the form of shaped articles, films or microcapsules. Examples of sustained-release matrices include polyesters, hydrogels (e.g., poly(2-hydroxyethyl-methacrylate) as described by Langer et al., *J. Biomed Mater. Res.*, (1981) 15:167-277 and Langer, *Chem. Tech.*, (1982) 12:98-105, or poly(vinylalcohol)), polylactides (U.S. Pat. No. 3,773,919, EP 58,481), copolymers of L-glutamic acid and gamma ethyl-L-glutamate (Sidman et al., *Biopolymers*, (1983) 22:547-556), non-degradable ethylene-vinyl acetate (Langer et al., supra), degradable lactic acid-glycolic acid copolymers such as the LUPRON Depot™ (injectable microspheres composed of lactic acid-glycolic acid copolymer and leuprolide acetate), and poly-D-(-)-3-hydroxybutyric acid (EP 133,988).

While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S—S bond formation through disulfide interchange, stabilization may be achieved by modifying sulfhydryl residues, lyophilizing from acidic solutions, controlling moisture content, using appropriate additives, and developing specific polymer matrix compositions.

Sustained-released compositions also include preparations of crystals of the antibody suspended in suitable formulations capable of maintaining crystals in suspension. These preparations when injected subcutaneously or intraperitonealy can produce a sustained release effect. Other compositions also include liposomally entrapped antibodies. Liposomes containing such antibodies are prepared by methods known per se: DE 3,218,121; Epstein et al., *Proc. Natl. Acad. Sci. USA*, (1985) 82:3688-3692; Hwang et al., *Proc. Natl. Acad. Sci. USA*, (1980) 77:4030-4034; EP 52,322; EP 36,676; EP 88,046; EP 143,949; 142,641; Japanese patent application 83-118008; U.S. Pat. Nos. 4,485,045 and 4,544,545; and EP 102,324.

The dosage of the antibody formulation for a given patient will be determined by the attending physician taking into consideration various factors known to modify the action of drugs including severity and type of disease, body weight, sex, diet, time and route of administration, other medications and other relevant clinical factors. Therapeutically effective dosages may be determined by either in vitro or in vivo methods.

An effective amount of the antibodies, described herein, to be employed therapeutically will depend, for example, upon the therapeutic objectives, the route of administration, and the condition of the patient. Accordingly, it is preferred for the therapist to titer the dosage and modify the route of administration as required to obtain the optimal therapeutic effect. A typical daily dosage might range from about 0.001 mg/kg to up to 100 mg/kg or more, depending on the factors mentioned above. Typically, the clinician will administer the therapeutic antibody until a dosage is reached that achieves the desired effect. The progress of this therapy is easily monitored by conventional assays or as described herein.

It will be appreciated that administration of therapeutic entities in accordance with the compositions and methods herein will be administered with suitable carriers, excipients, and other agents that are incorporated into formulations to provide improved transfer, delivery, tolerance, and the like. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." *Regul. Toxicol. Pharmacol.* 32(2): 210-8 (2000), Wang W. "Lyophilization and development of solid protein pharmaceuticals." *Int. J. Pharm.* 203(1-2):1-60 (2000), Charman W N "Lipids, lipophilic drugs, and oral drug delivery-some emerging concepts." *J Pharm Sci* 89(8):967-78 (2000), Powell et al. "Compendium of excipients for parenteral formulations" *PDA J Pharm Sci Technol.* 52:238-311 (1998) and the citations therein for additional information related to formulations, excipients and carriers well known to pharmaceutical chemists.

EXAMPLES

The following examples, including the experiments conducted and results achieved are provided for illustrative purposes only and are not to be construed as limiting upon the teachings herein.

Example 1

Immunization and Titering

Immunization

Recombinant human IL-1beta (rhIL-1b) obtained from R&D Systems, Inc. (Minneapolis, Minn. Cat. No. 201-LB/

CF) was used as an antigen (shown in SEQ ID NO: 77). Monoclonal antibodies against IL-1β were developed by sequentially immunizing XenoMouse® mice (U.S. Pat. No. 6,833,268, Issued Dec. 24, 2004 to Green et al., hereby incorporated by reference in its entirety) (XenoMouse strains XMG1(3B3L3), XMG2(XMG2L3) and XMG4 (3C-1, 3C-1L3, XMG4Lstrain), Abgenix, Inc. Fremont, Calif.). XenoMouse animals were immunized via footpad route for all injections. The total volume of each injection was 50 μl per mouse, 25 μl per footpad.

For Cohort 1 (10 3B3L3 mice), Cohort 2 (10 3C-1L3 mice), and Cohort 3 (10 XMG2L3 mice), the initial immunization was with 10 μg of rhIL-1b admixed 1:1 (v/v) with TITERMAX GOLD® (Sigma, Oakville, ON) per mouse. The subsequent four boosts were made with 10 μg of rhIL-1b admixed 1:1 (v/v) with 100 μg alum gel (Sigma, Oakville, ON) in pyrogen-free D-PBS. The fifth boost consisted of 10 μg of rhIL-1b admixed 1:1 (v/v) with TITERMAX GOLD®. The sixth injection consisted of 10 μg of rhIL-1b admixed 1:1 v/v with 100 μg alum gel. A final boost was made with 10 μg rhIL-1b in pyrogen-free DPBS, without adjuvant. The XenoMouse mice were immunized on days 0, 3, 6, 8, 12, 15, 19, 22, and 25 for this protocol and fusions were performed on day 29.

For Cohort 4 (5 XM3C-1 mice), Cohort 5 (5 3C-1L3 mice), Cohort 6 (5 XMG4L mice), Cohort 7 (5 XM3C-1 mice), Cohort 8 (5 3C-1L3 mice), and Cohort 9 (5 XMG4L mice), the first injection was with 10 ug rhIL-1b in pyrogen-free Dulbecco's PBS (DPBS) admixed 1:1 (v/v) with TITERMAX GOLD® (Sigma, Oakville, ON) per mouse. The next 10 boosts were with 10 μg rhIL-1b in pyrogen-free DPBS, admixed with 25 μg of Adju-Phos (aluminum phosphate gel, Catalog # 1452-250, batch #8937, HCI Biosector) and 10 μg CpG (15 μl of ImmunEasy Mouse Adjuvant, catalog # 303101; lot #11553042; Qiagen) per mouse. A final boost consisted of 10 μg rhIL-1b in pyrogen-free DPBS, without adjuvant. From Cohort 4 to Cohort 6, the XenoMouse mice were immunized on days 0, 3, 7, 10, 14, 20, 38, 41, 45, 48, 52, and 55 for this protocol and fusions were performed on day 59. The two bleeds were made through Retro-Orbital Bleed procedure on day 22 after the sixth boost and on day 42 after the eighth boost. From Cohort 7 to Cohort 9, the XenoMouse mice were immunized on days 0, 4, 7, 11, 17, 21, 38, 42, 46, 50, 53, and 57 for this protocol and fusions were performed on day 61. The two bleeds were made through Retro-Orbital Bleed procedure on day 26 after the sixth boost and day 45 after the eighth boost.

Selection of Animals for Harvest by Titer

IL-1β antibody titers in the serum from immunized XenoMouse mice were determined by ELISA. Briefly, rhIL-1 beta (1 μg/ml) was coated onto Costar Labcoat Universal Binding Polystyrene 96-well plates (Corning, Acton, Mass.) overnight at 4° C. in Antigen Coating Buffer (0.1 M Carbonate Buffer, pH 9.6 NaHCO$_3$ (MW 84) 8.4 g/L). The next day, the plates were washed three times with washing buffer (0.05% Tween 20 in 1×PBS) using a Biotek plate washer. The plates were then blocked with 200 μl/well blocking buffer (0.5% BSA, 0.1% Tween 20, 0.01% Thimerosal in 1×PBS) and incubated at room temperature for 1 h. After the one-hour blocking, the plates were washed three times with washing buffer using a Biotek plate washer. Sera from either IL-1 beta immunized XenoMouse mice or naïve XenoMouse animals were titrated in 0.5% BSA/PBS buffer at 1:3 dilutions in duplicate from a 1:100 initial dilution. The last well was left blank. These plates were incubated at room temperature for 2 h, and the plates were then washed three times with washing buffer using a Biotek plate washer. A goat anti-human IgG Fc-specific horseradish peroxidase (HRP, Pierce, Rockford, Ill.) conjugated antibody was added at a final concentration of 1 μg/ml and incubated for 1 hour at room temperature. The plates were washed three times with washing buffer using a Biotek plate washer. After washing, the plates were developed with the addition of TMB chromogenic substrate (BioFx BSTP-0100-01) for 10-20 min or until negative control wells start to show color. Then the ELISA was stopped by the addition of Stop Solution (650 nM Stop reagent for TMB (BioFx BSTP-0100-01), reconstituted with 100 ml H$_2$O per bottle). The specific titer of each XenoMouse animal was determined from the optical density at 650 nm and is shown in Tables 2-10 below. The titer value is the reciprocal of the greatest dilution of sera with an OD reading two-fold that of background. Therefore, the higher the number, the greater was the humoral immune response to IL-1B.

TABLE 2

Group 1, fp, 3c-1L3, 10 mice

| Mouse ID | After 4 inj. | After 6 inj. |
|---|---|---|
| N946-4 | 300 | 100 |
| N947-2 | 325 | 2,500 |
| N995-3 | 325 | 8,100 |
| N995-5 | 275 | 4,500 |
| O001-4 | 650 | 20,000 |
| O001-6 | 600 | 23,000 |
| O002-2 | 175 | 1,800 |
| O003-5 | 60 | 7,500 |
| O003-6 | 20 | 4,000 |
| O005-3 | 1,500 | 21,500 |
| NC(h) | <100 | <100 |
| NC(m) | negative | negative |
| PC(m) Sensitivity | 0.4 ng/ml | 0.4 ng/ml |
| NC(h) | 3c-5 KLH gp1; bip L487-9; Bleed Apr. 16, 2001 | |
| NC(m) | D39.2.1 Mab (ll-8); 1 ug/ml anti-hll-1b mAb; Cat MAB601 | |
| PC(m) | Lot GY179121; R&D Systems; start from 1 ug/ml | |

TABLE 3

Group 2, fp, 3b-3L3, 10 mice

| Mouse ID | After 4 inj. | After 6 inj. |
|---|---|---|
| N636-9 | 60 | 1,300 |
| N642-5 | 55 | 9,000 |
| N646-7 | 2,400 | 16,000 |
| N711-5 | 50 | 500 |
| N714-5 | 5,000 | 45,000 |
| N716-2 | 140 | 2,000 |
| N716-4 | 7,500 | 14,000 |
| N729-5 | <100 | <100 |
| N733-7 | 1,500 | 20,000 |
| N736-7 | 2,500 | 35,000 |
| NC(h) | <100 | <100 |
| NC(m) | negative | negative |
| PC(m) Sensitivity | 0.4 ng/ml | 0.4 ng/ml |
| NC(h) | 3b-3 Mn gp1; fp L955-7; bleed May 11, 2001 | |
| NC(m) | D39.2.1 Mab (ll-8) 1 ug/ml anti-hll-1b mAb; Cat MAB601 | |
| PC(m) | Lot GY179121; R&D Systems; start from 1 ug/ml | |

TABLE 4

Group 3, fp, xmg2L3, 9 mice

| Mouse ID | After 4 inj. | After 6 inj. |
|---|---|---|
| N701-5 | 2,100 | 70,000 |
| N751-3 | 6,000 | 100,000 |
| N751-4 | 22,000 | 125,000 |
| N751-6 | 7,000 | 65,000 |
| N763-1 | 2,500 | 67,000 |

TABLE 4-continued

Group 3, fp, xmg2L3, 9 mice

| Mouse ID | After 4 inj. | After 6 inj. |
|---|---|---|
| N769-4 | 21,000 | 200,000 |
| N770-1 | 175 | 68,000 |
| N773-2 | 800 | 25,000 |
| N774-2 | 750 | 72,900 |
| NC(h) | 3,000 | 3,000 |
| NC(m) | negative | negative |
| PC(m) Sensitivity | 0.4 ng/ml | 0.4 ng/ml |
| NC(h) | xmg2 KLH gp1; fp L627-3; Fusion Jan. 9, 2001 | |
| NC(m) | D39.1.1 Mab (ll-8); 1 ug/ml anti-hIl-1b mAb; Cat MAB601 | |
| PC(m) | Lot GY179121; R&D Systems; start from 1 ug/ml | |

TABLE 5

Group 4, fp, xm3C-1, 5 mice

| Mouse ID | After 6 inj. | After 8 inj. |
|---|---|---|
| P382-7 | 50 | 85 |
| P382-8 | 40 | 275 |
| P382-3 | 55 | 275 |
| P382-4 | 75 | 50 |
| P382-6 | 75 | 90 |
| NC | 200 | 200 |
| PC | 800 | 800 |

TABLE 6

Group 5, fp, xm3C-1L3, 5 mice

| Mouse ID | After 6 inj. | After 8 inj. |
|---|---|---|
| P375-1 | 50 | 250 |
| P375-2 | 35 | 400 |
| P376-6 | 65 | 425 |
| P420-1 | 55 | 150 |
| P420-2 | 40 | 750 |
| NC | 175 | 175 |
| PC | 1,000 | 1,000 |

TABLE 7

Group 6, fp, xmg4L, 5 mice

| Mouse ID | After 6 inj. | After 8 inj. |
|---|---|---|
| P528-8 | 30 | 30 |
| P531-3 | 10 | 900 |
| P531-4 | 15 | 100 |
| P531-5 | 250 | 100 |
| P531-6 | 85 | 70 |
| NC | 85 | 85 |
| PC | 1,300 | 1,300 |

TABLE 8

Group 7, fp, xm3C-1, 5 mice

| Mouse ID | After 6 inj. | After 8 inj. |
|---|---|---|
| P525-1 | 55 | NoBleed |
| P527-2 | 55 | 50 |
| P527-3 | 30 | 55 |
| P527-4 | 50 | 200 |
| P527-5 | 80 | 55 |

TABLE 8-continued

Group 7, fp, xm3C-1, 5 mice

| Mouse ID | After 6 inj. | After 8 inj. |
|---|---|---|
| NC | 175 | 175 |
| PC | 1,000 | 1,000 |

TABLE 9

Group 8, fp, xm3C-1L3, 5 mice

| Mouse ID | After 4 inj. | After 6 inj. |
|---|---|---|
| P420-4 | 100 | 225 |
| P447-1 | 40 | 1,400 |
| P447-2 | 30 | 600 |
| P447-3 | 95 | 20 |
| P-447-4 | 80 | 25 |
| NC | 150 | 150 |
| PC | 850 | 850 |

TABLE 10

Group 9, fp, xmg4L, 5 mice

| Mouse ID | After 4 inj. | After 6 inj. |
|---|---|---|
| P378-3 | 20 | 20 |
| P380-7 | 15 | 45 |
| P456-5 | 55 | 300 |
| P529-9 | 40 | 40 |
| P530-6 | 40 | 95 |
| NC | 175 | 175 |
| PC | 850 | 850 |

For all datasets (groups 3 through 9), NC was LX015 gp2; fp, xm3C-1; and PC was IL-1β (xmg2L3); gp3, fp, (+) 1:100.

Example 2

Recovery of Lymphocytes, B-Cell Isolations, Fusions and Generation of Hybridomas Immunized mice were sacrificed and the lymph nodes were harvested and pooled from each cohort. The lymphoid cells were dissociated by grinding in DMEM to release the cells from the tissues, and the cells were suspended in DMEM. The cells were counted, and 0.9 ml DMEM per 100 million lymphocytes was added to the cell pellet to resuspend the cells gently but completely. Using 100 µl of CD90+ magnetic beads per 100 million cells, the cells were labeled by incubating the cells with the magnetic beads at 4° C. for 15 minutes. The magnetically-labeled cell suspension containing up to $10^8$ positive cells (or up to $2\times10^9$ total cells) was loaded onto a LS+ column and the column washed with DMEM. The total effluent was collected as the CD90-negative fraction (most of these cells were expected to be B cells).

The fusion was performed by mixing washed enriched B cells from above and nonsecretory myeloma P3X63Ag8.653 cells purchased from ATCC, cat.# CRL 1580 (Kearney et al., J. Immunol. 123, 1979, 1548-1550) at a ratio of 1:1. The cell mixture was gently pelleted by centrifugation at 800 g. After complete removal of the supernatant, the cells were treated with 2-4 mL of Pronase solution (CalBiochem, cat. # 53702; 0.5 mg/mL in PBS) for no more than 2 minutes. Then 3-5 ml of FBS was added to stop the enzyme activity and the suspension was adjusted to 40 mL total volume using electro cell fusion solution, ECFS (0.3 M Sucrose, Sigma, Cat# S7903, 0.1 mM Magnesium Acetate, Sigma, Cat# M2545, 0.1 mM Calcium Acetate, Sigma, Cat# C4705). The supernatant was removed after centrifugation and the cells were resuspended in 40 mL ECFS. This wash step was repeated and the cells again were resuspended in ECFS to a concentration of $2 \times 10^6$ cells/mL.

Electro-cell fusion was performed using a fusion generator, model ECM2001, Genetronic, Inc., San Diego, Calif. The fusion chamber size used was 2.0 mL, using the following instrument settings: alignment condition: voltage: 50 V, time: 50 s; membrane breaking at: voltage: 3000 V, time: 30 μsec; post-fusion holding time: 3 sec.

After ECF, the cell suspensions were carefully removed from the fusion chamber under sterile conditions and transferred into a sterile tube containing the same volume of Hybridoma Culture Medium (DMEM (JRH Biosciences), 15% FBS (Hyclone), supplemented with L-glutamine, pen/strep, OPI (oxaloacetate, pyruvate, bovine insulin) (all from Sigma) and IL-6 (Boehringer Mannheim)). The cells were incubated for 15-30 minutes at 37° C., and then centrifuged at 400 g for five minutes. The cells were gently resuspended in a small volume of Hybridoma Selection Medium (Hybridoma Culture Medium supplemented with 0.5×HA (Sigma, cat. # A9666)), and the volume was adjusted appropriately with more Hybridoma Selection Medium, based on a final plating of $5 \times 10^6$ B cells total per 96-well plate and 200 μL per well. The cells were mixed gently and pipetted into 96-well plates and allowed to grow. On day 7 or 10, one-half the medium was removed, and the cells were re-fed with Hybridoma Selection Medium.

Example 3

Selection of Candidate Antibodies by Elisa

After 14 days of culture, hybridoma supernatants were screened for IL-1B-specific monoclonal antibodies. In the primary screen, the ELISA plates (Fisher, Cat. No. 12-565-136) were coated with 50 μL/well of IL-1b (1 μg/mL) in Coating Buffer (0.1 M Carbonate Buffer, pH 9.6, $NaHCO_3$ 8.4 g/L), then incubated at 4° C. overnight. After incubation, the plates were washed with Washing Buffer (0.05% Tween 20 in PBS) three times. 200 μL/well Blocking Buffer (0.5% BSA, 0.1% Tween 20, 0.01% Thimerosal in 1×PBS) were added and the plates were incubated at room temperature for 1 h. After incubation, the plates were washed with Washing Buffer three times. Aliquots (50 μL/well) of hybridoma supernatants and positive and negative controls were added, and the plates were incubated at room temperature for 2 h. The positive control used throughout was serum from the relevant hIL-1b immunized XenoMouse mouse and the negative control was serum from the KLH-immunized relevant strain of XenoMouse mouse. After incubation, the plates were washed three times with Washing Buffer. 100 μL/well of detection antibody goat anti-huIgGfc-HRP (Caltag, Cat. No. H10507, using concentration was 1:2000 dilution) was added and the plates were incubated at room temperature for 1 hour. After incubation, the plates were washed three times with Washing Buffer. 100 μl/well of TMB (BioFX Lab. Cat. No. TMSK-0100-01) was added, and the plates were allowed to develop for about 10 minutes (until negative control wells barely started to show color). 50 μl/well stop solution (TMB Stop Solution (BioFX Lab. Cat. No. STPR-0100-01) was then added and the plates were read on an ELISA plate reader at a wavelength of 450 nm.

The old culture supernatants from the positive hybridoma cells growth wells based on primary screen were removed and the IL-1B positive hybridoma cells were suspended with fresh hybridoma culture medium and were transferred to 24-well plates. After 2 days in culture, these supernatants were ready for a secondary confirmation screen. In the secondary confirmation screen, the positives in the first screening were screened in direct ELISA (described as above) and Sandwich ELISA, and three sets of detective system for each method, one set for hIgG detection, one set for human lambda light chain detection (goat anti-hIg lambda-HRP, Southern Biotechnology, Cat. No. 2070-05) and the other set for human Ig kappa light chain detection (goat anti-hIg kappa-HRP, Southern Biotechnology, Cat. No. 2060-05) in order to demonstrate fully human composition for both IgG and Ig kappa or IgG and Ig lambda or IgG and Ig kappa plus lambda. The three sets of direct ELISA procedures were identical to the descriptions above except the three different detection antibodies were used separately. The Streptavidin pre-coated plates (Cat # M-5432, Sigma) were used for the Sandwich ELISAs. Blocking Buffer (100 μL/well) containing 1 μg/mL of rhIL-1b was added to the Streptavidin pre-coated plates. The plates were incubated at room temperature for 1 h. After incubation, the plates were washed with Washing Buffer three times. 50 μL/well of hybridoma supernatants (the positives from the first screening) and positive and negative controls were added, and the plates were incubated at room temperature for 2 h. The remaining procedures were identical to the three sets of direct ELISA described above.

All positive hits from the ELISA assay were counter screened for binding to IL-1α by ELISA in order to exclude those that cross-react with IL-1α. The ELISA plates (Fisher, Cat. No. 12-565-136) were coated with 50 μL/well of recombinant hIL-1α(R&D cat# 200-LA) in Coating Buffer (0.1 M Carbonate Buffer, pH 9.6, $NaHCO_3$ 8.4 g/L), then incubated at 4° C. overnight. The remaining procedures were identical to the descriptions above.

There were 614 fully human IgG/kappa or IgG/lambda IL-1b specific monoclonal antibodies that were generated. The number of antibodies resulting from this process is summarized in Table 11 for each fusion.

TABLE 11

| Assay | Fusion # | # hIgG positive | | |
|---|---|---|---|---|
| Primary screen | fusion 1 (3B-3L3) | 171 | | |
| | fusion 2 (3C-1L3) | 120 | | |
| | fusion 3(xgm2L3) | 447 | | |
| | fusion 4(3C-1) | 82 | | |
| | fusion 5(3C-1L3) | 85 | | |
| | fusion 6(xgm4L) | 170 | | |
| | fusion 7(3C-1) | 2 | | |
| | fusion 8(3C-1L3) | 99 | | |
| | fusion 9(xgm4L) | 204 | | |
| | fusion 10(3C-1) | 5 | | |
| | fusion 11(3C-1L3) | 17 | | |
| | fusion 12(xgm4L) | 16 | | |

| | | | hIgG/ | hIgG/hkappa/ |
| Second | Fusion # | hIgG/hkappa | hlamdba | hlambda |
|---|---|---|---|---|
| screen | fusion 1 (3B-3L3) | 51 | 38 | 7 |
| | fusion 2 (3C-1L3) | 24 | 22 | 0 |
| | fusion 3(xgm2L3) | 60 | 43 | 12 |
| | fusion 4(3C-1) | 24 | N/A | N/A |
| | fusion 5(3C-1L3) | 22 | 16 | 4 |
| | fusion 6(xgm4L) | 1 | 108 | 1 |
| | fusion 7(3C-1) | 2 | N/A | N/A |
| | fusion 8(3C-1L3) | 17 | 36 | 4 |

TABLE 11-continued

| | | | |
|---|---|---|---|
| fusion 9(xgm4L) | 1 | 160 | 1 |
| fusion 10(3C-1) | 4 | 0 | 0 |
| fusion 11(3C-1L3) | 3 | 4 | 0 |
| fusion 12(xgm4L) | 0 | 7 | 0 |

All fully human IgG/kappa or IgG/lambda IL-1β specific monoclonal antibodies were screened for binding to mouse IL-1β by ELISA in order to identify the species cross-reactivity. The ELISA plates (Fisher, Cat. No. 12-565-136) were coated with 50 μL/well of recombinant mIL-1b (R&D System, Recombinant Mouse IL-1β/IL-1F2, Carrier Free, Cat# 401-ML/CF) or cynomolgus IL-1β (R&D system, Recombinant Rhesus Macaque IL-1β/IL-1F2, Carrier Free Cat# 1318-RL/CF), 2 μg/mL (obtained from R&D Systems, Cat. # 293-AN-025/CF) in Coating Buffer (0.1 M Carbonate Buffer, pH 9.6, $NaHCO_3$ 8.4 g/L), then incubated at 4° C. overnight. The remaining procedures were identical to the descriptions above. There were no fully human IgG/kappa or IgG/lambda IL-1β specific monoclonal antibodies that were mouse species cross-reactive.

Example 4

Neutralization of IL-1β Induced IL-6 Production by Hybridoma Anti-IL-1β Antibodies 343 hybridoma supernatants containing IL-1β specific monoclonal antibodies were screened for their ability to neutralize IL-1β induced IL-6 production in MRC-5 cells (lung fibroblast cells). 96 well flat-bottom plates were seeded with 5000 MRC-5 cells per well in 100 μl of MEM, 1% FBS. The plates were incubated for 18-20 hours at 37° C.+5% $CO_2$ to allow cell adherence. Following cell adherence, media was removed from cells and replaced with 100 μl of hybridoma supernatant samples diluted 1:2.5 in MEM, 1% FBS. 100 μl of recombinant IL-1β (R&D Systems cat. # 201-LB) was added to a final concentration of 4 pM, resulting in a 1:5 final dilution of supernatant samples in the plate. Wells containing IL-1β alone and supernatant alone were included as controls. Plates were then incubated at 37° C.+5% $CO_2$ for an additional 24 hours. Supernatants were collected and assayed for human IL-6 levels by ELISA. Percent IL-6 production in each well was calculated compared to an IL-1β alone control (100% production). Samples with the ability to inhibit IL-6 production by 35% or greater we considered positive. Total number positive supernatants from each fusion are shown in Table 12 below.

TABLE 12

| Group # | Total # | Total # positive |
|---|---|---|
| Fusion 4 (3C-1) | 23 | 2 |
| Fusion 5 (3C-1L3) | 42 | 13 |
| Fusion 6 (xgm4L) | 96 | 17 |
| Fusion 7 (3C-1) | 2 | 0 |
| Fusion 8 (3C-1L3) | 65 | 24 |
| Fusion 9 (xgm4L) | 96 | 33 |
| Fusion 10 (3C-1) | 4 | 0 |
| Fusion 11 (3C-1L3) | 8 | 1 |
| Fusion 12 (xgm4L) | 7 | 0 |

The 90 positive hybridoma supernatants containing IL-1β antibodies were re-screened for their ability to neutralize IL-1β induced IL-6 production in MRC-5 cells at 1:5, 1:10 and 1:20 final dilution of supernatant samples in the plate. Results are shown in the FIGS. 1A-1D. FIGS. 1A-1D are bar graph displays of varying dilutions of the antibodies.

Example 5

Human IL-1β Low Resolution Biacore Screen of 97 mAb Hybridoma Cell Supernatants

The label-free surface plasmon resonance (SPR), or Biacore, was utilized to measure the antibody affinity to the antigen. For this purpose, a high-density goat anti-human antibody surface over a CM5 Biacore chip was prepared using routine amine coupling. All of the hybridoma cell supernatants were diluted two-fold in HBS-P running buffer containing 100 μg/ml BSA and 10 mg/mL carboxymethyl-dextran except for mAbs 8.59 and 9.9 which were not diluted. Each mAb was captured on a separate surface using a 180-second contact time, and a 5-minute wash for stabilization of the mAb baseline.

IL-1β was injected at 118 nM at 25° C. over all surfaces for 90 seconds, followed by a 5-minute dissociation. Double-referenced binding data was prepared by subtracting the signal from a control flow cell and subtracting the baseline drift of a buffer injection just prior to the IL-1β injection. Data were fit globally to a 1:1 interaction model to determine the binding kinetics. The kinetic analysis results of IL-1β binding at 25° C. are listed in Table 13 below. The mAbs are ranked from highest to lowest affinity.

TABLE 13

| Sample | Amt. Captured (RU) | $k_a$ ($M^{-1}s^{-1}$) | $k_d$ ($s^{-1}$) | $K_D$ (pM) |
|---|---|---|---|---|
| 9.19 | 572 | $5.6 \times 10^5$ | $1.5 \times 10^{-4}$ | 268 |
| 5.5 | 514 | $1.8 \times 10^6$ | $5.0 \times 10^{-4}$ | 278 |
| 9.100 | 230 | $6.1 \times 10^5$ | $1.7 \times 10^{-4}$ | 279 |
| 9.11 | 651 | $6.9 \times 10^5$ | $2.0 \times 10^{-4}$ | 290 |
| 6.33 | 508 | $5.0 \times 10^5$ | $1.6 \times 10^{-4}$ | 320 |
| 6.7 | 325 | $1.2 \times 10^6$ | $5.6 \times 10^{-4}$ | 350 |
| 9.54 | 359 | $2.3 \times 10^6$ | $8.5 \times 10^{-4}$ | 370 |
| 6.20 | 711 | $5.9 \times 10^5$ | $2.6 \times 10^{-4}$ | 441 |
| 6.26 | 686 | $9.2 \times 10^5$ | $4.4 \times 10^{-4}$ | 478 |
| 9.56 | 332 | $9.2 \times 10^5$ | $4.9 \times 10^{-4}$ | 533 |
| 5.12 | 499 | $5.9 \times 10^5$ | $3.3 \times 10^{-4}$ | 559 |
| 9.22 | 422 | $5.4 \times 10^5$ | $3.3 \times 10^{-4}$ | 611 |
| 8.18 | 323 | $3.5 \times 10^5$ | $2.2 \times 10^{-4}$ | 629 |
| 5.36 | 800 | $5.9 \times 10^5$ | $4.2 \times 10^{-4}$ | 712 |
| 9.2 | 500 | $9.9 \times 10^5$ | $7.4 \times 10^{-4}$ | 747 |
| 6.34 | 779 | $8.1 \times 10^5$ | $6.1 \times 10^{-4}$ | 753 |
| 9.26 | 375 | $4.1 \times 10^5$ | $3.5 \times 10^{-4}$ | 854 |
| 5.25 | 268 | $6.9 \times 10^5$ | $6.0 \times 10^{-4}$ | 870 |
| 9.47 | 268 | $3.3 \times 10^6$ | $3.0 \times 10^{-3}$ | 909* |
| 9.85 | 74 | $5.8 \times 10^5$ | $6.0 \times 10^{-4}$ | 1034 |
| 9.58 | 428 | $2.1 \times 10^6$ | $2.2 \times 10^{-3}$ | 1048* |
| 8.64 | 403 | $4.2 \times 10^5$ | $4.7 \times 10^{-4}$ | 1119 |
| 8.26 | 402 | $6.9 \times 10^5$ | $7.9 \times 10^{-4}$ | 1145 |
| 8.6 | 304 | $5.6 \times 10^5$ | $6.9 \times 10^{-4}$ | 1230 |
| 5.32 | 269 | $8.0 \times 10^5$ | $9.9 \times 10^{-4}$ | 1237 |
| 9.45 | 77 | $1.1 \times 10^6$ | $1.4 \times 10^{-3}$ | 1273 |
| 5.35 | 259 | $3.8 \times 10^5$ | $5.0 \times 10^{-4}$ | 1316 |
| 6.39 | 651 | $3.7 \times 10^5$ | $4.9 \times 10^{-4}$ | 1324 |
| 8.1 | 360 | $3.0 \times 10^5$ | $4.1 \times 10^{-4}$ | 1370 |
| 6.80 | 494 | $4.0 \times 10^5$ | $5.5 \times 10^{-4}$ | 1375 |
| 8.4 | 431 | $1.1 \times 10^6$ | $1.6 \times 10^{-3}$ | 1455 |

TABLE 13-continued

| Sample | Amt. Captured (RU) | $k_a$ (M$^{-1}$s$^{-1}$) | $k_d$ (s$^{-1}$) | $K_D$ (pM) |
|---|---|---|---|---|
| 9.94 | 299 | $4.6 \times 10^5$ | $7.3 \times 10^{-4}$ | 1587 |
| 9.5 | 305 | $1.1 \times 10^6$ | $1.8 \times 10^{-3}$ | 1640* |
| 6.65 | 357 | $4.2 \times 10^5$ | $7.0 \times 10^{-4}$ | 1667 |
| 9.71 | 307 | $3.9 \times 10^5$ | $6.5 \times 10^{-4}$ | 1667 |
| 9.72 | 325 | $3.7 \times 10^5$ | $6.6 \times 10^{-4}$ | 1784 |
| 6.24 | 649 | $1.2 \times 10^6$ | $2.2 \times 10^{-3}$ | 1833 |
| 5.24 | 482 | $4.3 \times 10^5$ | $8.1 \times 10^{-4}$ | 1880 |
| 8.59 | 139 | $1.9 \times 10^6$ | $3.6 \times 10^{-3}$ | 1895 |
| 9.95 | 408 | $3.2 \times 10^5$ | $6.3 \times 10^{-4}$ | 1969 |
| 6.85 | 1160 | $3.3 \times 10^5$ | $6.5 \times 10^{-4}$ | 1970 |
| 5.2 | 380 | $5.0 \times 10^5$ | $1.0 \times 10^{-3}$ | 2000 |
| 9.74 | 41 | $3.5 \times 10^5$ | $7.5 \times 10^{-4}$ | 2140 |
| 9.55 | 260 | $3.1 \times 10^5$ | $6.8 \times 10^{-4}$ | 2194 |
| 8.59 | 169 | $1.2 \times 10^6$ | $2.6 \times 10^{-3}$ | 2200 |
| 9.48 | 457 | $2.9 \times 10^5$ | $6.4 \times 10^{-4}$ | 2207 |
| 9.42 | 396 | $3.1 \times 10^5$ | $6.9 \times 10^{-4}$ | 2226 |
| 9.76 | 490 | $4.4 \times 10^5$ | $1.0 \times 10^{-3}$ | 2273 |
| 8.11 | 749 | $2.9 \times 10^5$ | $7.1 \times 10^{-4}$ | 2448 |
| 9.82 | 893 | $3.8 \times 10^5$ | $9.7 \times 10^{-4}$ | 2553 |
| 9.12 | 526 | $3.1 \times 10^5$ | $8.0 \times 10^{-4}$ | 2580 |
| 6.61 | 896 | $3.2 \times 10^5$ | $8.3 \times 10^{-4}$ | 2594 |
| 9.70 | 112 | $6.1 \times 10^5$ | $1.6 \times 10^{-3}$ | 2623 |
| 8.42 | 279 | $3.5 \times 10^5$ | $9.4 \times 10^{-4}$ | 2686 |
| 9.3 | 275 | $1.6 \times 10^5$ | $4.3 \times 10^{-4}$ | 2687 |
| 9.32 | 576 | $4.4 \times 10^5$ | $1.2 \times 10^{-3}$ | 2727 |
| 5.38 | 593 | $5.6 \times 10^5$ | $1.6 \times 10^{-3}$ | 2857 |
| 11.5 | 468 | $4.9 \times 10^5$ | $1.4 \times 10^{-3}$ | 2857 |
| 8.62 | 736 | $4.4 \times 10^5$ | $1.4 \times 10^{-3}$ | 3182 |
| 6.27 | 653 | $2.5 \times 10^5$ | $8.1 \times 10^{-4}$ | 3240 |
| 9.16 | 565 | $2.0 \times 10^6$ | $6.7 \times 10^{-3}$ | 3350 |
| 5.23 | 379 | $1.1 \times 10^6$ | $3.8 \times 10^{-3}$ | 3455 |
| 6.2 | 360 | $4.7 \times 10^5$ | $1.7 \times 10^{-3}$ | 3617 |
| 8.7 | 392 | $4.2 \times 10^5$ | $1.6 \times 10^{-3}$ | 3809 |
| 6.58 | 904 | $1.0 \times 10^6$ | $4.2 \times 10^{-3}$ | 4200 |
| 9.39 | 389 | $4.6 \times 10^5$ | $2.0 \times 10^{-3}$ | 4348 |
| 8.44 | 412 | $4.7 \times 10^5$ | $2.1 \times 10^{-3}$ | 4468 |
| 4.20 | 242 | $4.6 \times 10^5$ | $2.3 \times 10^{-3}$ | 5000 |
| 5.37 | 981 | $5.8 \times 10^5$ | $2.9 \times 10^{-3}$ | 5000 |
| 4.14 | 652 | $2.9 \times 10^5$ | $1.5 \times 10^{-3}$ | 5170 |
| 6.45 | 946 | $1.8 \times 10^6$ | $1.0 \times 10^{-2}$ | 5555 |
| 9.31 | 570 | $6.6 \times 10^5$ | $3.8 \times 10^{-3}$ | 5760 |
| 5.20 | 798 | $1.8 \times 10^6$ | $1.1 \times 10^{-2}$ | 6111 |
| 8.5 | 477 | $1.2 \times 10^6$ | $7.4 \times 10^{-3}$ | 6167 |
| 8.63 | 616 | $1.3 \times 10^6$ | $8.2 \times 10^{-3}$ | 6307 |
| 5.14 | 598 | $3.8 \times 10^5$ | $2.4 \times 10^{-3}$ | 6316 |
| 6.15 | 759 | $1.5 \times 10^6$ | $9.7 \times 10^{-3}$ | 6467 |
| 8.14 | 406 | $3.5 \times 10^5$ | $2.3 \times 10^{-3}$ | 6571 |
| 9.89 | 456 | $6.8 \times 10^5$ | $4.7 \times 10^{-3}$ | 6912 |
| 9.38 | 296 | $2.0 \times 10^6$ | $1.4 \times 10^{-2}$ | 7000 |
| 4.11 | 596 | $3.3 \times 10^5$ | $2.5 \times 10^{-3}$ | 7580 |
| 8.33 | 615 | $2.1 \times 10^6$ | $1.6 \times 10^{-2}$ | 7619 |
| 8.52 | 741 | $2.1 \times 10^6$ | $1.7 \times 10^{-2}$ | 8095 |
| 8.9 | 838 | $1.4 \times 10^6$ | $1.2 \times 10^{-2}$ | 8571 |
| 6.57 | 1160 | $3.1 \times 10^5$ | $2.7 \times 10^{-3}$ | 8710 |
| 8.50 | 473 | $3.0 \times 10^6$ | $2.7 \times 10^{-2}$ | 9000 |
| 8.61 | 591 | $4.7 \times 10^5$ | $5.3 \times 10^{-3}$ | $1.13 \times 10^4$ |
| 8.17 | 657 | $2.7 \times 10^6$ | $3.2 \times 10^{-2}$ | $1.18 \times 10^4$ |
| 8.21 | 895 | $1.5 \times 10^6$ | $1.9 \times 10^{-2}$ | $1.27 \times 10^4$ |
| 8.55 | 1010 | $1.6 \times 10^6$ | $2.1 \times 10^{-2}$ | $1.31 \times 10^4$ |
| 8.58 | 624 | $4.0 \times 10^5$ | $5.5 \times 10^{-3}$ | $1.37 \times 10^4$ |
| 9.27 | 222 | $2.5 \times 10^5$ | $3.7 \times 10^{-3}$ | $1.48 \times 10^4$ |
| 9.57 | 454 | $1.1 \times 10^6$ | $1.7 \times 10^{-2}$ | $1.55 \times 10^4$ |
| 8.10 | 718 | $1.3 \times 10^6$ | $2.4 \times 10^{-2}$ | $1.85 \times 10^4$ |
| 8.24 | 878 | $1.6 \times 10^6$ | $3.1 \times 10^{-2}$ | $1.94 \times 10^4$ |
| 9.9 | 454 | $7.3 \times 10^5$ | $1.5 \times 10^{-2}$ | $2.05 \times 10^4$ |
| 4.5 | 530 | $9.3 \times 10^5$ | $3.0 \times 10^{-2}$ | $3.25 \times 10^4$ |

The asterisks next to the $K_D$ results for mAbs 9.5, 9.58, and 9.47 indicate that these $K_D$'s may not be as reliable as the other $K_D$s owing to the poor fit of the sensorgrams of these mAbs to a 1:1 interaction model.

Example 6

Cynomolgus IL-1β Low Resolution Biacore Screen of 20 Monoclonal Antibody Hybridoma Cell Supernatants For this purpose, a high-density goat anti-human antibody surface over a CM5 Biacore chip was prepared using routine amine coupling. All of the hybridoma cell supernatants were diluted two-fold in HBS-P running buffer containing 100 μg/ml BSA and 10 mg/mL carboxymethyldextran. Each mAb was captured on a separate surface using a 120-second contact time, and a 5-minute wash for stabilization of the mAb baseline.

Cynomolgus monkey IL-1β was injected at 117 nM at 25° C. over all surfaces for 90 seconds, followed by a 5-minute dissociation. Double-referenced binding data was prepared by subtracting the signal from a control flow cell and subtracting the baseline drift of a buffer injection just prior to the IL-1β injection. Data were fit globally to a 1:1 interaction model to determine the binding kinetics. The kinetic analysis results of cynomolgus IL-1β binding at 25° C. are listed in Table 14, below. The mAbs are ranked from highest to lowest affinity.

TABLE 14

| Sample | Amt. Captured (RU) | $k_a$ (M$^{-1}$s$^{-1}$) | $k_d$ (s$^{-1}$) | $K_D$ (nM) |
|---|---|---|---|---|
| 9.19 | 486 | $2.6 \times 10^5$ | $1.2 \times 10^{-4}$ | 0.5 |
| 6.33 | 421 | $2.3 \times 10^5$ | $1.8 \times 10^{-4}$ | 0.8 |
| 9.11 | 583 | $3.3 \times 10^5$ | $2.7 \times 10^{-4}$ | 0.8 |
| 8.18 | 255 | $1.1 \times 10^5$ | $9.2 \times 10^{-5}$ | 0.8 |
| 9.5 | 220 | $2.2 \times 10^5$ | $2.3 \times 10^{-4}$ | 1.0 |
| 6.26 | 564 | $2.7 \times 10^5$ | $3.1 \times 10^{-4}$ | 1.1 |
| 9.26 | 263 | $1.5 \times 10^5$ | $2.0 \times 10^{-4}$ | 1.3 |
| 9.54 | 284 | $1.8 \times 10^5$ | $3.5 \times 10^{-4}$ | 1.9 |
| 8.50 | 384 | $4.7 \times 10^5$ | $1.2 \times 10^{-3}$ | 2.5 |
| 8.59 | 63 | $4.6 \times 10^5$ | $1.5 \times 10^{-3}$ | 3.3 |
| 5.36 | 771 | $2.1 \times 10^5$ | $7.2 \times 10^{-4}$ | 3.4 |
| 9.2 | 423 | $3.1 \times 10^5$ | $1.4 \times 10^{-3}$ | 4.5* |
| 5.5 | 438 | $2.4 \times 10^5$ | $1.1 \times 10^{-3}$ | 4.6 |
| 9.74 | 28 | $9.0 \times 10^4$ | $4.3 \times 10^{-4}$ | 4.8 |
| 9.31 | 442 | $3.0 \times 10^5$ | $1.5 \times 10^{-3}$ | 5.0 |
| 8.6 | 262 | $1.6 \times 10^5$ | $8.5 \times 10^{-4}$ | 5.3 |
| 4.20 | 115 | $8.0 \times 10^5$ | $5.0 \times 10^{-3}$ | 6.3 |
| 6.7 | 41 | $3.2 \times 10^5$ | $2.5 \times 10^{-3}$ | 7.8 |
| 6.20 | 635 | $2.5 \times 10^5$ | $6.1 \times 10^{-3}$ | 24.4 |
| 6.34 | 772 | $3.2 \times 10^5$ | $1.8 \times 10^{-2}$ | 56.2 |

Example 7

Characterization of 24 IL-1β Antibodies

The binding and neutralization characteristics of some of these antibodies were determined and are summarized in Table 15. The method for determining the characteristics are discussed in greater detail in Example 4, above. The amino acid and nucleic acid sequences for each of the antibodies were determined by standard means and is provided in the sequence listing provided herewith.

TABLE 15

| Antibody ID | ka (M−1s−1) | kd (s−1) | KD (pM) | KD (pM) | Neutralization (% IL-6 Production) | | |
|---|---|---|---|---|---|---|---|
| | Medium Resolution | | | Low Res | 1:5 dilut. | 1:10 dilut. | 1:20 dilut. |
| 9.19 | 6.40E+05 | 4.00E−05 | 63 | 268 | 5 | 10 | 15 |
| 9.5 | 2.60E+06 | 3.50E−04 | 130* | 1640* | 0 | 0 | 0 |
| 9.11 | 1.60E+06 | 2.30E−04 | 140 | 290 | 4 | 3 | 10 |
| 6.33 | 9.70E+05 | 1.40E−04 | 140 | 320 | 13 | 22 | 22 |
| 9.54 | 2.50E+06 | 3.50E−04 | 140 | 370 | 5 | 21 | 36 |
| 6.20 | 1.50E+06 | 2.60E−04 | 170 | 441 | 4 | 6 | 11 |
| 5.5 | 3.10E+06 | 5.70E−04 | 180 | 278 | 1 | 3 | 6 |
| 6.26 | 1.90E+06 | 3.80E−04 | 200 | 478 | 9 | 8 | 22 |
| 9.100 | 5.30E+05 | 1.50E−04 | 280 | 279 | 39 | 37 | 36 |
| 9.2 | 1.20E+06 | 3.50E−04 | 290 | 747 | 4 | 8 | 16 |
| 6.7 | 1.30E+06 | 4.20E−04 | 320 | 350 | 0 | 17 | 22 |
| 8.18 | 4.90E+05 | 2.20E−04 | 450 | 629 | 2 | 3 | 9 |
| 5.36 | 1.00E+06 | 5.80E−04 | 580 | 712 | 6 | 8 | 18 |
| 8.6 | 6.60E+05 | 5.40E−04 | 820 | 1230 | 6 | 8 | 23 |
| 6.34 | N.D. | N.D. | N.D. | 753 | 10 | 7 | 20 |
| 9.26 | N.D. | N.D. | N.D. | 854 | 12 | 27 | 27 |
| 9.31 | N.D. | N.D. | N.D. | 5760 | 6 | 23 | 13 |
| 9.74 | N.D. | N.D. | N.D. | 2140 | 5 | 24 | 28 |
| 9.56 | N.D. | N.D. | N.D. | 533 | 35 | 39 | 76 |
| 5.12 | N.D. | N.D. | N.D. | 559 | 29 | 48 | 62 |
| 9.22 | N.D. | N.D. | N.D. | 611 | 16 | 24 | 51 |
| 5.25 | N.D. | N.D. | N.D. | 870 | 30 | 36 | 39 |
| 9.47 | N.D. | N.D. | N.D. | 909 | 10 | 47 | 86 |
| 9.85 | N.D. | N.D. | N.D. | 1034 | 24 | 63 | 80 |

*complex kinetics

Example 8

Human IL-1β High Resolution Biacore Screen of 6 Purified Monoclonal Antibodies Each of six purified mAbs (9.5.2, 5.5.1, 8.18.1, 6.20.1, 6.33.1, and 9.19.1) were amine coupled on a different flow cell surface of a CM5 Biacore chip and tested for their binding affinity to human IL-1β. All mAbs were diluted into 10 mM sodium acetate, pH 4.0 for immobilization. The running buffer and sample preparation buffer for all experiments were degassed HBS-P containing 100 µg/mL BSA. All experiments were run at 23° C. with a flow rate of 100 µL/min. With the exception of mAb 9.5.2, serially diluted (2-fold) IL-1β samples were randomly injected in triplicate for 90 seconds with several buffer injections interspersed for double referencing. Regeneration conditions and dissociation times varied (see below). A Biacore 2000 biosensor instrument was used for all high resolution experiments.

MAb 9.5.2:

A CM5 chip was prepared with mAb 9.5.2 covalently immobilized using standard amine coupling chemistry on flow cells 1, 2, and 4 with flow cell 3 serving as a control (immobilization levels for 9.5.2 on Fc1, 2, and 4 were 1650, 1370, and 652 RU, respectively). An IL-1β solution with a final concentration of 55 pM (250 mL) was prepared using glass serological pipettes and volumetric glassware. IL-1β at a concentration of 55 pM was injected directly from the buffer pump reservoir at 100 µL/min in cycle 1 for 18.1 hrs followed by pumping running buffer (HBS-P, 100 µg/ml BSA, pH 7.4) to follow the dissociation reaction for 24.8 hours across all four flow cells. Before the antigen injection was started, the sensorgram was run for one hour by flowing running buffer in order to establish a pre-injection baseline. Before the next cycle the surface was regenerated with two 35 µl pulses of 146 mM phosphoric acid, pH ~1.5.

In the second Biacore cycle, running buffer was flowed as if an actual injection of IL-1β was taking place. Running buffer was flowed across all the surfaces for ~50 hours to simulate the time course of the association and dissociation phases for IL-1β performed in cycle 1 (1 hr for baseline stabilization, 18.1 hrs for association and 24.8 hours for dissociation). All data were processed in the program Scrubber and double-referenced (only one blank sensorgram, from cycle 2, was available for double referencing) and the data were fit in CLAMP 2000. When the sensorgrams from both flow cells 1 & 2 were fit globally using a 1:1 interaction model with a term for mass transport ($6.6 \times 10^8$ RU*M$^{-1}$S$^{-1}$) the binding parameters shown in Table 16 resulted.

This "long association and dissociation" Biacore methodology gives a $K_D$ for the IL-1β/mAb 9.5.2 interaction that is ~7.5-fold less tight than that observed with KinExA technology (see Example 9 below). This discrepancy is most likely owing to the fact that concentrations near the true $K_D$ of approximately 200 fM cannot be flowed across the mAb surface because no signal can be observed at this low of an IL-1β concentration.

MAb 5.5.1:

MAb 5.5.1 was diluted to 14 µg/mL to immobilize 762 RU on one flow cell. The serially diluted IL-1β concentration range was 4.9-0.31 nM. Dissociation data was recorded over 15 minutes. The surface was regenerated after each cycle with a 21 second pulse of 10 mM glycine-HCl, pH 2.5, followed by a 15 second injection of the same glycine solution.

MAb 6.33.1:

MAb 6.33.1 was diluted to 7.5 µg/mL to immobilize 694 RU on one flow cell. The serially diluted IL-1β concentration range was 29.4-0.92 nM. Dissociation data was recorded over 20 minutes. The surface was regenerated after each cycle with two 21 second pulses of 10 mM glycine-HCl, pH 2.0.

MAb 9.19.1:

MAb 9.19.1 was diluted to 12.6 µg/mL to immobilize 977, 763, and 817 RU on three different flow cells, respectively.

The IL-1β concentration range was 19.6-0.61 nM. Dissociation data was recorded over 15 minutes. The surfaces were regenerated after each cycle with one 21 second pulse of 10 mM glycine-HCl, pH 2.0, and one 6 second injection of 146 mM phosphoric acid, pH 1.5.

MAb 6.20.1:

MAb 6.20.1 was diluted to 17.6 μg/mL to immobilize 907 RU on one flow cell. The IL-1β concentration range was 29.4-0.92 nM. Dissociation data was recorded over 20 minutes. The surface was regenerated after each cycle with one 12 second pulse of 10 mM glycine-HCl, pH 2.0.

MAb 8.18.1:

MAb 8.18.1 was diluted to 18.5 μg/mL to immobilize 572 RU on one flow cell. The IL-1β concentration range was 58.7-0.92 nM. Dissociation data was recorded over 20 minutes. The surface was regenerated after each cycle with one 12 second pulse of 10 mM glycine-HCl, pH 2.0.

The data for all six mAbs were globally fit to a 1:1 interaction model with mass transport using CLAMP. The resulting binding constants are shown in Table 16 below. The asterisk next to the results listed for mAb 6.20.1 indicates this data showed complex kinetics.

TABLE 16

| Sample | $k_a$ (M$^{-1}$s$^{-1}$) | $k_d$ (s$^{-1}$) | $K_D$ (pM) |
| --- | --- | --- | --- |
| 9.5.2  | $7.1 \times 10^5$    | $1.1 \times 10^{-6}$    | 1.5  |
| 5.5.1  | $1.57 \times 10^7$   | $7.04 \times 10^{-4}$   | 44.7 |
| 6.33.1 | $1.10 \times 10^6$   | $2.59 \times 10^{-4}$   | 236  |
| 9.19.1 | $7.27 \times 10^5$   | $1.90 \times 10^{-4}$   | 262  |
| 6.20.1 | $1.24 \times 10^{6*}$ | $3.63 \times 10^{-4*}$ | 293* |
| 8.18.1 | $4.85 \times 10^5$   | $1.88 \times 10^{-4}$   | 388  |

Example 9

High Resolution Binding Analysis by KinExA (Kinetic Exclusion Assay)

Human IL-1β High Resolution Binding Analysis by KinExA (Kinetic Exclusion Assay) for Purified MAb 9.5.2 (IgG4 Isotype)

In addition to Biacore measurements, the $K_D$ of mAb 9.5.2 (IgG4 isotype) binding to human IL-1β was determined using KinExA technology. For this purpose, a KinExA 3000 instrument was utilized. First, 50 mg of azlactone beads were coupled with IL-1β (~34 μg) in 50 mM sodium carbonate buffer, pH 9.0 overnight at 4° C. Second, after conjugation of IL-1β to the beads, the beads were centrifuged and washed once with blocking buffer (1 M Tris buffer, pH 8.3, 10 mg/ml BSA) and centrifuged again. The beads were then incubated in blocking buffer for one to two hours at ~22° C. in order to block any remaining reactive azlactone groups present on the surface of the beads. After blocking, the beads were transferred to a standard KinExA bead vial and placed on the instrument.

$K_D$-controlled titration: Twelve solutions containing a nominal mAb binding site concentration of 667 fM were titrated with increasing concentrations of IL-1β in hepes buffered saline, 0.005% polysorbate 20 (P-20), 100 ug/ml bovine serum albumin, BSA, pH 7.4 (HBS-P buffer). Each solution had a total volume of 50 ml and was allowed to equilibrate for 8 days at ~22° C. The titration solutions were prepared using volumetric glassware and the IL-1β concentrations varied from 99.5 pM to 1.94 fM. The instrument method used for the analysis of these solutions consisted of a bead packing step in which the beads were packed into a glass capillary, and the equilibrated solutions were flowed through the bead column at 0.25 ml/min for 80 min (20 ml) in duplicate. Subsequently, a fluorescently labeled cy-5 goat anti-human (heavy+light chain (H+L) specific) polyclonal antibody at 13.6 nM was flowed through the bead pack for 2 min at 0.5 ml/min to label the free mAb binding site captured on the beads. The fluorescence emission from the bead pack was measured at 670 nm with excitation at 620 nm. The resulting fluorescence measurements were converted into % free mAb binding site versus total antigen concentration using the accompanying KinExA software package (version 1.0.3). The resulting $K_D$-controlled titration curve was fit with the KinExA software to a 1:1 equilibrium isotherm with a drift correction factor included. The value of the 9.5.2 antibody (IgG4) $K_D$ that fit the data optimally was 40 fM with low and high 95% confidence limits at 4.9 fM and 114 fM, respectively.

MAb-controlled titrations: Two mAb-controlled titrations were performed in a similar fashion to the $K_D$-controlled titration. Twelve solutions containing a nominal mAb binding site concentration of 5.33 pM (titration A) and 102 pM (titration B) were titrated with increasing concentrations of IL-1β in HBS-P buffer. Each solution had a total volume of 2.5 and 50 ml for titrations B and A, respectively. The IL-1β concentrations varied from 398 pM to 8 fM in both titrations. The solutions were allowed to equilibrate for ~1 day for titration B and ~8 days for titration A at room temperature before quantitation of free mAb binding site in each of the solutions on the KinExA 3000 instrument. The instrument method used for the analysis of these solutions consisted of a bead packing step in which the beads were packed into a glass capillary, the equilibrated solutions were flowed through the bead column at 0.25 ml/min for 2 min (0.5 ml) for titration B and for 40 min. (10 ml) for titration A in triplicate, and subsequently, a fluorescently labeled cy-5 goat anti-human (H+L specific) polyclonal antibody at 3.4 nM (for titrations A & B) was flowed through the bead pack for 2 min at 0.5 ml/min. The fluorescence emission from the bead pack was measured as previously described above. The resulting fluorescence measurements were converted into % free mAb binding site versus total antigen concentration as described above and the mAb-controlled titration data were fit in a triple curve analysis (simultaneous fitting of both the $K_D$-controlled and the two mAb-controlled titration curves) to a 1:1 equilibrium isotherm with drift correction included. The fitted values for the $K_D$ and active mAb binding site concentration from the triple titration curve analysis yielded values of 181 fM (with low and high 95% confidence limits of 60.0 and 341 fM) and 6.33 pM (with low and high 95% confidence limits of 5.36 and 7.47 pM for titration A), respectively. The $K_D$, 181 fM, resulting from the triple curve analysis is more accurate than the fit from the single $K_D$-controlled titration curve since it comes from the more rigorous global analysis of three titration curves.

KinExA "Direct" Kinetic Method for Determination of $K_{ON}$

A "direct" kinetic methodology was used in order to determine the kinetic association rate constant, kon, of IL-1β binding to 9.5.2 (IgG4 isotype). Azlactone beads were prepared as described above for the equilibrium titrations. All IL-1β and mAb 9.5.2 solutions were prepared in degassed HBS-P buffer. A 25 ml solution containing IL-1β at an initial concentration of 238.8 pM was mixed rapidly with a 25 ml solution of 9.5.2 initially at 200 pM mAb binding site to make a 50 ml solution with final concentrations of IL-1β and mAb 9.5.2 of 119.4 pM and 99.9 pM binding site, respectively. For quantitation of free mAb as a function of time, 0.5 ml of the final solution above was flowed through the bead pack at a flow rate of 0.25 ml/min for 2 min (1 mL) and then detected using a 2 min. flow through of a 3.4 nM fluorescently labeled cy-5 labeled goat anti-human pAb (H+L). The first time point in the exponential decay was at 464 sec and after that a point was collected every 804 sec (~13.5 min) as equilibrium was approached over 1 hr. The resulting monophasic exponential curve was fit in the provided KinExA software (version 1.0.3) to a single exponential function that describes a 1:1 interaction. The resultant kon=3.4×10⁶ M−1s−1 with a 95% confidence interval of 2.8-4.0×10⁶ M−1s−1. By multiplying konX KD the dissociation rate constant, koff, was calculated as 6.1×10−7 s−1.

Human IL-1β High Resolution Binding Analysis BY KinExA (Kinetic Exclusion Assay) for Purified mAb 9.5.2 (IgG2 Isotype)

The $K_D$ of mAb 9.5.2 binding to human IL-1β was also determined using KinExA technology a 9.5.2 monoclonal antibody that was class-switched from an IgG4 isotype to an IgG2 isotype. Methods for class switching antibodies are known in the art and discussed in Example 10 below. First, 50 mg of azlactone beads were coupled with IL-1β (~34 μg) in 50 mM sodium carbonate buffer, pH 9.0 overnight at 4° C. Second, after conjugation of IL-1β to the beads, the beads were centrifuged and washed once with blocking buffer (1 M Tris buffer, pH 8.3, 10 mg/ml BSA) and centrifuged again, and then incubated in blocking buffer for one to two hours at ~22° C. in order to block any remaining reactive azlactone groups present on the surface of the beads. After blocking, the beads were transferred to a standard KinExA bead vial and placed on the instrument.

$K_D$-controlled titration: Twelve solutions containing a nominal mAb binding site concentration of 680 fM were titrated with increasing concentrations of IL-1β in HBS-P buffer. Each solution had a total volume of 50 ml and was allowed to equilibrate for 8 days at ~22° C. The titration solutions were prepared using volumetric glassware and the IL-1β concentrations varied from 99.5 pM to 1.94 fM. The instrument method used for the analysis of these solutions consisted of a bead packing step in which the beads were packed into a glass capillary, and the equilibrated solutions were flowed through the bead column at 0.25 ml/min for 80 min (20 ml) in duplicate. Subsequently, a fluorescently labeled cy-5 goat anti-human (H+L specific) polyclonal antibody at 13.6 nM was flowed through the bead pack for 2 min at 0.5 ml/min to label the free mAb binding site captured on the beads. The fluorescence emission from the bead pack was measured as previously described. The resulting fluorescence measurements were converted into % free mAb binding site versus total antigen concentration using the accompanying KinExA software package (version 1.0.3). The resulting $K_D$-controlled titration curve was fit with the KinExA software to a 1:1 equilibrium isotherm with a drift correction factor included. The value of the $K_D$ that fit the data optimally was 41 fM with low and high 95% confidence limits at 11 fM and 83 fM, respectively.

MAb-controlled titrations: Two mAb-controlled titrations were performed in a similar fashion to the $K_D$-controlled titration. Twelve solutions containing a nominal mAb binding site concentration of 4.98 pM (titration A) and 102 pM (titration B) were titrated with increasing concentrations of IL-1β in HBS-P buffer. Each solution had a total volume of 2.5 and 50 ml for titrations B and A, respectively. The IL-1β concentrations varied from 398 pM to 8 fM in both titrations. The solutions were allowed to equilibrate for 18 hours for titration B and ~8 days for titration A at room temperature before quantitation of free mAb binding site in each of the solutions on the KinExA 3000 instrument. The instrument method used for the analysis of these solutions consisted of a bead packing step in which the beads were packed into a glass capillary, the equilibrated solutions were flowed through the bead column at 0.25 ml/min for 2 min (0.5 ml) for titration B and for 40 min. (10 ml) for titration A in triplicate, and subsequently, a fluorescently labeled cy-5 goat anti-human (H+L specific) polyclonal antibody at 3.4 nM (for titrations A & B) was flowed through the bead pack for 2 min at 0.5 ml/min. The fluorescence emission was measured as previously described. The resulting fluorescence measurements were converted into % free mAb binding site versus total antigen concentration as described above and the mAb-controlled titration data were fit in a triple curve analysis (simultaneous fitting of both the $K_D$-controlled and the two mAb-controlled titration curves) to a 1:1 equilibrium isotherm with drift correction included. The fitted values for the $K_D$ and active mAb binding site concentration from the triple titration curve analysis yielded values of 204 fM (with low and high 95% confidence limits of 83 and 369 fM) and 81.7 pM, respectively (with low and high 95% confidence limits of 67.1 and 104 pM for titration B). The $K_D$, 204 fM, resulting from the triple curve analysis is more accurate than the fit from the single $K_D$-controlled titration curve since it comes from the more rigorous global analysis of three titration curves.

Human IL-1β High Resolution Binding Analysis by KinExA (Kinetic Exclusion Assay) for Purified mAb 5.5.1

The $K_D$ of mAb 5.5.1 binding to human IL-1β was determined using KinExA technology. Firstly, 50 mg of azlactone beads were coupled with IL-1β (~17 μg) in 50 mM sodium carbonate buffer, pH 9.0 overnight at 4° C. Secondly, after conjugation of IL-1β to the beads, the beads were centrifuged and washed once with blocking buffer (1 M Tris buffer, pH 8.3, 10 mg/ml BSA) and centrifuged again, and then incubated in blocking buffer for one to two hours at ~22° C. in order to block any remaining reactive azlactone groups present on the surface of the beads. After blocking, the beads were transferred to a standard KinExA bead vial and placed on the instrument.

$K_D$-controlled titration: Twelve solutions containing a nominal mAb binding site concentration of 21.3 pM were titrated with increasing concentrations of IL-1β in HBS-P buffer. Each solution had a total volume of 20 ml and was allowed to equilibrate for 1 day at ~23° C. The titration solutions were prepared using volumetric glassware and the IL-1β concentrations varied from 4.97 nM to 97 fM. The instrument method used for the analysis of these solutions consisted of a bead packing step in which the beads were packed into a glass capillary, and the equilibrated solutions were flowed through the bead column at 0.25 ml/min for 20 min (5 ml) in triplicate. Subsequently, a fluorescently labeled cy-5 goat anti-human (H+L) polyclonal antibody at 3.4 nM was flowed through the bead pack for 2 min at 0.5 ml/min to label the free mAb binding site captured on the beads. The fluorescence emission from the bead pack was measured as stated previously. The resulting fluorescence measurements were converted into % free mAb binding site versus total antigen concentration as standardly done with the accompanying KinExA software package (version 1.0.3). The resulting $K_D$-controlled titration curve was fit with the KinExA software to a 1:1 equilibrium isotherm with a drift correction factor included. The value of the $K_D$ that fit the data optimally was 19 pM with low and high 95% confidence limits at 16 pM and 23 pM, respectively.

MAb-controlled titration: The mAb-controlled titration was performed in a similar fashion to the $K_D$-controlled titration. Twelve solutions containing a nominal mAb binding site concentration of 511 pM were titrated with increasing concentrations of IL-1β in HBS-P. Each solution had a total volume of 2 mL. The IL-1β concentrations varied from 4.97 nM to 97 fM as in the $K_D$-controlled titration. The solutions were allowed to equilibrate for 5 hours before quantitation of free mAb binding site in triplicate for each of the solutions on the KinExA 3000 instrument. The instrument method used for the analysis of these solutions consisted of a bead packing step in which the beads were packed into a glass capillary, the equilibrated solutions were flowed through the bead column at 0.25 ml/min for 1 min (0.25 ml), and subsequently, a fluorescently labeled cy-5 goat anti-human (H+L) polyclonal antibody at 3.4 nM was flowed through the bead pack for 2 min at 0.5 ml/min. The fluorescence emission from the bead pack was measured as described previously. The resulting fluorescence measurements were converted into % free mAb binding site versus total antigen concentration as described above and the mAb-controlled titration data were fit in a dual curve analysis (simultaneous fitting of both the $K_D$-controlled and mAb-controlled titration curves) to a 1:1 equilibrium isotherm with drift correction included. The fitted values for the $K_D$ and active mAb binding site concentration from the dual titration curve analysis yielded values of 20 pM (with low and high 95% confidence limits of 18 and 24 pM) and 13 pM (with low and high 95% confidence limits of 11 and 14 for the $K_D$-controlled curve), respectively. As always, the $K_D$ resulting from the dual curve analysis is more accurate than the fit from the single $K_D$-controlled titration curve analysis.

Cynomolgus IL-1β High Resolution Binding Analysis by KinExA (Kinetic Exclusion Assay) for purified mAb 9.5.2 (IGG$_2$ Isotype)

The $K_D$ of mAb 9.5.2 binding to cynomolgus IL-1β was determined using KinExA technology. First, 50 mg of azlactone beads were coupled with IL-1β (~17 μg) in 50 mM sodium carbonate buffer, pH 9.0 overnight at 4° C. Second, after conjugation of IL-1β to the beads, the beads were centrifuged and washed once with blocking buffer (1 M Tris buffer, pH 8.3, 10 mg/ml BSA) and centrifuged again, and then incubated in blocking buffer for one to two hours at ~23° C. in order to block any remaining reactive azlactone groups present on the surface of the beads. After blocking, the beads were transferred to a standard KinExA bead vial and placed on the instrument.

$K_D$-controlled titration: Twelve solutions containing a nominal mAb binding site concentration of 4.98 pM were titrated with increasing concentrations of cynomolgus IL-1β in HBS-P buffer. Each solution had a total volume of 25 ml and was allowed to equilibrate for 3 days at ~23° C. The titration solutions were prepared using volumetric glassware and the cynomolgus IL-1β concentrations varied from 12.0 nM to 234 fM. The instrument method used for the analysis of these solutions consisted of a bead packing step in which the beads were packed into a glass capillary, and the equilibrated solutions were flowed through the bead column at 0.25 ml/min for 20 min (5 ml) in triplicate. Subsequently, a fluorescently labeled cy-5 goat anti-human (H+L specific) polyclonal antibody at 3.4 nM was flowed through the bead pack for 2 min at 0.5 ml/min to label the free mAb binding site captured on the beads. The fluorescence emission from the bead pack was measured as before. The resulting fluorescence measurements were converted into % free mAb binding site versus total antigen concentration with the accompanying KinExA software package (version 1.0.3). The resulting $K_D$-controlled titration curve was fit with the KinExA software to a 1:1 equilibrium isotherm with a drift correction factor included. The value of the $K_D$ that fit the data optimally was 14 pM with low and high 95% confidence limits at 12 pM and 17 pM, respectively.

MAb-controlled titration: The mAb-controlled titration was performed in a similar fashion to the $K_D$-controlled titration. Twelve solutions containing a nominal mAb binding site concentration of 997 pM were titrated with increasing concentrations of cynomolgus IL-1β in HBS-P. Each solution had a total volume of 1.5 mL. The cynomolgus IL-1β concentrations varied from 98.6 nM to 1.93 pM. The solutions were allowed to equilibrate for 2 hours before quantitation of free mAb binding site in triplicate for each of the solutions on the KinExA 3000 instrument. The instrument method used for the analysis of these solutions consisted of a bead packing step in which the beads were packed into a glass capillary, the equilibrated solutions were flowed through the bead column at 0.25 ml/min for 1.2 min (0.300 ml) in triplicate, and subsequently, a fluorescently labeled cy-5 goat anti-human (H+L specific) polyclonal antibody at 1.4 nM was flowed through the bead pack for 2 min at 0.5 ml/min. The fluorescence emission from the bead pack was performed as previously described. The resulting fluorescence measurements were converted into % free mAb binding site versus total antigen concentration as described above and the mAb-controlled titration data was fit in a dual curve analysis (simultaneous fitting of both the $K_D$-controlled and mAb-controlled titration curves) to a 1:1 equilibrium isotherm with drift correction included. The fitted values for the $K_D$ and active mAb binding site concentration from the dual titration curve analysis yielded values of 13 pM (with low and high 95% confidence limits of 11 and 16 pM) and 2.00 mM (with low and high 95% confidence limits of 1.8 and 2.2 for the mAb-controlled curve), respectively. As always, the $K_D$ resulting from the dual curve analysis is more accurate than the fit from the single $K_D$-controlled titration curve analysis.

Example 10

Inhibition OF IL-1β-Induced IL-6 Production in MRC-5 Lung Fibroblast Cells by 16 Anti-IL-1β Clones The 16 Purified IL-1β antibodies were tested for potency in a MRC-5 assay. In addition, IgG1λ and IgG2λ versions of the 9.5.2 IgG4λ antibody were tested. The 9.5.2 IgG4λ antibody was class-switched in vitro to IgG1λ and IgG2λ using molecular biology techniques of ordinary skill in the art. Briefly, the 9.5.2 hybridoma was lysed and RT-PCR was performed using oligonucleotide primers to enable recovery of cDNAs for the complete VH and Vλ coding regions. The VH and Vλ cDNAs were molecularly cloned in a plasmid vector in the correct translational reading frame with genes for Cγ1 or Cγ2 for VH and Cλ for Vλ and sequenced to confirm identity with the original sequences. The vectors were then transfected into mammalian cells for recombinant production of intact IgGλ antibody. Antibody was purified from tissue culture supernatant by protein A chromatography.

Figure 2A:
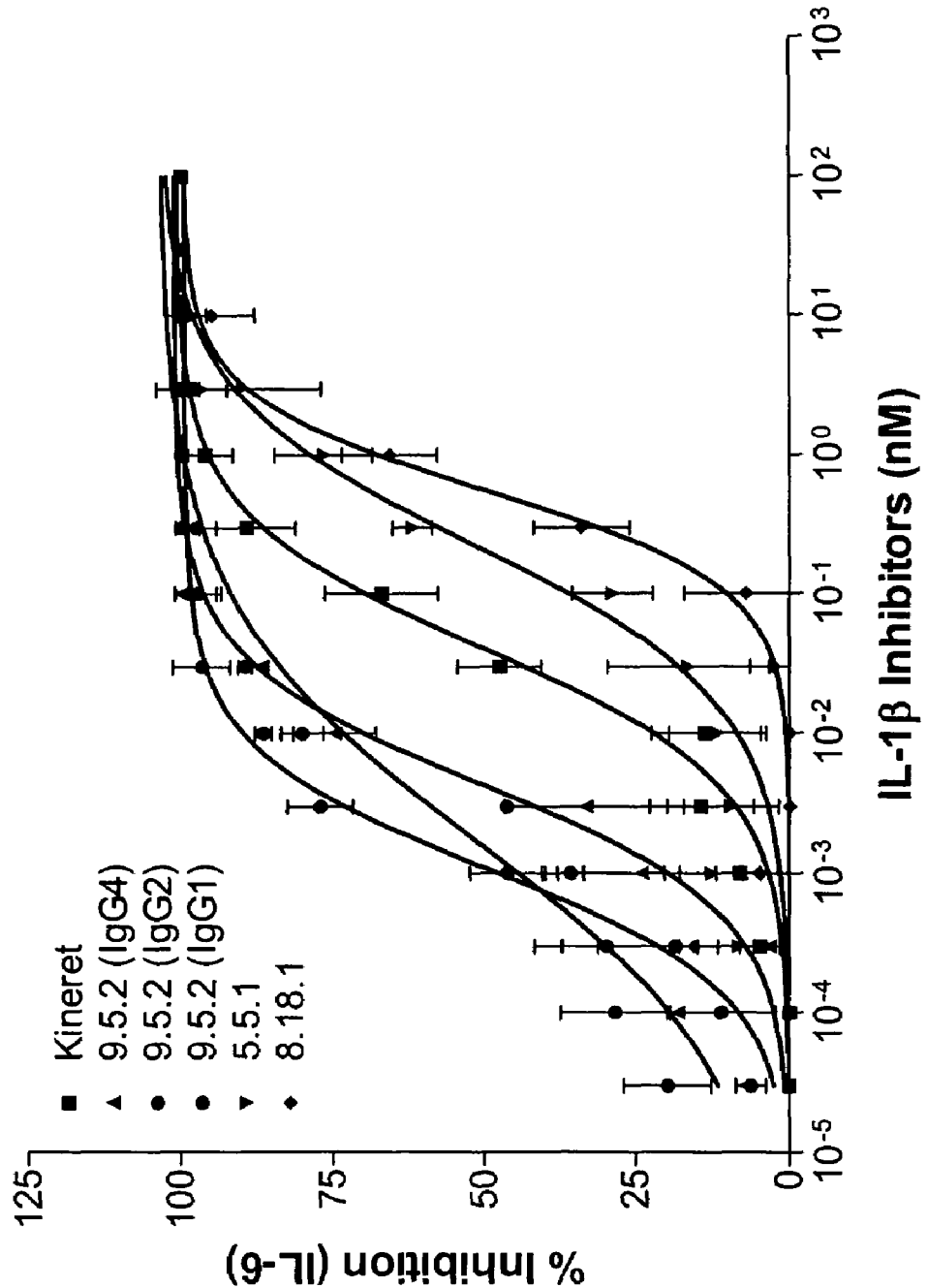
FIG. 2A is a graph depicting the percent inhibition of IL-1β-induced IL-6 production in MRC-5 cells for various antibodies.
Figure 2B:
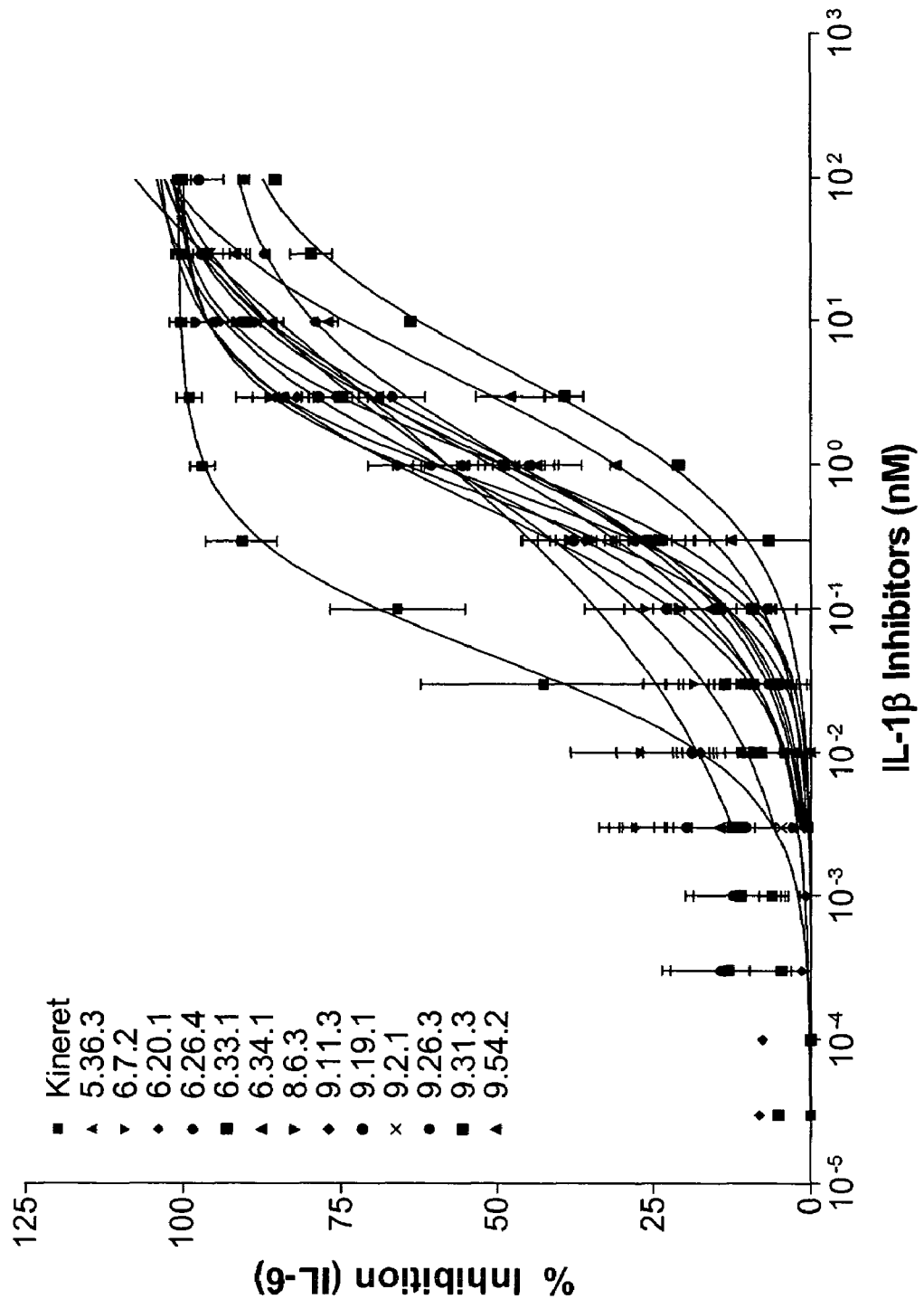
FIG. 2B is a graph depicting the percent inhibition of IL1β-induced IL-6 production in MRC-5 cells for various antibodies.

96 well flat-bottom plates were seeded with 5000 MRC-5 cells per well in 100 μl in MEM, 1% FBS. The plates were incubated for 18-20 hours at 37° C.+5% $CO_2$ to allow cell adherence. Media was removed from cells and replaced with 100 μl of IL-1β inhibitors or isotype matched controls (final concentrations of 300 nM to 0.00003 nM, titrated 1:3), and 100 μl of IL-1β (R&D Systems) (4 pM final concentration) in MEM, 1% FBS. The conditions of the assay were antigen limiting, e.g., the concentration of IL-1β exceeded the KD of 9.5.2 mAb. Wells containing no IL-1β and IL-1β alone were included as control wells. Plates were further incubated at 37° C.+5% $CO_2$ for 24 hours. Supernatants were collected and assayed for human IL-6 levels by Duoset ELISA (R&D Systems). Percent IL-6 production in each well was calculated compared to IL-1β alone control wells (100% production). Values were plotted as IL-1β inhibitor concentration vs. percent inhibition of IL-6 production and are displayed in FIG. 2A, FIG. 2B, and Table 17.

TABLE 17

|  | $EC_{50}$ (nM) |
| --- | --- |
| KINERET (Anakinra) | 0.077 ± 0.022 |
| 9.5.2 IgG4 | 0.004 ± 0.000 |
| 9.5.2 IgG2 | 0.004 ± 0.003 |
| 9.5.2 IgG1 | 0.001 ± 0.000 |
| 5.5.1 | 0.216 ± 0.015 |
| 8.18.1 | 0.536 ± 0.043 |
| 6.20.1 | 0.595 ± 0.216 |
| 6.26.4 | 0.591 ± 0.169 |
| 6.33.1 | 1.06 ± 0.478 |
| 8.6.3 | 1.587 ± 0.386 |
| 9.11.3 | 2.67 ± 1.165 |
| 9.19.1 | 2.911 1.586 |
| 5.36.3 | 3.154 ± 0.289 |
| 6.34.1 | 4.082 ± 0.181 |
| 9.2.1 | 5.468 ± 2.981 |
| 9.26.3 | 5.681 ± 1.558 |
| 6.7.2 | 6.57 ± 0.436 |
| 9.54.2 | 11.595 ± 0.813 |
| 9.31.3 | 14.29 ± 4.964 |

Example 11

Inhibition of IL-1β-Induced IL-8 in Human Whole Blood by 9.5.2, 5.5.1 and 8.18.1

Whole blood assays were performed to evaluate the effects of the 3 anti-IL-1βs selected in the MRC-5 assay on IL-1β-induced IL-8 production. Titrations of anti-IL-1β antibodies and isotype matched controls were prepared in RPMI-1640, 2 mM Glutamine, 1% Penicillin-streptomycin, and transferred to 96 well round-bottom plates. Human whole blood was collected in EDTA tubes, treated with 20 U/ml of heparin, and transferred to plates containing test samples and controls. A solution of human IL-1β (R&D Systems) was prepared in RPMI-1640, 2 mM Glutamine, 1% Penicillin-streptomycin, and added to the plates at a final concentration of 100 pM, which is antigen-limiting condition for mAb 9.5.2. Wells containing no IL-1β and IL-1β alone were included as control wells. Anti-IL-1β test samples and isotype matched controls were at final concentrations of 100 nM to 0.0003 nM (titrated 1:3) within the plates. Plates were incubated for six hours at 37° C.+5% $CO_2$. Whole blood cells were lysed with 0.5% Triton X-100 (Sigma) and lysates were assayed for human IL-8 production by Duoset ELISA (R&D Systems).

Figure 3:
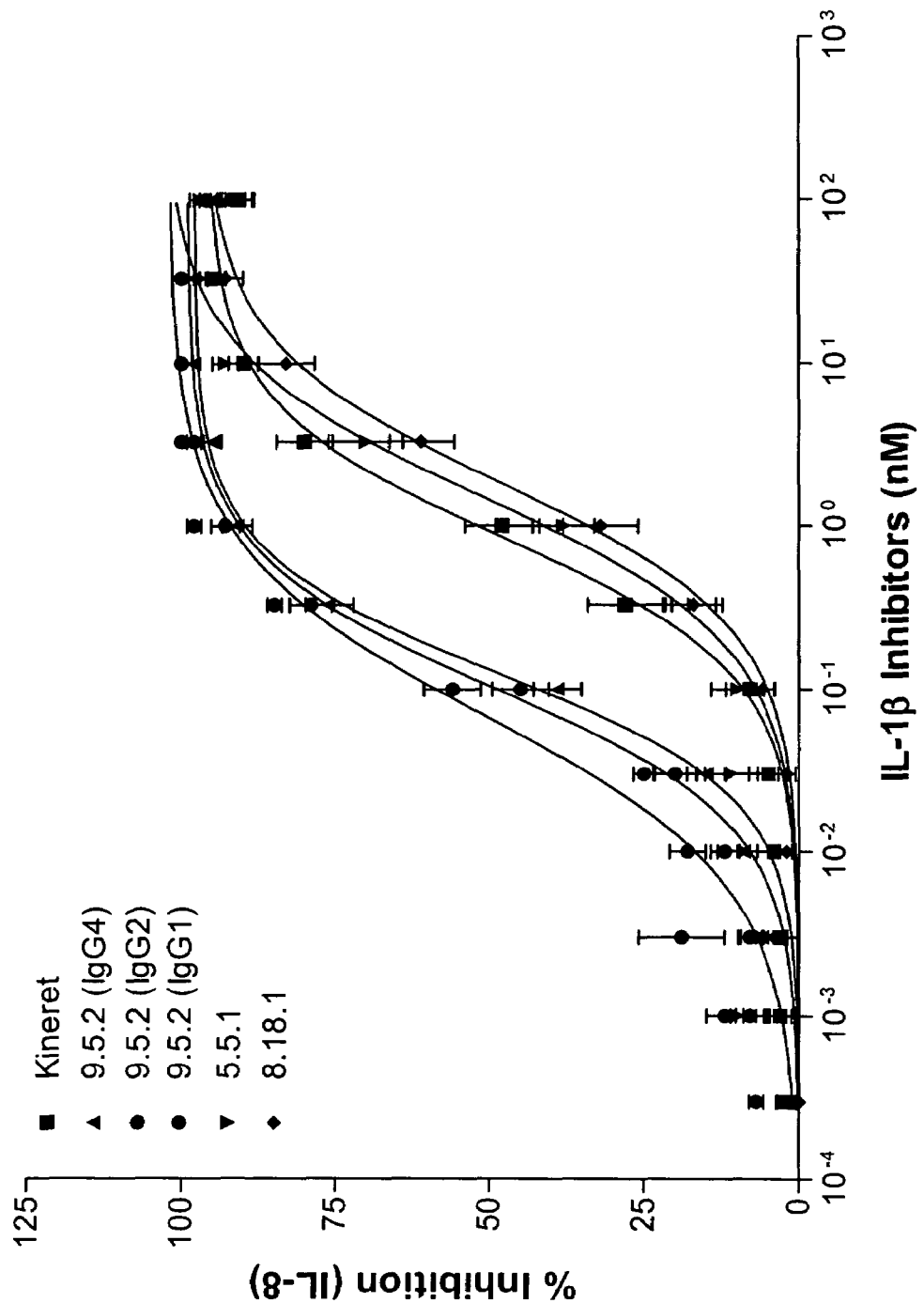
FIG. 3 is a graph depicting the percent inhibition of IL1β-induced IL-8 production in human whole blood for various antibodies.

Percent IL-8 production in each well was calculated compared to IL-1β alone control wells (100% production). Values were plotted as IL-1β inhibitor concentration vs. percent inhibition of IL-8 production and are shown in FIG. 3, and Table 18.

TABLE 18

|  | $EC_{50}$ (nM) |
| --- | --- |
| KINERET (anakinra) | 0.984 ± 0.223 |
| 9.5.2 IgG4 | 0.135 ± 0.017 |
| 9.5.2 IgG2 | 0.069 ± 0.003 |
| 9.5.2 IgG1 | 0.106 ± 0.017 |
| 5.5.1 | 1.667 ± 0.377 |
| 8.18.1 | 2.289 ± 0.453 |

Example 12

Inhibition of IL-1β Induced IL-6 Production in Mice by 9.5.2 and 5.5.1

Figure 4:
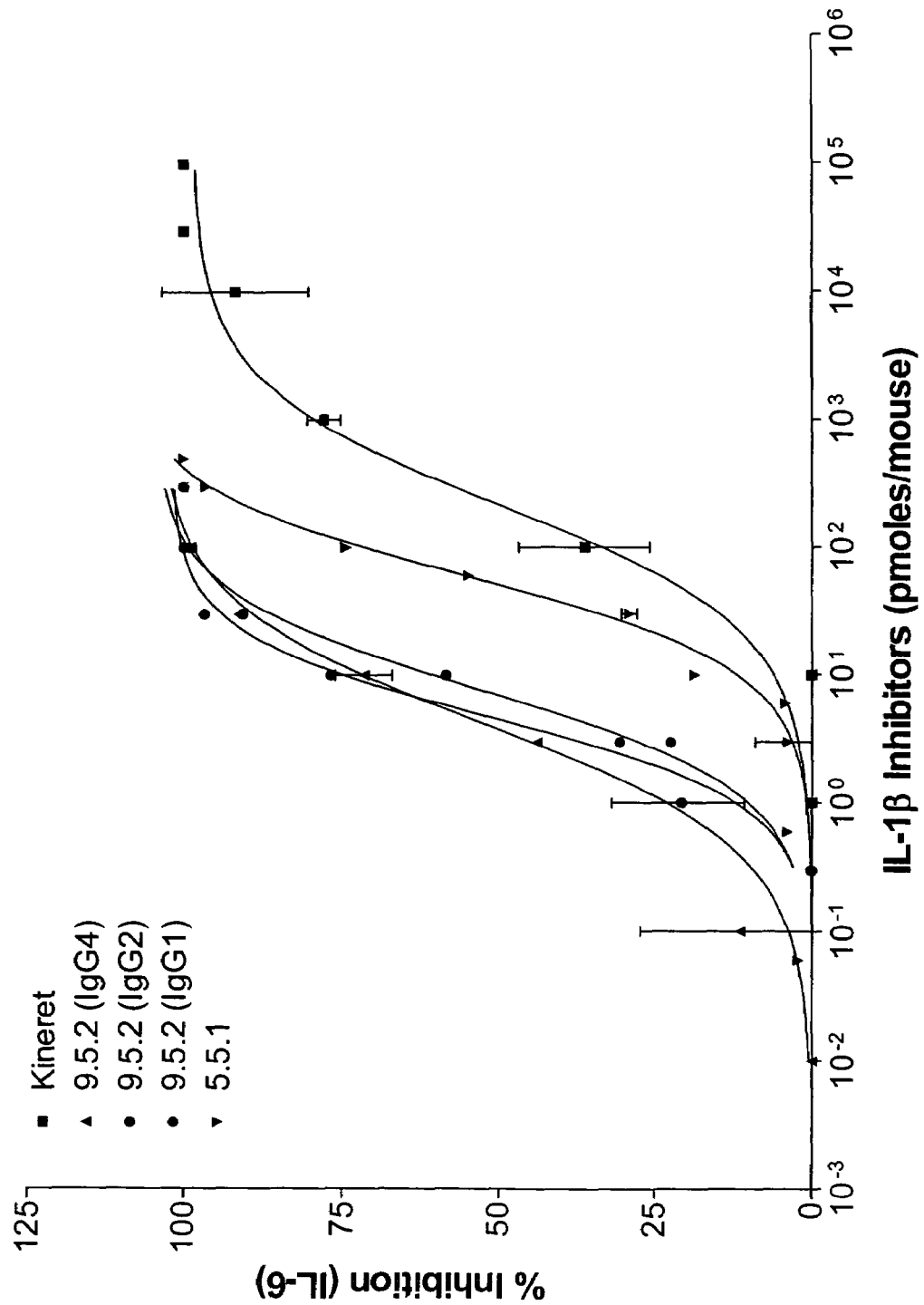
FIG. 4 is a graph depicting the percent inhibition of IL-6 production for Ab 9.5.2, Ab 5.5.1, and anakinra (KINERET™) in vivo. Upward triangles represent 9.5.2 IgG4, and downward triangles represent 5.5.1 IgG4.

To test the ability of IL-1, antibodies to inhibit IL-1β in vivo, IL-1β antibodies were used to block the production of IL-6 induced in mice by human IL-1β. IL-1β engenders many acute biological actions, including the induction of IL-6. Eight to 10 mice per group were used. As initially established in time-course experiments, injection of human IL-1β into mice caused a rapid rise in serum IL-6 levels that peaked at 2 hours after injection. Based on the results of other experiments aimed to define the dose and the route of administration of IL-1β, mice were injected intraperitoneally with 100 ng/mouse of human IL-1β. IL-6 levels were measured 2 hours after IL-1β administration using a commercial ELISA kit (R&D System). Dose-response experiments were performed by injecting IL-1β antibodies (0.01-75 μg/mouse, IV) at the same time as IL-1β (100 ng/mouse, IP). Control mice received 100 ng/mouse of saline before receiving IL-1β. The percent of IL-6 production in the treated mice were then compared to the control group (100% production). Values were plotted as IL-1β inhibitor dose (pmoles/mouse) vs. percent of IL-6 inhibition and are displayed in FIG. 4 and Table 19. In FIG. 4, the upward triangles are Ab 9.5.2, the downward triangles are Ab 5.5.1, and the squares denote KINERET (anakinra).

TABLE 19

| In Vivo Potency $EC_{50}$ (pmoles/mouse) | |
| --- | --- |
| Kineret | 222 ± 37 |
| 5.5.1 | 51 ± 1 |
| 9.5.2 IgG4 | 5 ± 3 |
| 9.5.2 IgG2 | 8 |
| 9.5.2 IgG1 | 5 |

As shown, the antibodies against IL-1β showed a dose dependent inhibition of IL-6, demonstrating that they were capable of neutralizing the activity of IL-1β in vivo.

Example 13

Determination of Canonical Classes of Antibodies

Chothia, et al. have described antibody structure in terms of "canonical classes" for the hypervariable regions of each immunoglobulin chain (*J Mol Biol.* 1987 Aug. 20; 196(4): 901-17). The atomic structures of the Fab and VL fragments of a variety of immunoglobulins were analyzed to determine the relationship between their amino acid sequences and the three-dimensional structures of their antigen binding sites. Chothia, et al. found that there were relatively few residues that, through their packing, hydrogen bonding or the ability to assume unusual phi, psi or omega conformations, were primarily responsible for the main-chain conformations of the hypervariable regions. These residues were found to occur at sites within the hypervariable regions and in the conserved β-sheet framework. By examining sequences of immunoglobulins having unknown structure, Chothia, et al. show that many immunoglobulins have hypervariable regions that are similar in size to one of the known structures and additionally contained identical residues at the sites responsible for the observed conformation.

Their discovery implied that these hypervariable regions have conformations close to those in the known structures. For five of the hypervariable regions, the repertoire of conformations appeared to be limited to a relatively small number of discrete structural classes. These commonly occurring main-chain conformations of the hypervariable regions were termed "canonical structures." Further work by Chothia, et al. (*Nature* 1989 Dec. 21-28; 342(6252):877-83) and others (Martin, et al. *J Mol Biol.* 1996 Nov. 15; 263(5):800-15) confirmed that there is a small repertoire of main-chain conformations for at least five of the six hypervariable regions of antibodies.

The CDRs of each antibody described above were analyzed to determine their canonical class. As is known, canonical classes have only been assigned for CDR1 and CDR2 of the antibody heavy chain, along with CDR1, CDR2 and CDR3 of the antibody light chain. The table below (Table 20) summarizes the results of the analysis. The Canonical Class data is in the form of *HCDR1-HCDR2-LCDR1-LCDR2-LCDR3, wherein "HCDR" refers to the heavy chain CDR and "LCDR" refers to the light chain CDR. Thus, for example, a canonical class of 1-3-2-1-5 refers to an antibody that has a HCDR1 that falls into canonical claiss 1, a HCDR2 that falls into canonical class 3, a LCDR1 that falls into canonical class 2, a LCDR2 that falls into canonical class 1, and a LCDR3 that falls into canonical class 5.

Assignments were made to a particular canonical class where there was 70% or greater identity of the amino acids in the antibody with the amino acids defined for each canonical class. The amino acids defined for each antibody can be found, for example, in the articles by Chothia, et al. referred to above. Table 20 and Table 21 report the canonical class data for each of the IL-1β antibodies. Where there was less than 70% identity, the canonical class assignment is marked with an asterisk ("*") to indicate that the best estimate of the proper canonical class was made, based on the length of each CDR and the totality of the data. Where there was no matching canonical class with the same CDR length, the canonical class assignment is marked with a letter s and a number, such as "s9", meaning the CDR is of size 9. Canonical classes noted with 9F, 10A, and 10B represent new structure examples of size 9, 10, and 10B respectively. There is no established canonical class number for these structure examples yet.

TABLE 20

| Antibody (sorted) | H1-H2-L1-L2-L3 | H3length |
|---|---|---|
| 4_20_1 | 1-3-2-1-1 | 9 |
| 5_36_1 | 3-s18-4-1-1 | 16 |
| 5_5_1 | 1-3-6-1-10B* | 10 |
| 6_20_1 | 1-2-9-1-9F* | 9 |
| 6_26_1 | 3-1-9*-1-9F | 14 |
| 6_33_1 | 1-3-6-1-10B* | 10 |
| 6_34_1 | 1-2-9-1-9F* | 9 |
| 6_7_1 | 1-2-9-1-9F* | 9 |
| 8_18_1 | 3-1-9-1-10A* | 10 |

TABLE 20-continued

| Antibody (sorted) | H1-H2-L1-L2-L3 | H3length |
|---|---|---|
| 8_50_1 | 1-1-9-1-5* | 13 |
| 8_59_1 | 1-3-8*-1-1 | 10 |
| 8_6_1 | 3-1-9-1-10A* | 10 |
| 9_11_1 | 1-3-6-1-10B* | 10 |
| 9_19_1 | 1-3-6-1-10B | 12 |
| 9_2_1 | 1-3-6-1-10B | 12 |
| 9_26_1 | 1-3-6-1-10B | 12 |
| 9_31_1 | 1-3-9-1-5* | 13 |
| 9_5_2 | 1-4-9-1-s9 | 17 |
| 9_54_1 | 1-3-9-1-5* | 17 |

TABLE 21

| Antibody | H1-H2-L1-L2-L3 (sorted) | H3length |
|---|---|---|
| 8_50_1 | 1-1-9-1-5* | 13 |
| 6_20_1 | 1-2-9-1-9F* | 9 |
| 6_34_1 | 1-2-9-1-9F* | 9 |
| 6_7_1 | 1-2-9-1-9F* | 9 |
| 4_20_1 | 1-3-2-1-1 | 9 |
| 9_19_1 | 1-3-6-1-10B | 12 |
| 9_2_1 | 1-3-6-1-10B | 12 |
| 9_26_1 | 1-3-6-1-10B | 12 |
| 5_5_1 | 1-3-6-1-10B* | 10 |
| 6_33_1 | 1-3-6-1-10B* | 10 |
| 9_11_1 | 1-3-6-1-10B* | 10 |
| 8_59_1 | 1-3-8*-1-1 | 10 |
| 9_54_1 | 1-3-9-1-5* | 17 |
| 9_31_1 | 1-3-9-1-5* | 13 |
| 9_5_2 | 1-4-9-1-s9 | 17 |
| 6_26_1 | 3-1-9*-1-9F | 14 |
| 8_18_1 | 3-1-9-1-10A* | 10 |
| 8_6_1 | 3-1-9-1-10A* | 10 |
| 5_36_1 | 3-s18-4-1-1 | 16 |

One candidate, 9.5.2, has canonical class 1-4-9-1-s9, and there is no other antibody sharing the same structure. The most commonly seen structure is 1-3-6-1-10B(*); 6 out of 21 sequences had this combination. The L3 canonical class here is 10B, meaning unclassified cluster example B for CDR length 10.

Table 22 is an analysis of the number of antibodies per class. The number of antibodies having the particular canonical class designated in the left column is shown in the right column.

TABLE 22

| H1-H2-L1-L2-L3 | Count |
|---|---|
| 1-1-9-1-5* | 1 |
| 1-2-9-1-9F* | 3 |
| 1-3-2-1-1 | 1 |
| 1-3-6-1-10B | 3 |
| 1-3-6-1-10B* | 3 |
| 1-3-8*1-1 | 1 |
| 1-3-9-1-5* | 2 |
| 1-4-9-1-s9 | 1 |
| 3-1-9*-1-9F | 1 |
| 3-1-9-1-10A* | 2 |
| 3-s18-4-1-1 | 1 |
| Total | 19 |

Example 14

High Affinity Fully Human IL-1β Monoclonal Antibody

This example compares the activity of antibodies described herein to anakinra, a known interleukin-1 receptor antagonist.

Characterization of the antibody from clone 9.5.2 revealed that the antibody displayed a high-affinity ($K_D$=204 fM for IgG2 and 181 fM for IgG4) to IL-1β. 9.5.2 was an IgG4 mAb that was class switched to IgG2 and IgG1 isotypes. The IL-1β epitope for this antibody resides in the N-terminal residues 1-34 of the IL-1β molecules. Arg4 was identified as a key residue for this antibody.

9.5.2 potently neutralized IL-1β in vitro as demonstrated through the inhibition of IL-1β-induced IL-6 production by MRC-5 cells and IL-8 production by whole blood (protocols as shown in the previous examples and results are shown in Table 23 below). In mice, 9.5.2 inhibited IL-1β-induced IL-6 production, as shown in Table 23. 9.5.2 displayed in vitro and in vivo potencies superior to anakinra (Table 23). Because the concentration of IL-1β used in the in vitro assays was antigen limiting ([IL-1β]>$K_D$), the actual potency can be higher. This example demonstrates that blockade of IL-1β with a mAb is a valid approach to the neutralization of IL-1 function and thus represents a therapeutically valid approach to inflammatory diseases.

TABLE 23

|  | In vitro Potency ($EC_{50}$ pM) | | In vivo Potency ($EC_{50}$ pmoles/mouse) |
| --- | --- | --- | --- |
|  | IL-6 (MRC-5) | IL-8 (Whole Blood) | IL-6 |
| 9.5.2 IgG4 | 4 ± 0 | 135 ± 17 | 5 ± 3 |
| 9.5.2 IgG2 | 4 ± 3 | 69 ± 3 | 8 |
| 9.5.2 IgG1 | 1 ± 0 | 106 ± 17 | 5 |
| Anakinra | 77 ± 22 | 984 ± 223 | 222 ± 37 |

Example 15

Epitope Determination

Nineteen fully-human antibodies from XenoMouse mice, 9.5.2, 6.33.1, 9.54.2, 6.26.4, 8.50.1, 8.59.2, 9.31.1, 9.2.1, 9.11.3, 5.5.1, 5.36.3, 8.18.1, 8.6.3, 6.20.1, 4.20.2, 6.7.2, 6.34.1, 9.19.1, 9.26.3, were characterized to determine their binding epitopes on IL-1β. It was discovered that none of the antibodies bound to IL-1β when the IL-1β was bound to a solid PVDF membrane support. From this, it was concluded that the mAbs bind IL-1β in solution only via a conformational epitope. The epitope to which an antibody binds can be determined through a variety of ways. For example, SELDI mass spectroscopy was used to determine the epitopes for mAb 9.5.2, mAb 5.5.1 and mAb 8.59.2.

Protein A covalently bound to a PS20 Protein chip array (Ciphergen, Inc.) was used to capture mAbs 9.5.2 and 5.5.1. The mAbs were incubated with purified HIS-tagged mature IL-1β, and the antibody-antigen complex then was digested to completion with a high concentration of Asp-N. The mass of the digestion product of IL-1β retained on the chip via binding to the mAb was determined by SELDI.

For all three antibodies, 9.5.2, 5.5.1 and 8.59.2, the SELDI mass spectroscopy results demonstrated the presence of a 4256 D fragment after on-chip proteolytic digestion of the mAb-IL-1β complex. This corresponded to the mass of a HIS-tag plus amino acids 1-34 of IL-1β. This demonstrates that each of these three antibodies bound to the epitope 1-34 of IL-1β. Accordingly, some embodiments of the invention relate to antibodies that specifically bind to amino acids 1-34 of IL-1β.

Example 16

Residue Interaction Determination

In addition to determining the general epitope that an antibody binds to, particular residues in IL-1β that were involved in forming an interaction with IL-1R type 1 were determined. As will be appreciated by one of skill in the art, the ability to target residues or epitopes on IL-1β that interact with the receptor can allow for the formation or selection of antibodies that bind to IL-1β at these epitopes or residues and thus perform with superior neutralizing ability.

Figure 5:
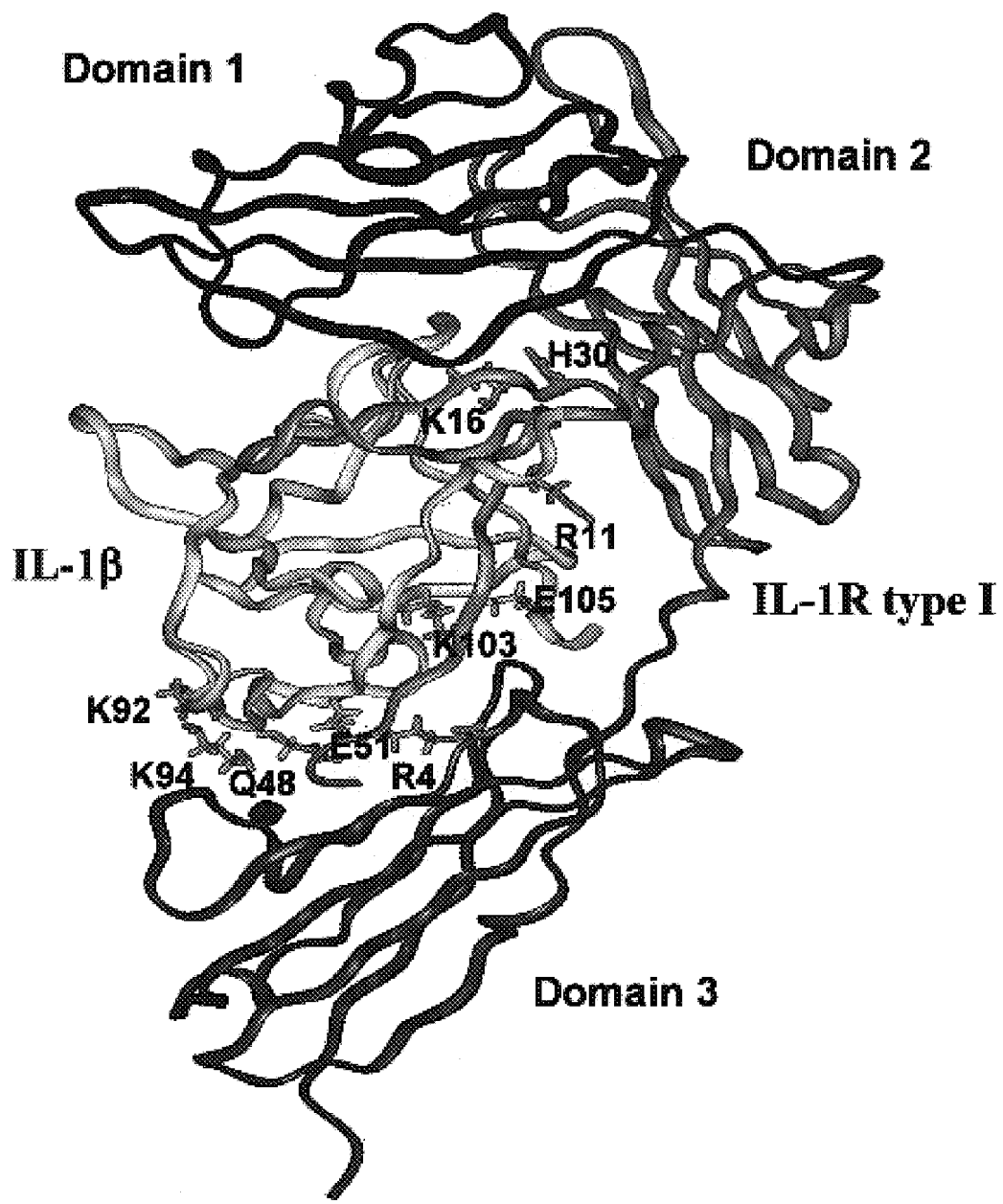
FIG. 5 is a structural model depicting the interaction of IL-1 beta with a receptor.

A structural model of IL-1β interacting with IL-1R type 1 was obtained and is displayed in FIG. 5. Important residues for IL-1β binding and signaling via IL-1R type I include R4, K16, H30, Q48, E51, K92, K103, and E105. Arg4 has previously been shown to be part of the receptor trigger site on IL-1β along with K92, K93, and K94.

To further examine how the antibody binds to IL-1β, site-directed mutants were made in key residues for function, e.g., R4, R11, and H30, within the amino terminal 1-34 amino acids of IL-1β, which contains the mAbs' epitopes, as shown in Example 15 above. Also mutated were K92, K94, K103 and E105. Abrogation of binding to a mutant form of IL-1β (abrogation indicated via a "X" in Table 24) identifies that residue as important in the epitope for binding. A diversity of residues and combinations thereof for binding of neutralizing antibodies against IL-1β is identified in Table 24. A structural model of the IL-1β with each of the two epitopes from mAb 9.5.2 and mAb 5.5.1 was generated through the use of these site directed mutants. The resulting model, demonstrating distinct but overlapping epitopes, is shown in FIG. 6. The H30A mutant retained binding to both of the antibodies, suggesting that it was not essential for mAb neutralizing activity. For mAb 5.5.1, both the R4A and the R11A mutants abrogated binding. In contrast, for mAb 9.5.2, only the R4A mutant prevented binding. Thus, 9.5.2 and 5.5.1 have different, partially overlapping epitopes, while sharing the R4 residue. This suggests that R4 is likely relevant as a neutralizing residue in the mAbs' epitopes.

TABLE 24

| ANTIBODY | R4 | R11 | H30 | K92 | K94 | K103 | E105 |
|---|---|---|---|---|---|---|---|
| 6.20.1 | X | X | | | | X | X |
| 8.6.3 | X | X | | | | | |
| 9.54.2 | | X | X | | | | |
| 6.7.2 | X | X | | | | X | X |
| 5.36.3 | X | X | | | | X | X |
| 6.34.1 | X | X | | | | X | X |
| 8.18.1 | X | X | | | | | |
| 6.26.4 | | X | | | | | |
| 9.5.2 | X | | | | | | |
| 8.50.1 | | X | | | | | |
| 9.19.1 | | | | | | | |
| 9.26.3 | | | | | | | |
| 9.31.1 | | X | | | | | |
| 9.2.1 | | X | | | | | |
| 9.11.3 | | X | | | | | |
| 6.33.1 | | X | | | | | |
| 8.59.2 | | X | | | | | |
| 4.20.2 | X | X | | | | | |
| 5.5.1 | X | X | | | | | |

Thus, antigens concentrating on R4 can be useful in developing further antibodies with desirable characteristics. Similarly, antigens concentrating on R11 can be useful in developing further antibodies with desirable characteristics. In turn, IL-1β antibodies that bind via R4, R11, H30, K103 or E105, key residues alone or in combination, can have useful neutralizing characteristics. In some embodiments, antibodies that bind to these various residues (e.g., denoted in Table 24), either individually or in various combinations, are contemplated.

Example 17

Anti-IL-1β Induced MPO Production in Lungs of BALB/C Mice

Anti-IL-1 beta antibody 9.5.2 was tested for its ability to inhibit IL-1β induced myeloperoxidase (MPO) production as an indirect measurement of neutrophil infiltration in the lungs of BALB/C mice.

Briefly, 13 week old male BALB/C mice were administered 10 mg/kg of 9.5.2 antibody or isotype control intravenously (IV) on day −1; or 5 mg/kg IV on day −1 and 5 mg/kg intranasally (IN) on day 0. Approximately 24 hours post day −1 administration and 2 hrs post day 0 administration, mice received 1 µg of recombinant human IL-1β intranasally in PBS. Additional groups of mice receiving IL-1β alone and PBS alone were included as controls. After 3 hours, the right lung from each mouse was collected and weighed. Samples were processed and tested for the activity of MPO as described per Bai et al. (*Immunology* 2005 February 114(2): 246-254). Average MPO units per gram of lung were calculated and plotted for each group as shown in FIG. 7.

Figure 7:
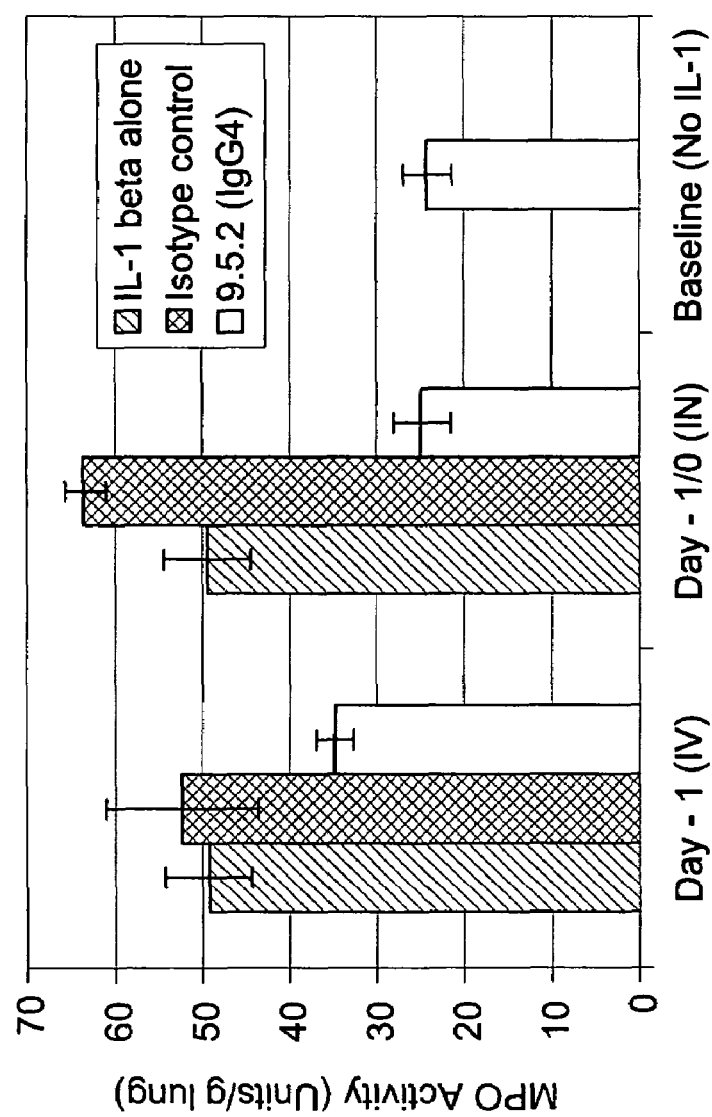
FIG. 7 is a graph depicting myeloperoxidase (MPO) activity in the lungs of BALB/C mice treated with either IL-1β alone or in combination with mAb 9.5.2 or an isotype control.

As shown in FIG. 7, antibody 9.5.2 provided a substantial in vivo reduction in MPO activity in comparison to the control.

Example 18

Structural Analysis of IL-1β Antibodies

The variable heavy chains and the variable light chains of the antibodies were sequenced to determine their DNA sequences. The complete sequence information for the anti-IL-1β antibodies is provided in the sequence listing with nucleotide and amino acid sequences for each gamma and kappa chain combination. The variable heavy sequences were analyzed to determine the VH family, the D-region sequence and the J-region sequence. The sequences were then translated to determine the primary amino acid sequence and compared to the germline VH, D and J-region sequences to assess somatic hypermutations.

Table 25 is a table comparing the antibody heavy chain regions to their cognate germ line heavy chain region. Table 26 is a table comparing the antibody kappa light chain regions to their cognate germ line light chain region.

The variable (V) regions of immunoglobulin chains are encoded by multiple germ line DNA segments, which are joined into functional variable regions ($V_H D J_H$ or $V_K J_K$) during B-cell ontogeny. The molecular and genetic diversity of the antibody response to IL-1β was studied in detail. These assays revealed several points specific to anti-IL-1β antibodies.

TABLE 25

Heavy Chain Analysis

| Chain Name | SEQ ID NO: | V | D | J | FR1 | CDR1 | FR2 | CDR2 | FR3 | CDR3 | FR4 |
|---|---|---|---|---|---|---|---|---|---|---|---|
| | 78 | Germline | | | QVQLVQSGAEVKK PGASVKVSCKAS | GYTFT SYGIS | WVRQAPG QGLEWMG | WISAYNGNT NYAQKLQG | RVTMTTDTSTSTAYME LRSLRSDDTAVYYCAR | YFDY | WGQGTLV TVSS |
| 6.20.1 | 14 | VH1-18 | N.A. | JH4B | QVQLVQSGAEVKK PGASVKVSCKAS | GYTLT SYGIS | WVRQAPG QGLEWMG | WISAYSGKT NYEQKLQG | RVIMTTDTSTNVVYME LRSLRSDDTAVYYCAR | DGPRGYF DF | WGQGTLV TVSS |
| 6.34.1 | 26 | " | " | " | QVQLVQSGAEVKK PGASVKVSCKAS | AYTFT SYGIN | WVRQAPG QGLEWMG | WISGYSGNT NYAQKLQD | RVIMTADTSTNVVYME LRSLRSDDTAVYYCAR | DGPRGYF DY | WGQGTLV TVSS |
| 6.7.1 | 30 | " | " | " | QVQLVQSGAEVKK PGASVKVSCKAS | AYTLT SYGIN | WVRQAPG QGLEWMG | WISAYSGKT NYEQKLQG | RVTMTTDTSTSVVYME LRSLRSDDTAVYYCAR | DGPRGYF DF | WGQGTLV TVSS |
| | 79 | Germline | | | QVQLVESGGGLVK PGGSLRLSCAAS | GFTFS DYYMS | WIRQAPG KGLEWVS | YISSSGSTI YYADSVKG | RFTISRDNAKNSLYLQ MNSLRAEDTAVYYCA | YSGWYFD L | WGRGTLV TVSS |
| 9.31.1 | 66 | VH3-11 | D1-26 | JH2 | QVQLVESGGGLVK PGGSLRLSCAAS | GFTFS DYYMS | WIRQAPG KGLEWVS | YIRSSGSTI YYADSVKG | RFTISRDNAKNSLYLQ MNSLRAEDTAVYYCAR | TPYSGRY HWYFDL | WGRGTLV TVSS |
| | 80 | Germilne | | | QVQLVESGGGVVQ PGRSLRLSCAAS | GFTFS SYGMH | WVRQAPG KGLEWVA | VIWYDGSNK YYADSVKG | RFTISRDNSKNTLYLQ MNSLRAEDTAVYYCAR | FDY | WGQGTLV TVSS |
| 4.20.1 | 2 | VH3-33 | N.A. | JH4B | QVQLVESGGGVVQ PGRSLRLSCAAS | GFTFS NYGMN | WVRQAPG KGLEWVA | VIWYDGNNK SEADSVKG | RFTISRDNSKNTLYLQ MNSLRAEDTAVYYCAR | DSRSGPF DY | WGQGTLV TVSS |
| | 81 | Germilne | | | QVQLVESGGGVVQ PGRSLRLSCAAS | GFTFS SYGMH | WVRQAPG KGLEWVA | VIWYDGSNK YYADSVKG | RFTISRDNSKNTLYLQ MNSLRAEDTAVYYC | YYYGMDV | WGQGTTV TVSS |
| 9.26.1 | 58 | VH3-33 | N.A. | JH6B | QVQLVESGGGVVQ PGRSLRLSCAAS | GFTFN NYGMH | WVRQAPG KGLECVA | VIWYDGGNK YYADSVKG | RFAISRDNSKNTLYLQ MNSLRAEDTAVYYCTA | VTKLNYY YGMDV | WGQGTTV TVSS |
| | 82 | Germilne | | | QVQLVESGGGVVQ PGRSLRLSCAAS | GFTFS SYGMH | WVRQAPG KGLEWVA | VIWYDGSNK YYADSVKG | RFTISRDNSKNTLYLQ MNSLRAEDTAVYYCAR | YDILTGY YYYGMDV | WGQGTTV TVSS |

TABLE 25-continued

Heavy Chain Analysis

| Chain Name | SEQ ID NO: | V | D | J | FR1 | CDR1 | FR2 | CDR2 | FR3 | CDR3 | FR4 |
|---|---|---|---|---|---|---|---|---|---|---|---|
| 9.54.1 | 70 | VH3-33 | D3-9 | JH6B | QVQLVESGGGVVQ PGRSLRLSCAAS | GFTFS SFGMH | WVRQAPG KGLEWVA | VIWYDGSNK YYADSVKG | RFTISRDNSKNTLYLQ MNSLRAEDTAVYYCAR | DPNYDIL TGYYYYG MDV | WGQGTTV TVSS |
|  | 83 |  | Germline |  | QVQLVESGGGVVQ PGRSLRLSCAAS | GFTFS SYGMH | WVRQAPG KGLEWVA | VIWYDGSNK YYADSVKG | RFTISRDNSKNTLYLQ MNSLRAEDTAVYYC | VTYYYGM DV | WGQGTTV TVSS |
| 9.19.1 | 54 | VH3-33 | D4-17 | JH6B | QVQLVESGGGVVQ PGRSLRLSCAAS | GFTFN NYGMH | WVRQAPG KGLECVA | VIWYDGGNK YYADSVKG | RFAISRDNSKNTLYLQ MNSLRAEDTAVYYCTA | VTKLNYY YGMDV | WGQRTTV TVSS |
| 9.2.1 | 62 | " | " | " | QVQLVESGGGVVQ PGRSLRLSCAAS | GFTFN NYGMH | WVRQAPG KGLECVA | VIWYDGGNK YYADSVKG | RFAISRDNSKNTLYLQ MNSLRAEDTAVYYCTA | VTTLYYY YGMDV | WGQGTTV TVSS |
|  | 84 |  | Germline |  | QVQLVESGGGVVQ PGRSLRLSCAAS | GFTFS SYGMH | WVRQAPG KGLEWVA | VIWYDGSNK YYADSVKG | RFTISRDNSKNTLYLQ MNSLRAEDTAVYYCAR | SSSWYFD Y | WGQGTLV TVSS |
| 5.5.1 | 10 | VH3-33 | D6-13 | JH4B | QVQLVESGGGVVQ PGRSLRLSCAAS | GFTFS SYGMH | WVRQAPG KGLEWVA | VIWYDGDNK YYADSVQG | RFTISRDNSKNTLYLQ MNSLRPEDTAVYYCAR | ERSSSWY FDY | WGQGTLV TVSS |
| 9.11.1 | 50 | " | " | " | QVQLVESGGGVVQ PGRSLRLSCAAS | GFTFS VYGMH | WVRQAPG KGLEWVA | VIWYDGNNK YYVDSVKG | RFTISRDNSKNTLYLQ LNSLRAEDTAVYYCAR | ERSSSWY FDY | WGQGTLV TVSS |
|  | 85 |  | Germline |  | QVQLVESGGGVVQ PGRSLRLSCAAS | GFTFS SYGMH | WVRQAPG KGLEWVA | VIWYDGSNK YYADSVKG | RFTISRDNSKNTLYLQ MNSLRAEDTAVYYCAR | SSGWFDY | WGQGTLV TVSS |
| 6.33.1 | 22 | VH3-33 | D6-19 | JH4B | QVQLVESGGGVVQ PGRSLRLSCAAS | GFTFS VYGMH | WVRQAPG KGLEWVA | VIWYDGSNK YYADSVKG | RFTISRDNSKNTLYLQ MNSLRAEDTAVYYCAR | EKSSGWF FDY | WGQGTLV TVSS |
| 8.59.1 | 42 | " | " | " | QVQLVESGGGVVQ PGRSLRLSCAAS | GFTFS IYGIH | WVRQAPG KGLEWVA | VIWYDGSNE YYADSVKG | RFTISRDNSKNTLYLQ MNSLRAEDTAVYYCAR | EKSSGWY FDY | WGQGTLV TVSS |
|  | 86 |  | Germline |  | EVQLVESGGGLVQ PGRSLRLSCTAS | GFTFG DYAMS | WFRQAPG KGLEWVG | FIRSKAYGG TTEYAASVK | RFTISRDDSKSIAYLQ MNSLKTEDTAVYYCTR | EYSSSSY YYGMDV | WGQGTTV TVSS |
| 9.5.2 | 74 | VH3-49 | D6-6 | JH6B | EVQLVESGGGLVK PGRSLRLSCTGS | GFTFG DYALN | WFRQAPG MGLEWVG | FIRGKAYGG TTEYAASVK | RFTISRDDSKSIAYLQ MNSLKTEDTAVYYCNR | EVEYCRS SENYCYG MDV | WGQGTTV TVSS |
|  | 87 |  | Germilne |  | QLQLQESGPGLVK PSETLSLTCTVS | GGSIS SSSYY WG | WIRQPPG KGLEWIG | SIYYSGSTY YNPSLKS | RVTISVDTSKNQFSLK LSSVTAADTAVYYCA | EYSSSSY GMDV | WGQGTTV TVSS |
| 6.26.1 | 18 | VH4-39 | D6-6 | JH6B | QLQLQESGPGLVK PSETLSLTCTVS | GGSIS RSSYY WG | WIRQPPG KGLEWMG | NIYYSGSTH YNPSLKS | RVTISVDTSKNQFSLK LSSVTAADTAVFYCAK | GREYISS SGYGMDV | WGQGTTV TVSS |
|  | 88 |  | Germline |  | QVQLQESGPGLVK PSETLSLTCTVS | GGSIS SYYWS | WIRQPAG KGLEWIG | RIYTSGSTN YNPSLKS | RVTMSVDTSKNQFSLK LSSVTAADTAVYYCAR | YSSWYFD L | WGRGTLV TVSS |
| 8.50.1 | 38 | VH4-4 | D6-13 | JH2 | QVQLQESGPGLVK PSETLSLTCTVS | GGSIS SDYWS | WIRQPAG KGLEWIG | RFYNSGRTN YRPSLKS | RITMSVDTSKNQFSLK LSSVTAADTAVYYCAR | DMYSGRG NWYFDL | WGRGTLV TVSS |
|  | 89 |  | Germline |  | QVQLQESGPGLVK PSETLSLTCTVS | GGSVS SGGYY WS | WIRQPPG KGLEWIG | YIYYSGSTN YNPSLKS | RVTISVDTSKNQFSLK LSSVTAADTAVYYCAR | YGMDV | WGQGTTV TVSS |
| 8.18.1 | 34 | VH4-61 | N.A. | JH6B | QVQLQESGPGLVK PSETLSLTCTVS | GGSVS SGGYY WS | WIRQPPG KGLEWIG | YFYYSGSPN YNPSLKR | RIAISVDTSKNQFSLR LSSVTAADTAVYYCAR | DPMHYYG MDV | WGQGTTV TVSS |
| 8.6.1 | 46 | " | " | " | QVQLQESGPGLVK PSETLSLTCTVS | GGSVS SGGYY WS | WVRQPPG KGLEWIG | CFYFSESTN YNPSLKS | RVTISVDTSKNQFSLK LSSVTAADTAVYYCAR | DPMHYYG MDV | WGQGTTV TVSS |
|  | 90 |  | Germilne |  | QVQLQQSGPGLVK PSQTLSLTCAIS | GDSVS SNSAA WN | WIRQSPS RGLEWLG | RTYYRSKWY NDYAVSVKS | RITINPDTSKNQFSLQ LNSVTPEDTAVYYCAR | QQLVYYY YGMDV | WGQGTTV TVSS |
| 5.36.1 | 6 | VH6-1 | D6-13 | JH6B | QVQLQQSGPGLVK PSQTLSLTCAIS | GGSVS SGGYY WS | WIRQSPS RGLEWLG | RTYYRSKWY NDYAVSVKS | RITINPDTSKNQFSLQ LNSVTPEDTAVYYCAR | EEQQLVR YYYYYGM DV | WGQGTTV TVSS |

TABLE 26

Light Chain Analysis

| Chain Name | SEQ ID NO: | V | J | FR1 | CDR1 | FR2 | CDR2 | FR3 | CDR3 | FR4 |
|---|---|---|---|---|---|---|---|---|---|---|
| | 91 | Germline | | DIVMTQTPLSLSV TPGQPASISC | KSSQSLLHSDG KTYLY | WYLQKPGQ PPQLLIY | EVSNRFS | GVPDRFSGSGSGTDFT LKISRVEAEDVGVYYC T | MQSIQLP# | FGQGTR LEIK |
| 5.36.1 | 8 | A2 | JK5 | DIVMTQTPLSLSV TPGQPASISC | KSSQSLLHSDG RTYLY | WYLQRPGQ PPQLLIY | EASYRFS | GVPDRFSGSGSGTDFT LKISRVEAEDVGIYYC T | MQSIQLPR | FGQGTR LEIK |
| | 92 | Germilne | | EIVLTQSPDFQSV TPKEKVTITC | RASQSIGSSLH | WYQQKPDQ SPKLLIK | YASQSFS | GVPSRFSGSGSGTDFT LTINSLEAEDAATYYC T | HQSSSLPF | FGPGTK VDIK |
| 4.20.1 | 4 | A26 | JK3 | EIVLTQSPDFQSV TPKEKVTITC | RASQSIGSSLH | WYQQKPDQ SPKLLIK | FASQSFS | GVPSRISGSGSGTDFT LTINSLEAEDAATYYC T | HQSSSLPF | FGPGTK VDIK |
| | 93 | Germilne | | EIVLTQSPGTLSL SPGERATLSC | RASQSVSSSYL A | WYQQKPGQ APRLLIY | GASSRAT | GIPDRFSGSGSGTDFT LTISRLEPEDFAVYYC T | QQYGSS## | FGQGTK VEIK |
| 8.59.1 | 44 | A27 | JK1 | EIVLTQSPGTLSL SPGERATLSC | RASQSISSSCL A | CYQQKPGQ TPRLLIY | GASSWAT | GIPDRFSGSRSGTDFT LSISRLEPDDFAVCYC T | QQYGSSPP | FGQGTK VEIK |
| | 94 | Germline | | QSALTQPASVSGS PGQSITISC | TGTSSDVGGYN YVS | WYQQHPGK APKLMIY | EVSNRPS | GVSNRFSGSKSGNTAS LTISGLQAEDEADYYC #V | SSYTSS## | FGGGTK LTVL |
| 9.19.1 | 56 | V1-4 | JL2 | QSALTQPASVSGS PGQSITISC | TGTSSDVGGYN YVS | WYQQHPGK APKFMIY | EVSNRPS | GVSNRFSGSKSGNTAS LTISGLQAEDEADYYC LV | SSYTSSSI | FGGGTK LTVL |
| 9.26.1 | 60 | " | " | QSALTQPASVSGS PGQSITISC | TGTSSDVGGYN YVS | WYQQHPGK APKLMIY | EVSNRPS | GVSNRFSGSKSGNTAS LTISGLQAEDEADYYC LV | SSYTSSSI | FGGGTK LTVL |
| 9.2.1 | 64 | " | " | QSALTQPASVSGS PGQSITISC | TGTSSDVGGYN YVS | WYQQHPGK APKLMIY | EVSNRPS | GVSNRFSGSKSGNTAS LTISGLQAEDEADYYC LV | SSYTSSSI | FGGGTK LTVL |
| | 95 | Germline | | QSALTQPASVSGS PGQSITISC | TGTSSDVGSYN LVS | WYQQHPGK APKLMIY | EGSKRPS | GVSNRFSGSKSGNTAS LTISGLQAEDEADYYC #V | CSYAGSS# | FGGGTK LTVL |
| 6.33.1 | 24 | V1-7 | JL2 | QSALTQPASVSGS PGQSITISC | TGTSSDVGSYN LVS | WYQQHPGK APKLMIY | EVSKRPS | GISNRFSGSKSGNTAS LTISGLQAEDEADYYC WV | CSYAGNSI | FGGGTK LTVL |
| | 96 | Germline | | QSALTQPASVSGS PGQSITISC | TGTSSDVGSYN LVS | WYQQHPGK APKLMIY | EGSKRPS | GVSNRFSGSKSGNTAS LTISGLQAEDEADYYC WV | CSYAGSST | FGGGTK LTVL |
| 5.5.1 | 12 | V1-7 | JL3 | QSALTQPASVSGS PGQSITISC | TGTSSDVGSYN LVS | WYQQHPGK APKLMIY | EVSKRPS | GISNRFSGSKSGNTAS LTISGLQAEDEADYYC WV | CSYAGSST | FGGGTK LTVL |
| 9.11.1 | 52 | " | " | QSALTQPASVSGS SGQSITISC | TGTSSDVGSYN LVS | WYQQHPGK APKLMIY | EVSKRPS | GVSNRFSGSKSGNTAS LTISGLQAEDEADYYC WV | CSYAGNSN | FGGGTK LTVL |
| | 97 | Germline | | SYELTQPPSVSVS PGQTASITC | SGDKLGDKYAC | WYQQKPGQ SPVLVIY | QDSKRPS | GIPERFSGSNSGNTAT LTISGTQAMDEADYYC V | QAWDSSTV | FGGGTK LTVL |
| 6.20.1 | 16 | V2-1 | JL2 | SYELTQPPSVSVS PGQTASFTC | SGDKLGDKYAC | WYQQKPGQ SPVLVIY | QDRKRPS | GIPERFSGSNSGNTAT LTISGTQAMDEADYYC V | QAWDSSTV | FGGGTK LTVL |
| 6.26.1 | 20 | " | " | SYELTQPPSVSVS PGQTASITC | SGDKLGNKYVC | WYQQKPGQ SPVLVIF | QDSRRPS | GIPERFSGSNSGNTAT LTISGTQAMDEADYYC I | QAWDTSTV | FGGGTV LTVL |
| 6.34.1 | 28 | " | " | SYELTQPPSVSVS PGQTASITC | SGDKLGDKYAC | WYQQKPGQ SPVLVIY | QDSKRPS | GIPERFSGSNSGNTAT LTISGTQAMDEADYYC V | QAWDSSTV | FGGGTK LTVL |
| 6.7.1 | 32 | " | " | SYELTQPPSVSVS PGQTASTIC | SGDKLGDKYAC | WYQQKPGQ SPVLVIY | QDSKRPS | GIPERFSGSNSGNTAT LTISGTQAMDEADYYC V | QAWDSSTV | FGGGTK LTVL |
| 8.18.1 | 36 | " | " | SSELTQPPSVSVF PGQTANFTC | SGDKLGDKFAC | WYQQKPGQ SPVLVIY | RDNKRPS | GIPERFSGSNSGNTAT LTISGTQAMDEADYYC VV | QAWDSSTY | FGGGTK LTVL |
| 8.6.1 | 48 | " | " | SFELTQPPSVSVS PGQTASITC | SGDKLGDKFAC | WYQQKPGQ SPVLVIY | QDTKRPS | GIPERISGSNSGNTAT LTISGTQAMDEADYYC VV | QAWDSSTY | FGGGTK LTVL |
| 9.5.2 | 76 | " | " | SYELTQPPSVSVS PGQTASITC | SGDKLGDKFAC | WYQQKPGQ SPVLVIY | QDTKRPS | GIPERFSGSNSGNTAT LTISGTQAMDEADYYC V | QAWDSNTV | FGGGTK LTVL |
| | 98 | Germline | | SSELTQDPAVSVA LGQTVRITC | QGDSLRSYYAS | WYQQKPGQ APVLVIY | GKNNRPS | GIPDRFSGSSSGNTAS LTITGAQAEDEADYYC HLV | NSRDSSGN | FGGGTK LTVL |

TABLE 26-continued

Light Chain Analysis

| Chain Name | SEQ ID NO: | V | J | FR1 | CDR1 | FR2 | CDR2 | FR3 | CDR3 | FR4 |
|---|---|---|---|---|---|---|---|---|---|---|
| 9.54.1 | 72 | V2-13 | JL2 | SSELTQDPAVSVA LGQTVRITC | QGDILRTYYAS | WYQQKPGQ APVLVIY | GKNDRPS | GIPDRFSGSSSGNTAS LTITGAQAEDEADYYC | DSRDNTVT HLV | FGGGTK LTVL |
|  | 99 | Germline |  | SYELTQPPSVSVS PGQTARITC | SGDALPKKYAY | WYQQKSGQ APVLVIY | EDSKRPS | GIPERFSGSSSGTMAT LTISGAQVEDEADYYC | YSTDSSGN HRV | FGGGTK LTVL |
| 8.50.1 | 40 | V2-7 | JL2 | SYELTQPPSVSVS PGQTARITC | SGDALPKKYAY | WYQQKSGQ APVLVIY | EDSKRPS | GIPERFSGSSSGTMAT LTISGAQVEDEADYYC | YSTDSSDN HRV | FGGGTK LTVL |
|  | 100 | Germline |  | SYELTQPPSVSVS PGQTARITC | SGDALPKKYAY | WYQQKSGQ APVLVIY | EDSKRPS | GIPERFSGSSSGTMAT LTISGAQVEDEADYYC | YSTDSSGN HRV | FGGGTK LTVL |
| 9.31.1 | 68 | V2-7 | JL3 | SYELTQPPSVSVS PGQTARITC | SGDALPIKYAY | WYQHKSGQ APVLVIY | EDSKRPS | GIPERFSGSSSGTMAT LTISGAQVEDEADYYC | YSTDSSGN HRV | FGGGTK LTVL |

Example 19

Uses of IL-1β Antibodies for the Treatment of IL-1β Related Disorders

A human patient exhibiting an IL-1β related disorder is injected one time weekly with an effective amount of IL-1β antibody, such as 9.5.2. At periodic times during the treatment, the patient is monitored to determine whether the symptoms of the IL-1β related disorder has subsided. Following treatment, it is found that patients undergoing treatment with the IL-1β antibody have reduced symptoms relating to IL-1β related disorders, in comparison to patients that are not treated.

Example 20

Uses of IL-1β Antibodies for the Treatment of Arthritis

A human patient exhibiting symptoms of arthritis is injected weekly with an effective amount of IL-1β antibody, such as 9.5.2. At periodic times during the treatment, the human patient is monitored to determine whether the arthritis condition has subsided. Following treatment, it is found that the patient receiving the treatment with the IL-1β antibodies has reduced symptoms in comparison to arthritis patients not receiving the treatment.

Example 21

Uses of IL-1β Antibodies for the Prevention of Osteoporosis

A human patient exhibiting symptoms of osteoporosis is injected weekly with an effective amount of IL-1β antibody, such as 9.5.2. At periodic times during the treatment, the human patient is monitored to determine whether the osteoporosis condition has subsided. Following treatment, it is found that the patient receiving the treatment with the IL-1β antibodies has reduced symptoms in comparison to osteoporosis patients not receiving the treatment.

Example 22

Use of IL-1β Antibodies as a Diagnostic Agent

Detection of IL-1β Antigen in a Sample
An Enzyme-Linked Immunosorbent Assay (ELISA) for the detection of IL-1β antigen in a sample can used to diagnose patients exhibiting high levels of IL-1β production. In the assay, wells of a microtiter plate, such as a 96-well microtiter plate or a 384-well microtiter plate, are adsorbed for several hours with a first fully human monoclonal antibody directed against IL-1β. The immobilized antibody serves as a capture antibody for any of the antigen that may be present in a test sample. The wells are rinsed and treated with a blocking agent such as milk protein or albumin to prevent nonspecific adsorption of the analyte.

Subsequently the wells are treated with a test sample suspected of containing the antigen, or with a solution containing a standard amount of the antigen. Such a sample may be, for example, a serum sample from a subject suspected of having levels of circulating antigen considered to be diagnostic of a pathology.

After rinsing away the test sample or standard, the wells are treated with a second fully human monoclonal IL-1β antibody that is labeled by conjugation with biotin. A monoclonal or mouse or other species origin can also be used. The labeled IL-1β antibody serves as a detecting antibody. After rinsing away excess second antibody, the wells are treated with avidin-conjugated horseradish peroxidase (HRP) and a suitable chromogenic substrate. The concentration of the antigen in the test samples is determined by comparison with a standard curve developed from the standard samples.

This ELISA assay provides a highly specific and very sensitive assay for the detection of the IL-1β antigen in a test sample.

Determination of IL-1β Antigen Concentration in Patients
A sandwich ELISA can quantify IL-1β levels in human serum. Two fully human monoclonal IL-1β antibodies from the sandwich ELISA, recognize different epitopes on the IL-1β molecule. Alternatively, monoclonal antibodies of mouse or other species origin may be used. The ELISA is performed as follows: 50 μL of capture IL-1β antibody in coating buffer (0.1 M NaHCO$_3$, pH 9.6) at a concentration of 2 μg/mL is coated on ELISA plates (Fisher). After incubation at 4° C. overnight, the plates are treated with 200 μL of blocking buffer (0.5% BSA, 0.1% Tween 20, 0.01% Thimerosal in PBS) for 1 hour at 25° C. The plates are washed (3×) using 0.05% Tween 20 in PBS (washing buffer, WB). Normal or patient sera (Clinomics, Bioreclaimation) are diluted in blocking buffer containing 50% human serum. The plates are incubated with serum samples overnight at 4° C., washed with WB, and then incubated with 100 μL/well of biotinylated detection IL-1β antibody for 1 hour at 25° C. After washing, the plates are incubated with HRP-Streptavidin for 15 minutes, washed as before, and then treated with 100 μL/well of o-phenylenediamine in $H_2O_2$ (Sigma developing solution) for color generation. The reaction is stopped with 50 μL/well of $H_2SO_4$ (2M) and analyzed using an ELISA plate reader at 492 nm. Concentration of IL-1β antigen in serum samples is calculated by comparison to dilutions of purified IL-1β antigen using a four parameter curve fitting program.

Incorporation by Reference

All references cited herein, including patents, patent applications, papers, text books, and the like, and the references cited therein, to the extent that they are not already, are hereby incorporated herein by reference in their entirety.

Equivalents

The foregoing written specification is considered to be sufficient to enable one skilled in the art to practice the invention. The foregoing description and examples detail certain preferred embodiments of the invention and describe the best mode contemplated by the inventors. It will be appreciated, however, that no matter how detailed the foregoing may appear in text, the invention may be practiced in many ways and the invention should be construed in accordance with the appended claims and any equivalents thereof.

What is claimed is:

1. A monoclonal antibody comprising a light chain polypeptide having the amino acid sequence of SEQ ID NO: 76.

2. A monoclonal antibody comprising a heavy chain polypeptide having the amino acid sequence of SEQ ID NO: 74.

3. A targeted binding agent that neutralizes interleukin-1β (IL-1β) activity, wherein the targeted binding agent comprises:
   a heavy chain polypeptide comprising CDR1, CDR2, and CDR3 of SEQ ID NO: 74; and
   a light chain polypeptide comprising CDR1, CDR2, and CDR3 of SEQ ID NO: 76.

4. The targeted binding agent of claim 3, wherein said targeted binding agent is an antibody comprising a light chain polypeptide having the amino acid sequence of SEQ ID NO: 76 and a heavy chain polypeptide having the amino acid sequence of SEQ ID NO: 74.

5. The targeted binding agent of claim 3, wherein said targeted binding agent binds to and neutralizes IL-1β with a KD of 300 fM or less.

6. The targeted binding agent of claim 3, wherein said targeted binding agent comprises an antibody having an IgG2 isotype.

7. The targeted binding agent of claim 3, wherein said targeted binding agent binds to amino acids 1-34 of the human IL-1β.

8. The targeted binding agent of claim 3, wherein said targeted binding agent binds to IL-1 beta via an arginine at the fourth amino acid of human IL-1 beta.

9. The targeted binding agent of claim 3, wherein said targeted binding agent binds to IL-1 beta via an arginine at the eleventh amino acid of human IL-1 beta.

10. A method of effectively treating an animal suffering from an IL-1β related disorder, the method comprising:
    selecting an animal in need of treatment for an IL-1β related disorder; and
    administering to said animal a therapeutically effective dose of the targeted binding agent of claim 3.

11. The method of claim 10, wherein the treatable IL-1β related disorder is selected from the group consisting of inflammatory disorders, arthritis, cachexia and chronic fatigue syndrome, osteoporosis, atherosclerosis, pain related disorders, congestive heart failure, leukemias, multiple myelomas, tumor growth and metastatic spreading.

12. The method of claim 10, wherein said targeted binding agent is a neutralizing fuily human monoclonal antibody that binds to amino acids 1-34 of the human IL-1β.

13. A fully human monoclonal antibody:
wherein said monoclonal antibody is mAb 9.5.2.

14. An isolated polynucleotide that encodes a heavy chain variable domain of an antibody, wherein said heavy chain variable domain comprises CDR1, CDR2, and CDR3 from the amino acid sequence of SEQ ID NO: 74.

15. A vector comprising the isolated polynucleotide of claim 14.

16. A host cell comprising the vector of claim 15.

17. An isolated polynucleotide that encodes a light chain variable domain of an antibody, wherein said light chain variable domain comprises CDR1, CDR2, and CDR3 from the amino acid sequence of SEQ ID NO: 76.

18. A vector comprising the isolated polynucleotide of claim 17.

19. A host cell comprising the vector of claim 17.

* * * * *

SEQUENCE LISTING

<160> NUMBER OF SEQ ID NOS: 100

<210> SEQ ID NO 1
<211> LENGTH: 354
<212> TYPE: DNA
<213> ORGANISM: Homo sapiens

<400> SEQUENCE: 1

```
caggtacaac tggtggagtc tggggaggc gtggtccagc ctgggaggtc cctgagactc      60
tcctgtgcag cgtctgggtt caccttcagt aactatggca tgaactgggt ccgccaggct     120
ccaggcaagg ggctggagtg ggtggcagtt atatggtatg atggaaataa taaatcagag     180
gcagactccg tgaagggccg attcaccatc tccagagaca attccaagaa cacgctgtat     240
ctacaaatga acagcctgag agccgaggac acggctgtgt attactgtgc gagagatagc     300
cgcagtggcc cttttgacta ctggggccag ggtaccctgg tcaccgtctc ctca          354
```

<210> SEQ ID NO 2
<211> LENGTH: 118
<212> TYPE: PRT
<213> ORGANISM: Homo sapiens

<400> SEQUENCE: 2

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Asn Tyr
             20                  25                  30

Gly Met Asn Trp Val Arg Gln Ala Pro Gly Lys Gly Leu Glu Trp Val
         35                  40                  45

Ala Val Ile Trp Tyr Asp Gly Asn Asn Lys Ser Glu Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Ser Arg Ser Gly Pro Phe Asp Tyr Trp Gly Gln Gly Thr
            100                 105                 110

Leu Val Thr Val Ser Ser
        115
```

<210> SEQ ID NO 3
<211> LENGTH: 321
<212> TYPE: DNA
<213> ORGANISM: Homo sapiens -continued

```
<400> SEQUENCE: 3
gaaattgtac tgactcagtc tccagacttt cagtctgtga ctccaaagga gaaagtcacc    60
atcacctgcc gggccagtca gagcattggt agtagcttac actggtacca gcagaaacca   120
gatcagtctc caaagctcct catcaagttt gcttcccagt ccttctcagg ggtcccctcg   180
aggatcagtg gcagtggatc tgggacagat ttcaccctca ccatcaatag cctggaagct   240
gaagatgctg caacgtatta ctgtcatcag agtagtagtt taccattcac tttcggccct   300
gggaccaaag tggatatcaa a                                             321

<210> SEQ ID NO 4
<211> LENGTH: 107
<212> TYPE: PRT
<213> ORGANISM: Homo sapiens

<400> SEQUENCE: 4

Glu Ile Val Leu Thr Gln Ser Pro Asp Phe Gln Ser Val Thr Pro Lys
  1               5                  10                  15

Glu Lys Val Thr Ile Thr Cys Arg Ala Ser Gln Ser Ile Gly Ser Ser
             20                  25                  30

Leu His Trp Tyr Gln Gln Lys Pro Asp Gln Ser Pro Lys Leu Leu Ile
         35                  40                  45

Lys Phe Ala Ser Gln Ser Phe Ser Gly Val Pro Ser Arg Ile Ser Gly
     50                  55                  60

Ser Gly Ser Gly Thr Asp Phe Thr Leu Thr Ile Asn Ser Leu Glu Ala
 65                  70                  75                  80

Glu Asp Ala Ala Thr Tyr Tyr Cys His Gln Ser Ser Ser Leu Pro Phe
                 85                  90                  95

Thr Phe Gly Pro Gly Thr Lys Val Asp Ile Lys
            100                 105

<210> SEQ ID NO 5
<211> LENGTH: 383
<212> TYPE: DNA
<213> ORGANISM: Homo sapiens

<400> SEQUENCE: 5
caggtacagc tgcagcagtc aggtccagga ctggtgaagc cctcgcagac cctctcactc    60
acctgtgcca tctccgggga cagtgtctct agcaacagtg ctgcttggaa ctggatcagg   120
cagtccccat cgagaggcct tgagtggctg ggaaggacat actacaggtc caagtggtat   180
aatgattatg cagtatctgt gaaaagtcga ataaccatca cccagacac atccaagaac   240 cagttctccc tgcagctgaa ctctgtgact cccgaggaca cggctgtgta ttactgtgca   300
agagaggagc agcagctggt acgatactac tactactacg gtatggacgt ctggggccaa   360
gggaccacgg tcaccgtctc ctc                                           383

<210> SEQ ID NO 6
<211> LENGTH: 127
<212> TYPE: PRT
<213> ORGANISM: Homo sapiens

<400> SEQUENCE: 6

Gln Val Gln Leu Gln Gln Ser Gly Pro Gly Leu Val Lys Pro Ser Gln
  1               5                  10                  15

Thr Leu Ser Leu Thr Cys Ala Ile Ser Gly Asp Ser Val Ser Ser Asn
             20                  25                  30
```

```
Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Glu Glu Gln Leu Val Arg Tyr Tyr Tyr Tyr
            100                 105                 110

Tyr Gly Met Asp Val Trp Gly Gln Gly Thr Thr Val Thr Val Ser
            115                 120                 125
```

<210> SEQ ID NO 7
<211> LENGTH: 336
<212> TYPE: DNA
<213> ORGANISM: Homo sapiens

<400> SEQUENCE: 7

```
gatattgtga tgacccagac tccactctct ctgtccgtca cccctggaca gccggcctcc      60
atctcctgca agtctagtca gagcctcctg catagtgatg gaaggaccta tttgtattgg     120
tacctgcaga ggccaggcca gcctccacag ctcctgatct atgaagcttc ctaccggttc     180
tctggagtgc cagataggtt cagtggcagc gggtcaggga cagatttcac actgaaaatc     240
agccgggtgg aggctgagga tgttggaatt tattactgca tgcaaagtat acagcttcct     300
cgcaccttcg gccaagggac acgactggag attaaa                                336
```

<210> SEQ ID NO 8
<211> LENGTH: 112
<212> TYPE: PRT
<213> ORGANISM: Homo sapiens

<400> SEQUENCE: 8

```
Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
                20                  25                  30

Asp Gly Arg Thr Tyr Leu Tyr Trp Tyr Leu Gln Arg Pro Gly Gln Pro
            35                  40                  45

Pro Gln Leu Leu Ile Tyr Glu Ala Ser Tyr Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Ser
                85                  90                  95

Ile Gln Leu Pro Arg Thr Phe Gly Gln Gly Thr Arg Leu Glu Ile Lys
            100                 105                 110
```

<210> SEQ ID NO 9
<211> LENGTH: 357
<212> TYPE: DNA
<213> ORGANISM: Homo sapiens

<400> SEQUENCE: 9

```
caggtgcagc tggtggagtc tgggggaggc gtggtccagc ctgggaggtc cctgagactc      60
tcctgtgcag cgtctggatt caccttcagt agctatggca tgcactgggt ccgccaggct     120
```

```
ccaggcaagg ggctggagtg ggtggcagtt atatggtatg atggagataa taaatactat    180
gcagactccg tgcagggccg attcaccatc tccagagaca attccaagaa cacgctgtat    240
ctgcaaatga acagcctgag acccgaggac acggctgtgt attactgtgc gagagaacgg    300
agcagcagct ggtactttga ctactggggc cagggaaccc tggtcaccgt ctcctca      357

<210> SEQ ID NO 10
<211> LENGTH: 119
<212> TYPE: PRT
<213> ORGANISM: Homo sapiens

<400> SEQUENCE: 10

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Val Ile Trp Tyr Asp Gly Asp Asn Lys Tyr Tyr Ala Asp Ser Val
     50                  55                  60

Gln Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Val Tyr Tyr Cys
                 85                  90                  95

Ala Arg Glu Arg Ser Ser Ser Trp Tyr Phe Asp Tyr Trp Gly Gln Gly
            100                 105                 110

Thr Leu Val Thr Val Ser Ser
        115

<210> SEQ ID NO 11
<211> LENGTH: 330
<212> TYPE: DNA
<213> ORGANISM: Homo sapiens

<400> SEQUENCE: 11
cagtctgccc tgactcagcc tgcctccgtg tctgggtctc ctggacagtc gatcaccatc     60
tcctgcactg gaaccagcag tgatgttggg agttataacc ttgtctcctg gtaccaacag    120
cacccaggca aagcccccaa actcatgatt tatgaggtca gtaagcggcc ctcagggatt    180
tctaatcgct tctctggctc caagtctggc aacacggcct ccctgacaat ctctgggctc    240
caggctgagg acgaggctga ttattactgc tgctcatatg caggtagtag cacttgggtg    300
ttcggcggag ggaccaagct gaccgtccta                                    330

<210> SEQ ID NO 12
<211> LENGTH: 110
<212> TYPE: PRT
<213> ORGANISM: Homo sapiens

<400> SEQUENCE: 12

Gln Ser Ala Leu Thr Gln Pro Ala Ser Val Ser Gly Ser Pro Gly Gln
  1               5                  10                  15

Ser Ile Thr Ile Ser Cys Thr Gly Thr Ser Ser Asp Val Gly Ser Tyr
             20                  25                  30

Asn Leu Val Ser Trp Tyr Gln Gln His Pro Gly Lys Ala Pro Lys Leu
         35                  40                  45

Met Ile Tyr Glu Val Ser Lys Arg Pro Ser Gly Ile Ser Asn Arg Phe
     50                  55                  60
```

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
            85                  90                  95

Ser Thr Trp Val Phe Gly Gly Gly Thr Lys Leu Thr Val Leu
        100                 105                 110

<210> SEQ ID NO 13
<211> LENGTH: 354
<212> TYPE: DNA
<213> ORGANISM: Homo sapiens

<400> SEQUENCE: 13
caggttcagc tggtgcagtc tggagctgag gtgaagaagc ctggggcctc agtgaaggtc      60
tcctgcaagg cttctggtta caccttaacc agctatggta tcagttgggt gcgacaggcc    120
cctggacagg gcttgagtg gatgggatgg atcagcgctt acagtggtaa aacaaactat     180
gaacagaagc tccagggcag agtcatcatg accacagaca catccacgaa tgtagtctac    240
atggaactga ggagcctgag atctgacgac acggccgtgt attactgtgc gagagatggg    300 ccgagggggct actttgactt ctggggccag ggaaccctgg tcaccgtctc ctca         354

<210> SEQ ID NO 14
<211> LENGTH: 118
<212> TYPE: PRT
<213> ORGANISM: Homo sapiens

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Ser Gly Lys Thr Asn Tyr Glu Gln Lys Leu
    50                  55                  60

Gln Gly Arg Val Ile Met Thr Thr Asp Thr Ser Thr Asn Val Val Tyr
65                  70                  75                  80

Met Glu Leu Arg Ser Leu Arg Ser Asp Asp Thr Ala Val Tyr Tyr Cys
                85                  90                  95

Ala Arg Asp Gly Pro Arg Gly Tyr Phe Asp Phe Trp Gly Gln Gly Thr
            100                 105                 110

Leu Val Thr Val Ser Ser
        115

<210> SEQ ID NO 15
<211> LENGTH: 318
<212> TYPE: DNA
<213> ORGANISM: Homo sapiens

<400> SEQUENCE: 15
tcctatgagc tgactcagcc accctcagtg tccgtgtccc caggacagac agccagcttc      60
acctgctctg gagataaaatt gggggataaa tatgcttgct ggtatcagca gaagccaggc    120
cagtcccctg tgctggtcat ctatcaagat aggaagcggc cctcagggat ccctgagcga    180
ttctctggct ccaactctgg gaacacagcc actctgacca tcagcgggac ccaggctatg    240

```
gatgaggctg actattactg tcaggcgtgg gacagtagca ctgtggtttt cggcggaggg      300
accaagctga ccgtccta                                                    318
```

<210> SEQ ID NO 16
<211> LENGTH: 106
<212> TYPE: PRT
<213> ORGANISM: Homo sapiens

<400> SEQUENCE: 16

```
Ser Tyr Glu Leu Thr Gln Pro Pro Ser Val Ser Val Ser Pro Gly Gln
  1               5                  10                  15

Thr Ala Ser Phe Thr Cys Ser Gly Asp Lys Leu Gly Asp Lys Tyr Ala
             20                  25                  30

Cys Trp Tyr Gln Gln Lys Pro Gly Gln Ser Pro Val Leu Val Ile Tyr
         35                  40                  45

Gln Asp Arg Lys Arg Pro Ser Gly Ile Pro Glu Arg Phe Ser Gly Ser
     50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Gln Ala Trp Asp Ser Ser Thr Val Val
                 85                  90                  95

Phe Gly Gly Gly Thr Lys Leu Thr Val Leu
            100                 105
```

<210> SEQ ID NO 17
<211> LENGTH: 371
<212> TYPE: DNA
<213> ORGANISM: Homo sapiens

<400> SEQUENCE: 17

```
cagctgcagc tgcaggagtc gggcccagga ctggtgaagc cttcggagac cctgtccctc       60
acctgcactg tctctggtgg ctccatcagc agaagtagtt actactgggg ctggatccgc      120
cagcccccag ggaaggggct ggagtggatg gggaatatct attatagtgg gagcacccac      180
tacaacccgt ccctcaagag tcgtgtcacc atatccgtgg acacgtccaa gaaccagttc      240
tccctgaagc tgagctctgt gaccgccgca gacacggctg tgttttactg tgcgaaaggt      300
cgggagtata tcagctcgtc cgggtacggt atggacgtct ggggccaagg gaccacggtc      360
accgtctcct c                                                           371
```

<210> SEQ ID NO 18
<211> LENGTH: 123
<212> TYPE: PRT
<213> ORGANISM: Homo sapiens

<400> SEQUENCE: 18

```
Gln Leu Gln Leu Gln Glu Ser Gly Pro Gly Leu Val Lys Pro Ser Glu
  1               5                  10                  15

Thr Leu Ser Leu Thr Cys Thr Val Ser Gly Gly Ser Ile Ser Arg Ser
             20                  25                  30

Ser Tyr Tyr Trp Gly Trp Ile Arg Gln Pro Pro Gly Lys Gly Leu Glu
         35                  40                  45

Trp Met Gly Asn Ile Tyr Tyr Ser Gly Ser Thr His Tyr Asn Pro Ser
     50                  55                  60

Leu Lys Ser Arg Val Thr Ile Ser Val Asp Thr Ser Lys Asn Gln Phe
 65                  70                  75                  80
```

```
Ser Leu Lys Leu Ser Ser Val Thr Ala Ala Asp Thr Ala Val Phe Tyr
                85                  90                  95

Cys Ala Lys Gly Arg Glu Tyr Ile Ser Ser Gly Tyr Gly Met Asp
            100                 105                 110

Val Trp Gly Gln Gly Thr Thr Val Thr Val Ser
        115                 120

<210> SEQ ID NO 19
<211> LENGTH: 318
<212> TYPE: DNA
<213> ORGANISM: Homo sapiens

<400> SEQUENCE: 19
tcctatgagc tgactcagcc accctcagtg tccgtgtccc caggacagac agccagcatc      60
acctgctctg gagataaaat tgggaataaa tatgtttgct ggtatcagca gaagccaggc     120
cagtcccctg tgttggtcat ctttcaagat agcaggcggc cctcaggat ccctgagcga     180 ttctctggct ccaactctgg gaacacagcc actctgacca tcagcgggac ccaggctatg     240
gatgaggctg actattactg tcaggcgtgg gacaccagca ctgtgatatt cggcggaggg     300
accaagctga ccgtccta                                                   318

<210> SEQ ID NO 20
<211> LENGTH: 106
<212> TYPE: PRT
<213> ORGANISM: Homo sapiens

<400> SEQUENCE: 20

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asn Lys Tyr Val
            20                  25                  30

Cys Trp Tyr Gln Gln Lys Pro Gly Gln Ser Pro Val Leu Val Ile Phe
        35                  40                  45

Gln Asp Ser Arg Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Thr Ser Thr Val Ile
                85                  90                  95

Phe Gly Gly Gly Thr Lys Leu Thr Val Leu
            100                 105

<210> SEQ ID NO 21
<211> LENGTH: 357
<212> TYPE: DNA
<213> ORGANISM: Homo sapiens

<400> SEQUENCE: 21
caggtgcagc tggtggagtc tgggggaggc gtggtccagc ctgggaggtc cctgagactc      60
tcctgtgcag cgtctggatt caccttcagt gtctatggca tgcactgggt ccgccaggct     120
ccaggcaagg ggctggagtg ggtggcagtt atatggtatg atggaagtaa taatactat     180 gcagactccg tgaagggccg attcaccatc tccagagaca attccaagaa cacgctgtat     240
ctgcaaatga acagcctgag agccgaggac acggctgtgt attactgtgc gagagagaag     300
agcagtggct ggttctttga ctactggggc cagggaaccc tggtcaccgt ctcctca        357
```

```
<210> SEQ ID NO 22
<211> LENGTH: 119
<212> TYPE: PRT
<213> ORGANISM: Homo sapiens

<400> SEQUENCE: 22

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Val Tyr
             20                  25                  30

Gly Met His Trp Val Arg Gln Ala Pro Gly Lys Gly Leu Glu Trp Val
         35                  40                  45

Ala Val Ile Trp Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Arg Glu Lys Ser Ser Gly Trp Phe Phe Asp Tyr Trp Gly Gln Gly
            100                 105                 110

Thr Leu Val Thr Val Ser Ser
            115

<210> SEQ ID NO 23
<211> LENGTH: 330
<212> TYPE: DNA
<213> ORGANISM: Homo sapiens

<400> SEQUENCE: 23
cagtctgccc tgactcagcc tgcctccgtg tctgggtctc ctggacagtc gatcaccatc    60
tcctgcactg gaaccagcag tgatgttggg agttataacc ttgtctcctg gtaccaacaa   120
cacccaggca aagcccccaa actcatgatt tatgaggtca gtaagcggcc ttcaggaatt   180
tctaatcgct tctctggctc caagtctggc aacacggcct ccctgacaat ctctgggctc   240
caggctgagg acgaggctga ttattactgc tgctcatatg caggtaatag catttgggta   300
ttcggcggcg ggaccaagct gaccgtccta                                    330

<210> SEQ ID NO 24
<211> LENGTH: 110
<212> TYPE: PRT
<213> ORGANISM: Homo sapiens

<400> SEQUENCE: 24

Gln Ser Ala Leu Thr Gln Pro Ala Ser Val Ser Gly Ser Pro Gly Gln
  1               5                  10                  15

Ser Ile Thr Ile Ser Cys Thr Gly Thr Ser Ser Asp Val Gly Ser Tyr
             20                  25                  30

Asn Leu Val Ser Trp Tyr Gln Gln His Pro Gly Lys Ala Pro Lys Leu
         35                  40                  45

Met Ile Tyr Glu Val Ser Lys Arg Pro Ser Gly Ile Ser Asn Arg Phe
     50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Cys Ser Tyr Ala Gly Asn
             85                  90                  95

Ser Ile Trp Val Phe Gly Gly Gly Thr Lys Leu Thr Val Leu
            100                 105                 110
```

<210> SEQ ID NO 25
<211> LENGTH: 354
<212> TYPE: DNA
<213> ORGANISM: Homo sapiens

<400> SEQUENCE: 25
caggttcagc tggtgcagtc tggagctgag gtgaagaagc ctggggcctc agtgaaggtc      60
tcctgcaagg cttctgctta cacctttacc agctatggta tcaactgggt gcgacaggcc     120
cctggacaag gacttgagtg gatgggatgg atcagcggtt acagtggtaa cacaaactac     180
gcacagaagc tccaggacag agtcaccatg accgcagaca catccacgag cacagcctac     240
atggagctga ggagcctgag atctgacgac acggccgtat attactgtgc gagagatggg     300
ccgaggggct actttgacta ctggggccag ggaaccctgg tcaccgtctc ctca           354

<210> SEQ ID NO 26
<211> LENGTH: 118
<212> TYPE: PRT
<213> ORGANISM: Homo sapiens

<400> SEQUENCE: 26

Gln Val Gln Leu Val Gln Ser Gly Ala Glu Val Lys Lys Pro Gly Ala
 1               5                  10                  15

Ser Val Lys Val Ser Cys Lys Ala Ser Ala Tyr Thr Phe Thr Ser Tyr
            20                  25                  30

Gly Ile Asn Trp Val Arg Gln Ala Pro Gly Gln Gly Leu Glu Trp Met
        35                  40                  45

Gly Trp Ile Ser Gly Tyr Ser Gly Asn Thr Asn Tyr Ala Gln Lys Leu
    50                  55                  60

Gln Asp Arg Val Thr Met Thr Ala Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Gly Pro Arg Gly Tyr Phe Asp Tyr Trp Gly Gln Gly Thr
            100                 105                 110

Leu Val Thr Val Ser Ser
        115

<210> SEQ ID NO 27
<211> LENGTH: 318
<212> TYPE: DNA
<213> ORGANISM: Homo sapiens

<400> SEQUENCE: 27
tcctatgagc tgactcagcc accctcagtg tccgtgtccc caggacagac agccagcatc      60
acctgctctg gagataaatt gggggataaa tatgcttgct ggtatcagca gaagccaggc     120
cagtcccctg tgctggtcat ctatcaagat agcaagcggc cctcagggat ccctgagcga     180
ttctctggct ccaactctgg gaacacagcc actctgacca tcagcgggac ccaggctatg     240
gatgaggctg actattactg tcaggcgtgg gacagcagca ctgtggtatt cggcggaggg     300
accaagctga ccgtccta                                                   318

<210> SEQ ID NO 28
<211> LENGTH: 106
<212> TYPE: PRT
<213> ORGANISM: Homo sapiens

<400> SEQUENCE: 28

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Val Val
                85                  90                  95

Phe Gly Gly Gly Thr Lys Leu Thr Val Leu
            100                 105

<210> SEQ ID NO 29
<211> LENGTH: 354
<212> TYPE: DNA
<213> ORGANISM: Homo sapiens

<400> SEQUENCE: 29
caggttcagc tggtgcagtc tggagctgag gtgaagaagc ctggggcctc agtgaaggtc      60
tcctgcaagg cttctggtta caccttaacc agctatggta tcagttgggt gcgacaggcc     120
cctggacaag ggcttgagtg gatgggatgg atcagcgctt acagtggtaa acaaactat     180 gaacagaagc tccagggcag agtcaccatg accacagaca catccacgag tgtagtctac     240
atggaactga ggagcctgag atctgacgac acggccgtat attactgtgc gagagatggg     300 ccgagggct actttgactt ctggggccag ggaaccctgg tcaccgtctc ctca            354

<210> SEQ ID NO 30
<211> LENGTH: 118
<212> TYPE: PRT
<213> ORGANISM: Homo sapiens

<400> SEQUENCE: 30

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Ser Gly Lys Thr Asn Tyr Glu Gln Lys Leu
    50                  55                  60

Gln Gly Arg Val Thr Met Thr Thr Asp Thr Ser Thr Ser Val Val Tyr
65                  70                  75                  80

Met Glu Leu Arg Ser Leu Arg Ser Asp Asp Thr Ala Val Tyr Tyr Cys
                85                  90                  95

Ala Arg Asp Gly Pro Arg Gly Tyr Phe Asp Phe Trp Gly Gln Gly Thr
            100                 105                 110

Leu Val Thr Val Ser Ser
            115

<210> SEQ ID NO 31
<211> LENGTH: 318
<212> TYPE: DNA
<213> ORGANISM: Homo sapiens

<400> SEQUENCE: 31

| | | | | | |
|---|---|---|---|---|---|
| tcctatgagc | tgactcagcc | accctcagtg | tccgtgtccc | caggacagac | agccagcatc | 60 |
| acctgctctg | gagataaatt | ggggataaa | tatgcttgct | ggtatcagca | gaagccaggc | 120 |
| cagtcccctg | tgctggtcat | ctatcaagat | agcaagcggc | cctcagggat | ccctgagcga | 180 |
| ttctctggct | ccaactctgg | gaacacagcc | actctgacca | tcagcgggac | ccaggctatg | 240 |
| gatgaggctg | actattactg | tcaggcgtgg | gacagcagca | ctgtggtttt | cggcggaggg | 300 |
| accaagctga | ccgtccta | | | | | 318 |

<210> SEQ ID NO 32
<211> LENGTH: 106
<212> TYPE: PRT
<213> ORGANISM: Homo sapiens

<400> SEQUENCE: 32

Ser Tyr Glu Leu Thr Gln Pro Pro Ser Val Ser Val Ser Pro Gly Gln
 1               5                  10                  15
Thr Ala Ser Ile Thr Cys Ser Gly Asp Lys Leu Gly Asp Lys Tyr Ala
            20                  25                  30
Cys Trp Tyr Gln Gln Lys Pro Gly Gln Ser Pro Val Leu Val Ile Tyr
        35                  40                  45
Gln Asp Ser Lys Arg Pro Ser Gly Ile Pro Glu Arg Phe Ser Gly Ser
    50                  55                  60
Asn Ser Gly Asn Thr Ala Thr Leu Thr Ile Ser Gly Thr Gln Ala Met
65                  70                  75                  80
Asp Glu Ala Asp Tyr Tyr Cys Gln Ala Trp Asp Ser Ser Thr Val Val
                85                  90                  95
Phe Gly Gly Gly Thr Lys Leu Thr Val Leu
            100                 105

<210> SEQ ID NO 33
<211> LENGTH: 360
<212> TYPE: DNA
<213> ORGANISM: Homo sapiens

<400> SEQUENCE: 33

| | | | | | |
|---|---|---|---|---|---|
| caggtgcagc | tgcaggagtc | gggcccagga | ctggtgaagc | cttcggagac | cctgtccctc | 60 |
| acctgcactg | tctctggtgg | ctccgtcagc | agtggtggtt | actactggag | ctggatccgg | 120 |
| cagcccccag | ggaagggact | ggagtggatt | ggatatttct | attacagtgg | gagccccaac | 180 |
| tacaacccct | ccctcaagag | gcgaatcgcc | atatcagtag | acacgtccaa | gaaccagttc | 240 |
| tccctgaggc | tgagctctgt | gaccgctgcg | gacacggccg | tgtattactg | tgcgagagat | 300 |
| cctatgcact | actacggtat | ggacgtctgg | ggccaaggga | ccacggtcac | cgtctcctca | 360 |

<210> SEQ ID NO 34
<211> LENGTH: 120
<212> TYPE: PRT
<213> ORGANISM: Homo sapiens

<400> SEQUENCE: 34

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Gly Tyr Tyr Trp Ser Trp Ile Arg Gln Pro Pro Gly Lys Gly Leu Glu
        35                  40                  45

Trp Ile Gly Tyr Phe Tyr Tyr Ser Gly Ser Pro Asn Tyr Asn Pro Ser
    50                  55                  60

Leu Lys Arg Arg Ile Ala Ile Ser Val Asp Thr Ser Lys Asn Gln Phe
65                  70                  75                  80

Ser Leu Arg Leu Ser Ser Val Thr Ala Ala Asp Thr Ala Val Tyr Tyr
                85                  90                  95

Cys Ala Arg Asp Pro Met His Tyr Tyr Gly Met Asp Val Trp Gly Gln
            100                 105                 110

Gly Thr Thr Val Thr Val Ser Ser
        115                 120

<210> SEQ ID NO 35
<211> LENGTH: 321
<212> TYPE: DNA
<213> ORGANISM: Homo sapiens

<400> SEQUENCE: 35
tcctctgagc tgactcagcc accctcagtg tccgtgttcc caggacagac agccaacatc     60
acctgctctg gagataaatt gggggataaa tttgcttgct ggtatcagca gaagccaggc    120
cagtcccctg tgctggtcat ctatcgagat aacaagcggc cctcaggat ccctgagcga    180 ttctctggct ccaactctgg gaacacagcc actctgacca tcagcgggac ccaggctatg    240
gatgaggctg actattactg tcaggcgtgg gacagcagca cttatgtggt tttcggcgga    300
gggaccaagc tgaccgtcct a                                              321

<210> SEQ ID NO 36
<211> LENGTH: 107
<212> TYPE: PRT
<213> ORGANISM: Homo sapiens

<400> SEQUENCE: 36

Ser Ser Glu Leu Thr Gln Pro Pro Ser Val Ser Val Phe Pro Gly Gln
1               5                   10                  15

Thr Ala Asn Ile Thr Cys Ser Gly Asp Lys Leu Gly Asp Lys Phe Ala
            20                  25                  30

Cys Trp Tyr Gln Gln Lys Pro Gly Gln Ser Pro Val Leu Val Ile Tyr
        35                  40                  45

Arg Asp Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Tyr Val
                85                  90                  95

Val Phe Gly Gly Gly Thr Lys Leu Thr Val Leu
            100                 105

<210> SEQ ID NO 37
<211> LENGTH: 362
<212> TYPE: DNA
<213> ORGANISM: Homo sapiens

<400> SEQUENCE: 37

```
caggtgcagc tgcaggagtc gggcccagga ctggtgaagc cttcggagac cctgtccctc      60
acctgcactg tctctggtgg ctccatcagt agtgactact ggagctggat ccggcagccc     120
gccgggaagg gactggagtg gattggccgt ttctataata gtggggagga caactacaga     180
ccctccctca agagtcgaat caccatgtca gtagacacgt ccaagaacca gttctccctg     240
aagctgagct ctgtgaccgc cgcggacacg gccgtgtatt actgtgccag agacatgtat     300
agcggcagag gaaactggta cttcgatctc tggggccgtg cacccctggt cactgtctcc     360
tc                                                                    362
```

<210> SEQ ID NO 38
<211> LENGTH: 120
<212> TYPE: PRT
<213> ORGANISM: Homo sapiens

<400> SEQUENCE: 38

```
Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Asp
            20                  25                  30

Tyr Trp Ser Trp Ile Arg Gln Pro Ala Gly Lys Gly Leu Glu Trp Ile
        35                  40                  45

Gly Arg Phe Tyr Asn Ser Gly Arg Thr Asn Tyr Arg Pro Ser Leu Lys
    50                  55                  60

Ser Arg Ile Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Met Tyr Ser Gly Arg Gly Asn Trp Tyr Phe Asp Leu Trp Gly
            100                 105                 110

Arg Gly Thr Leu Val Thr Val Ser
        115                 120
```

<210> SEQ ID NO 39
<211> LENGTH: 324
<212> TYPE: DNA
<213> ORGANISM: Homo sapiens

<400> SEQUENCE: 39

```
tcctatgagc tgacacagcc accctcggtg tcagtgtccc caggacaaac ggccaggatc      60
acctgctctg gagatgcatt gccaaaaaaa tatgcttatt ggtaccagca gaagtcaggc     120
caggcccctg tgctggtcat ctatgaggac agcaaacgac cctccgggat ccctgagaga     180
ttctctggct ccagctcagg gacaatggcc accttgacta tcagtggggc ccaggtggag     240
gatgaagctg actactactg ttactcaaca gacagcagtg ataatcatag ggtattcggc     300
ggagggacca agctgaccgt ccta                                            324
```

<210> SEQ ID NO 40
<211> LENGTH: 108
<212> TYPE: PRT
<213> ORGANISM: Homo sapiens

<400> SEQUENCE: 40

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Lys Tyr Ala
            20                  25                  30

Tyr Trp Tyr Gln Gln Lys Ser Gly Gln Ala Pro Val Leu Val Ile Tyr
        35                  40                  45

Glu Asp Ser Lys Arg Pro Ser Gly Ile Pro Glu Arg Phe Ser Gly Ser
    50                  55                  60

Ser Ser Gly Thr Met Ala Thr Leu Thr Ile Ser Gly Ala Gln Val Glu
65                  70                  75                  80

Asp Glu Ala Asp Tyr Tyr Cys Tyr Ser Thr Asp Ser Ser Asp Asn His
                85                  90                  95

Arg Val Phe Gly Gly Gly Thr Lys Leu Thr Val Leu
            100                 105

<210> SEQ ID NO 41
<211> LENGTH: 357
<212> TYPE: DNA
<213> ORGANISM: Homo sapiens

<400> SEQUENCE: 41
caggtgcagc tggtggagtc tgggggaggc gtggtccagc ctgggaggtc cctgagactc      60
tcctgtgcag cgtctggatt caccttcagt atctatggca ttcactgggt ccgccaggct     120
ccaggcaagg ggctggagtg ggtggcagtt atatggtatg atggaagtaa tgaatactat     180
gcagactccg tgaagggccg attcaccatc tccagagaca attccaagaa cacgctgtat     240
ctgcaaatga acagcctgag agccgaggac acggctgtgt attactgtgc gagagagaag     300
agcagtggct ggtactttga ctactggggc cagggaaccc tggtcaccgt ctcctca       357

<210> SEQ ID NO 42
<211> LENGTH: 119
<212> TYPE: PRT
<213> ORGANISM: Homo sapiens

<400> SEQUENCE: 42

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ile Tyr
            20                  25                  30

Gly Ile His Trp Val Arg Gln Ala Pro Gly Lys Gly Leu Glu Trp Val
        35                  40                  45

Ala Val Ile Trp Tyr Asp Gly Ser Asn Glu Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Lys Ser Ser Gly Trp Tyr Phe Asp Tyr Trp Gly Gln Gly
            100                 105                 110

Thr Leu Val Thr Val Ser Ser
            115

<210> SEQ ID NO 43
<211> LENGTH: 324
<212> TYPE: DNA
<213> ORGANISM: Homo sapiens

<400> SEQUENCE: 43

```
gaaattgtgt tgacgcagtc tccaggcacc ctgtctttgt ctccagggga aagagccacc      60
ctctcctgca gggccagtca gagtattagc agcagctgct tagcctgtta ccagcagaaa     120
cctggccaga ctcccaggct cctcatctat ggtgcatcca gctgggccac tggcatccca     180
gacaggttca gtggcagtcg gtctgggaca gacttcactc tctccatcag cagactggag     240
cctgacgatt ttgcagtgtg ttactgtcag cagtatggta gttcaccccc gacgttcggc     300
caagggacca aggtggaaat caaa                                             324
```

<210> SEQ ID NO 44
<211> LENGTH: 108
<212> TYPE: PRT
<213> ORGANISM: Homo sapiens

<400> SEQUENCE: 44

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ser Ser Ser
            20                  25                  30

Cys Leu Ala Cys Tyr Gln Gln Lys Pro Gly Gln Thr Pro Arg Leu Leu
        35                  40                  45

Ile Tyr Gly Ala Ser Ser Trp Ala Thr Gly Ile Pro Asp Arg Phe Ser
    50                  55                  60

Gly Ser Arg Ser Gly Thr Asp Phe Thr Leu Ser Ile Ser Arg Leu Glu
65                  70                  75                  80

Pro Asp Asp Phe Ala Val Cys Tyr Cys Gln Gln Tyr Gly Ser Ser Pro
                85                  90                  95

Pro Thr Phe Gly Gln Gly Thr Lys Val Glu Ile Lys
            100                 105

<210> SEQ ID NO 45
<211> LENGTH: 360
<212> TYPE: DNA
<213> ORGANISM: Homo sapiens

<400> SEQUENCE: 45

```
caggtgcagc tgcaggagtc gggcccagga ctggtgaagc cttcggagac cctgtccctc      60
acctgcactg tctctggtgg ctccgtcagc agtggtggtt actactggag ctgggtccgg     120
cagcccccag ggaagggact ggagtggatt gggtgtatct attttagtga gagcaccaac     180
tacaacccct ccctcaagag tcgagtcacc atatcagtag acacgtccaa gaaccagttc     240
tccctgaagc tgagctctgt gaccgctgcg gacacggccg tgtattactg tgcgagagat     300
cctatgcact actacggtat ggacgtctgg ggccaaggga ccacggtcac cgtctcctca     360
```

<210> SEQ ID NO 46
<211> LENGTH: 120
<212> TYPE: PRT
<213> ORGANISM: Homo sapiens

```
<400> SEQUENCE: 46

Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Val Ser Ser Gly
             20                  25                  30

Gly Tyr Tyr Trp Ser Trp Val Arg Gln Pro Pro Gly Lys Gly Leu Glu
         35                  40                  45

Trp Ile Gly Cys Ile Tyr Phe Ser Glu Ser Thr Asn Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Asp Pro Met His Tyr Tyr Gly Met Asp Val Trp Gly Gln
                100                 105                 110

Gly Thr Thr Val Thr Val Ser Ser
        115                 120

<210> SEQ ID NO 47
<211> LENGTH: 321
<212> TYPE: DNA
<213> ORGANISM: Homo sapiens

<400> SEQUENCE: 47
tcctttgaac tgactcagcc accctcagtg tcgtgtccc caggacagac agccagcatc      60
acctgctctg gagataaatt gggggataaa tttgcttgct ggtatcagca gaagccaggc    120
cagtcccctg tgctggtcat ctatcaagat accaagcggc cctcaggat ccctgagcga     180 atctctggct ccaactctgg gaacacagcc actctgacca tcagcgggac ccaggctatg    240
gatgaggctg actattactg tcaggcgtgg gacagtagca cttatgtggt tttcggcgga    300
gggaccaagc tgaccgtcct a                                              321

<210> SEQ ID NO 48
<211> LENGTH: 107
<212> TYPE: PRT
<213> ORGANISM: Homo sapiens

<400> SEQUENCE: 48

Ser Phe Glu Leu Thr Gln Pro Pro Ser Val Ser Val Ser Pro Gly Gln
  1               5                  10                  15

Thr Ala Ser Ile Thr Cys Ser Gly Asp Lys Leu Gly Asp Lys Phe Ala
             20                  25                  30

Cys Trp Tyr Gln Gln Lys Pro Gly Gln Ser Pro Val Leu Val Ile Tyr
         35                  40                  45

Gln Asp Thr Lys Arg Pro Ser Gly Ile Pro Glu Arg Ile Ser Gly Ser
 50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Gln Ala Trp Asp Ser Ser Thr Tyr Val
                 85                  90                  95

Val Phe Gly Gly Gly Thr Lys Leu Thr Val Leu
                100                 105
```

<210> SEQ ID NO 49
<211> LENGTH: 357
<212> TYPE: DNA
<213> ORGANISM: Homo sapiens

<400> SEQUENCE: 49

```
caggtgcagc tggtggagtc tgggggaggc gtggtccagc ctggaggtc cctgagactc      60 tcctgtgcag cgtctggatt caccttcagt gtttatggca tgcactgggt ccgccaggct     120
ccaggcaagg ggctggagtg ggtggcagtt atatggtatg atggaaataa taaatactat    180
gtagactccg tgaagggccg attcaccatc tccagagaca attccaagaa cacgctgtat    240
ctgcaactga acagcctgag agccgaggac acggctgtgt attactgtgc gagagagaga   300
agcagcagct ggtactttga ctactggggc cagggaaccc tggtcaccgt ctcctca      357
```

<210> SEQ ID NO 50
<211> LENGTH: 119
<212> TYPE: PRT
<213> ORGANISM: Homo sapiens

<400> SEQUENCE: 50

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Val Tyr
             20                  25                  30

Gly Met His Trp Val Arg Gln Ala Pro Gly Lys Gly Leu Glu Trp Val
         35                  40                  45

Ala Val Ile Trp Tyr Asp Gly Asn Asn Lys Tyr Tyr Val Asp Ser Val
     50                  55                  60

Lys Gly Arg Phe Thr Ile Ser Arg Asp Asn Ser Lys Asn Thr Leu Tyr
 65                  70                  75                  80

Leu Gln Leu Asn Ser Leu Arg Ala Glu Asp Thr Ala Val Tyr Tyr Cys
                 85                  90                  95

Ala Arg Glu Arg Ser Ser Ser Trp Tyr Phe Asp Tyr Trp Gly Gln Gly
            100                 105                 110

Thr Leu Val Thr Val Ser Ser
        115
```

<210> SEQ ID NO 51
<211> LENGTH: 330
<212> TYPE: DNA
<213> ORGANISM: Homo sapiens

<400> SEQUENCE: 51

```
cagtctgccc tgactcagcc tgcctccgtg tctgggtctt ctggacagtc gatcaccatc      60
tcctgcactg gaaccagcag tgatgttggg agttataacc ttgtctcctg gtaccaacag    120
cacccaggca aagcccccaa actcatgatt tatgaggtca gtaagcggcc ctcagggggtt   180 tctaatcgct tctctggctc caagtctggc aacacggcct ccctgacaat ctctgggctc   240
caggctgagg acgaggctga ttattactgc tgctcatatg caggtaatag caactgggtg    300
ttcggcggag ggaccaaact gaccgtccta                                      330
```

<210> SEQ ID NO 52
<211> LENGTH: 110
<212> TYPE: PRT
<213> ORGANISM: Homo sapiens

```
<400> SEQUENCE: 52

Gln Ser Ala Leu Thr Gln Pro Ala Ser Val Ser Gly Ser Gly Gln
  1               5                  10                  15

Ser Ile Thr Ile Ser Cys Thr Gly Thr Ser Ser Asp Val Gly Ser Tyr
             20                  25                  30

Asn Leu Val Ser Trp Tyr Gln Gln His Pro Gly Lys Ala Pro Lys Leu
             35                  40                  45

Met Ile Tyr Glu Val Ser Lys Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Cys Ser Tyr Ala Gly Asn
                 85                  90                  95

Ser Asn Trp Val Phe Gly Gly Gly Thr Lys Leu Thr Val Leu
            100                 105                 110

<210> SEQ ID NO 53
<211> LENGTH: 362
<212> TYPE: DNA
<213> ORGANISM: Homo sapiens

<400> SEQUENCE: 53
caggtgcagc tggtggagtc tgggggaggc gtggtccagc ctggggaggtc cctgagactc    60 tcctgtgcag cgtctggatt caccttcaat aactatggca tgcactgggt ccgccaggct   120
ccaggcaagg ggctggagtg cgtggcagtt atatggtatg atggaggtaa taaatattat   180
gcagactccg tgaagggccg attcgccatc tccagagaca attccaagaa cacgctgtat   240
ctgcaaatga acagcctgag agccgaggac acggctgtgt attactgtac tgcggtgact   300
aaactcaact actactacgg tatggacgtc tggggccaac ggaccacggt caccgtctcc   360
tc                                                                  362

<210> SEQ ID NO 54
<211> LENGTH: 120
<212> TYPE: PRT
<213> ORGANISM: Homo sapiens

<400> SEQUENCE: 54

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Asn Asn Tyr
             20                  25                  30

Gly Met His Trp Val Arg Gln Ala Pro Gly Lys Gly Leu Glu Cys Val
             35                  40                  45

Ala Val Ile Trp Tyr Asp Gly Gly Asn Lys Tyr Tyr Ala Asp Ser Val
 50                  55                  60

Lys Gly Arg Phe Ala Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Thr Ala Val Thr Lys Leu Asn Tyr Tyr Tyr Gly Met Asp Val Trp Gly
            100                 105                 110

Gln Arg Thr Thr Val Thr Val Ser
            115                 120
```

<210> SEQ ID NO 55
<211> LENGTH: 330
<212> TYPE: DNA
<213> ORGANISM: Homo sapiens

<400> SEQUENCE: 55

```
cagtctgccc tgactcagcc tgcctccgtg tctgggtctc ctggacagtc gatcaccatc     60
tcctgcactg gaaccagcag tgacgttggt ggttataact atgtctcctg gtaccaacag    120
cacccaggca aagcccccaa attcatgatt tatgaggtca gtaatcggcc ctcaggggtt    180
tctaatcgct tctctggctc caagtctggc aacacggcct ccctgaccat ctctgggctc    240
caggctgagg acgaggctga ttattactgc agctcatata caagcagcag tattctggta    300
ttcggcggag ggaccaagct gaccgtccta                                     330
```

<210> SEQ ID NO 56
<211> LENGTH: 110
<212> TYPE: PRT
<213> ORGANISM: Homo sapiens

<400> SEQUENCE: 56

```
Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Phe
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Ile Leu Val Phe Gly Gly Gly Thr Lys Leu Thr Val Leu
            100                 105                 110
```

<210> SEQ ID NO 57
<211> LENGTH: 362
<212> TYPE: DNA
<213> ORGANISM: Homo sapiens

<400> SEQUENCE: 57

```
caggtgcagc tggtggagtc tgggggaggc gtggtccagc ctgggaggtc cctgagactc     60
tcctgtgcag cgtctggatt caccttcaat aactatggca tgcactgggt ccgccaggct    120
ccaggcaagg gctggagtg cgtggcagtt atatggtatg atggaggtaa taaatactat    180
gcagactccg tgaagggccg attcgccatc tccagagaca attccaagaa cacgctgtat    240
ctgcaaatga acagcctgag agccgaggac acggctgtgt attactgtac tgcggtgacg    300
aaacttaact actactacgg tatggacgtc tggggccaag ggaccacggt caccgtctcc    360
tc                                                                    362
```

<210> SEQ ID NO 58
<211> LENGTH: 120
<212> TYPE: PRT
<213> ORGANISM: Homo sapiens

<400> SEQUENCE: 58

```
Gln Val Gln Leu Val Glu Ser Gly Gly Val Val Gln Pro Gly Arg
  1               5                  10                  15

Ser Leu Arg Leu Ser Cys Ala Ala Ser Gly Phe Thr Phe Asn Asn Tyr
             20                  25                  30

Gly Met His Trp Val Arg Gln Ala Pro Gly Lys Gly Leu Glu Cys Val
         35                  40                  45

Ala Val Ile Trp Tyr Asp Gly Asn Lys Tyr Tyr Ala Asp Ser Val
     50                  55                  60

Lys Gly Arg Phe Ala Ile Ser Arg Asp Asn Lys Asn Thr Leu Tyr
 65                  70                  75                  80

Leu Gln Met Asn Ser Leu Arg Ala Glu Asp Thr Ala Val Tyr Tyr Cys
                 85                  90                  95

Thr Ala Val Thr Lys Leu Asn Tyr Tyr Tyr Gly Met Asp Val Trp Gly
                100                 105                 110

Gln Gly Thr Thr Val Thr Val Ser
            115                 120
```

<210> SEQ ID NO 59
<211> LENGTH: 330
<212> TYPE: DNA
<213> ORGANISM: Homo sapiens

<400> SEQUENCE: 59

```
cagtctgccc tgactcagcc tgcctccgtg tctgggtctc ctggacagtc gatcaccatc      60
tcctgcactg gaaccagcag tgacgttggt ggttataact atgtctcctg gtaccaacag     120
cacccaggca aagcccccaa actcatgatt tatgaggtca gtaatcggcc ctcaggggtt     180
tctaatcgct tctctggctc caagtctggc aacacggcct ccctgaccat ctctgggctc     240
caggctgagg acgaggctga ttattactgc agctcatata caagcagcag tattctggtt     300
ttcggcggag ggaccaagct gaccgtccta                                      330
```

<210> SEQ ID NO 60
<211> LENGTH: 110
<212> TYPE: PRT
<213> ORGANISM: Homo sapiens

<400> SEQUENCE: 60

```
Gln Ser Ala Leu Thr Gln Pro Ala Ser Val Ser Gly Ser Pro Gly Gln
  1               5                  10                  15

Ser Ile Thr Ile Ser Cys Thr Gly Thr Ser Ser Asp Val Gly Gly Tyr
             20                  25                  30

Asn Tyr Val Ser Trp Tyr Gln Gln His Pro Gly Lys Ala Pro Lys Leu
         35                  40                  45

Met Ile Tyr Glu Val Ser Asn Arg Pro Ser Gly Val Ser Asn Arg Phe
     50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                 85                  90                  95

Ser Ile Leu Val Phe Gly Gly Gly Thr Lys Leu Thr Val Leu
                100                 105                 110
```

<210> SEQ ID NO 61
<211> LENGTH: 362
<212> TYPE: DNA
<213> ORGANISM: Homo sapiens

<400> SEQUENCE: 61

```
caggtgcagc tggtggagtc tgggggaggc gtggtccagc ctggaggtc cctgagactc      60
tcctgtgcag cgtctggatt caccttcaat aactatggca tgcactgggt ccgccaggct    120
ccaggcaagg ggctggagtg cgtggcagtt atatggtatg atggaggtaa taaatactat    180
gcagactccg tgaagggccg attcgccatc tccagagaca attccaagaa cacgttgtat    240
ctgcaaatga acagcctgag agccgaggac acggctgtgt attactgtac tgcggtgact    300
accctctact actactacgg tatggacgtc tggggccaag ggaccacggt caccgtctcc    360
tc                                                                    362
```

<210> SEQ ID NO 62
<211> LENGTH: 120
<212> TYPE: PRT
<213> ORGANISM: Homo sapiens

<400> SEQUENCE: 62

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Asn Asn Tyr
            20                  25                  30

Gly Met His Trp Val Arg Gln Ala Pro Gly Lys Gly Leu Glu Cys Val
        35                  40                  45

Ala Val Ile Trp Tyr Asp Gly Gly Asn Lys Tyr Tyr Ala Asp Ser Val
    50                  55                  60

Lys Gly Arg Phe Ala Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Ala Val Thr Thr Leu Tyr Tyr Tyr Tyr Gly Met Asp Val Trp Gly
            100                 105                 110

Gln Gly Thr Thr Val Thr Val Ser
        115                 120

<210> SEQ ID NO 63
<211> LENGTH: 330
<212> TYPE: DNA
<213> ORGANISM: Homo sapiens

<400> SEQUENCE: 63

```
cagtctgccc tgactcagcc tgcctccgtg tctgggtctc ctggacagtc gatcaccatc      60
tcctgcactg gaaccagcag tgacgttggt ggttataact atgtctcctg gtaccaacag    120
cacccaggca aagcccccaa actcatgatt tatgaggtca gtaatcggcc ctcaggggtt    180
tctaatcgct tctctggctc caagtctggc aacacggcct ccctgaccat ctctgggctc    240
caggctgagg acgaggctga ttattactgc agctcatata caagcagcag tattctggta    300
ttcggcggag ggaccaagct gaccgtcctg                                     330
```

<210> SEQ ID NO 64
<211> LENGTH: 110
<212> TYPE: PRT
<213> ORGANISM: Homo sapiens

```
<400> SEQUENCE: 64

Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Ile Leu Val Phe Gly Gly Gly Thr Lys Leu Thr Val Leu
            100                 105                 110

<210> SEQ ID NO 65
<211> LENGTH: 365
<212> TYPE: DNA
<213> ORGANISM: Homo sapiens

<400> SEQUENCE: 65
caggtgcagc tggtggagtc tgggggaggc ttggtcaagc ctggagggtc cctgagactc      60
tcctgtgcag cctctggatt caccttcagt gactactaca tgagctggat ccgccaggct    120
ccagggaagg ggctggagtg ggtttcatac attagaagta gtggtagtac catatactac    180
gcagactctg tgaagggccg attcaccatc tccagggaca acgccaagaa ctcactgtat    240
ctgcaaatga acagcctgag agccgaggac acggccgtgt attactgtgc gaggaccccg    300
tatagtggga ggtaccactg gtacttcgat ctctggggcc gtggcaccct ggtcactgtc    360
tcctc                                                                365

<210> SEQ ID NO 66
<211> LENGTH: 121
<212> TYPE: PRT
<213> ORGANISM: Homo sapiens

<400> SEQUENCE: 66

Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Arg Ser Ser Gly Ser Thr Ile Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Thr Pro Tyr Ser Gly Arg Tyr His Trp Tyr Phe Asp Leu Trp
            100                 105                 110

Gly Arg Gly Thr Leu Val Thr Val Ser
        115                 120
```

<210> SEQ ID NO 67
<211> LENGTH: 324
<212> TYPE: DNA
<213> ORGANISM: Homo sapiens

<400> SEQUENCE: 67

```
tcctatgagc tgacacagcc accctcggtg tcagtgtccc caggacaaac ggccaggatc      60
acctgctctg gagatgcatt gccaataaaa tatgcttatt ggtaccagca taagtcaggc     120
caggcccctg tgctggtcat ctatgaggac agcaaacgac cctccgggat ccctgagaga     180
ttctctggct ccagctcagg gacaatggcc accttgacta tcagtggggc ccaggtggag     240
gatgaagctg actactactg ttactcaaca gacagcagtg gtaatcatag ggtgttcggc     300
ggagggacca agctgaccgt ccta                                            324
```

<210> SEQ ID NO 68
<211> LENGTH: 108
<212> TYPE: PRT
<213> ORGANISM: Homo sapiens

<400> SEQUENCE: 68

Ser Tyr Glu Leu Thr Gln Pro Pro Ser Val Ser Val Ser Pro Gly Gln
1               5                  10                  15

Thr Ala Arg Ile Thr Cys Ser Gly Asp Ala Leu Pro Ile Lys Tyr Ala
            20                  25                  30

Tyr Trp Tyr Gln His Lys Ser Gly Gln Ala Pro Val Leu Val Ile Tyr
        35                  40                  45

Glu Asp Ser Lys Arg Pro Ser Gly Ile Pro Glu Arg Phe Ser Gly Ser
    50                  55                  60

Ser Ser Gly Thr Met Ala Thr Leu Thr Ile Ser Gly Ala Gln Val Glu
65                  70                  75                  80

Asp Glu Ala Asp Tyr Tyr Cys Tyr Ser Thr Asp Ser Ser Gly Asn His
                85                  90                  95

Arg Val Phe Gly Gly Gly Thr Lys Leu Thr Val Leu
            100                 105

<210> SEQ ID NO 69
<211> LENGTH: 377
<212> TYPE: DNA
<213> ORGANISM: Homo sapiens

<400> SEQUENCE: 69

```
caggtgcagc tggtggagtc tgggggaggc gtggtccagc ctggggaggtc cctgagactc      60 tcctgtgcag cgtctggatt caccttcagt agctttggca tgcactgggt ccgccaggct     120
ccaggcaagg ggctggagtg gtggcagtt atatggtatg atggaagtaa taaatattat     180
gcagactccg tgaagggccg attcaccatc tccagagaca attccaagaa cacgctgtat     240
ctgcaaatga acagcctgag agccgaggac acggctgtgt attactgtgc gagagaccca     300
aattacgata ttttgactgg ttactactac tacggcatgg acgtctgggg ccaagggacc     360
acggtcaccg tctcctc                                                    377
```

<210> SEQ ID NO 70
<211> LENGTH: 125
<212> TYPE: PRT
<213> ORGANISM: Homo sapiens

<400> SEQUENCE: 70

```
Gln Val Gln Leu Val Glu Ser Gly Gly Val Val Gln Pro Gly Arg
  1               5                  10                  15

Ser Leu Arg Leu Ser Cys Ala Ala Ser Gly Phe Thr Phe Ser Ser Phe
                 20                  25                  30

Gly Met His Trp Val Arg Gln Ala Pro Gly Lys Gly Leu Glu Trp Val
             35                  40                  45

Ala Val Ile Trp Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Pro Asn Tyr Asp Ile Leu Thr Gly Tyr Tyr Tyr Tyr Gly
                100                 105                 110

Met Asp Val Trp Gly Gln Gly Thr Thr Val Thr Val Ser
            115                 120                 125
```

<210> SEQ ID NO 71
<211> LENGTH: 324
<212> TYPE: DNA
<213> ORGANISM: Homo sapiens

<400> SEQUENCE: 71

```
tcttctgagc tgactcagga ccctgctgtg tctgtggcct tgggacagac agtcaggatc    60
acatgccaag agacatcct cagaacctat tatgcaagct ggtaccagca gaagccagga   120
caggcccctg tacttgtcat ctatggtaaa aacgaccggc cctcagggat cccagaccga   180
ttctctggct ccagctcagg aaacacagct tccttgacca tcactggggc tcaggcggaa   240
gatgaggctg actattactg tgactcccgg gacaacactg ttacccatct ggtattcggc   300
ggagggacca agctgaccgt ccta                                           324
```

<210> SEQ ID NO 72
<211> LENGTH: 108
<212> TYPE: PRT
<213> ORGANISM: Homo sapiens

<400> SEQUENCE: 72

```
Ser Ser Glu Leu Thr Gln Asp Pro Ala Val Ser Val Ala Leu Gly Gln
  1               5                  10                  15

Thr Val Arg Ile Thr Cys Gln Gly Asp Ile Leu Arg Thr Tyr Tyr Ala
                 20                  25                  30

Ser Trp Tyr Gln Gln Lys Pro Gly Gln Ala Pro Val Leu Val Ile Tyr
             35                  40                  45

Gly Lys Asn Asp Arg Pro Ser Gly Ile Pro Asp Arg Phe Ser Gly Ser
         50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys Asp Ser Arg Asp Asn Thr Val Thr His
                 85                  90                  95

Leu Val Phe Gly Gly Gly Thr Lys Leu Thr Val Leu
                100                 105
```

<210> SEQ ID NO 73
<211> LENGTH: 383
<212> TYPE: DNA
<213> ORGANISM: Homo sapiens

<400> SEQUENCE: 73

```
gaggtgcagc tggtggagtc tgggggaggc ttggtaaagc cagggcggtc cctgagactc      60
tcctgtacag gttctggatt cacctttggt gattatgctt tgaactggtt ccgccaggct     120
ccagggatgg ggctggagtg ggtaggtttc attagaggca aagcttatgg tgggacaaca     180
gaatacgccg cgtctgtgaa aggcagattc accatctcaa gagatgattc caaaagcatc     240
gcctatctgc aaatgaacag cctgaaaacc gaggacacag ccgtgtatta ctgtaataga     300
gaggtagagt attgcaggtc gtccgagaac tactgctacg gtatggacgt ctggggccaa     360
gggaccacgg tcaccgtctc ctc                                             383
```

<210> SEQ ID NO 74
<211> LENGTH: 127
<212> TYPE: PRT
<213> ORGANISM: Homo sapiens

<400> SEQUENCE: 74

Glu Val Gln Leu Val Glu Ser Gly Gly Gly Leu Val Lys Pro Gly Arg
1               5                   10                  15

Ser Leu Arg Leu Ser Cys Thr Gly Ser Gly Phe Thr Phe Gly Asp Tyr
            20                  25                  30

Ala Leu Asn Trp Phe Arg Gln Ala Pro Gly Met Gly Leu Glu Trp Val
        35                  40                  45

Gly Phe Ile Arg Gly Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Asn Arg Glu Val Glu Tyr Cys Arg Ser Ser Glu Asn Tyr Cys
            100                 105                 110

Tyr Gly Met Asp Val Trp Gly Gln Gly Thr Thr Val Thr Val Ser
        115                 120                 125

<210> SEQ ID NO 75
<211> LENGTH: 318
<212> TYPE: DNA
<213> ORGANISM: Homo sapiens

<400> SEQUENCE: 75

```
tcctatgagt tgactcagcc accctcagtg tccgtgtccc caggacagac agccagcatc      60
acctgctctg gagataaaat tggggataaa tttgcttgct ggtatcagca gaagccaggc     120
cagtcccctg tgctggtcat ctatcaagat accaagcggc cctcagggat ccctgagcga     180
ttctctggct ccaactctgg gaacacagcc actctgacca tcagcgggac ccaggctatg     240
gatgaggctg actattactg tcaggcgtgg gacagcaaca ctgtggtatt cggcggaggg     300
accaagctga ccgtccta                                                   318
```

<210> SEQ ID NO 76
<211> LENGTH: 106
<212> TYPE: PRT
<213> ORGANISM: Homo sapiens

<400> SEQUENCE: 76

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Phe Ala
            20                  25                  30

Cys Trp Tyr Gln Gln Lys Pro Gly Gln Ser Pro Val Leu Val Ile Tyr
        35                  40                  45

Gln Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Asn Thr Val Val
                85                  90                  95

Phe Gly Gly Gly Thr Lys Leu Thr Val Leu
            100                 105

<210> SEQ ID NO 77
<211> LENGTH: 153
<212> TYPE: PRT
<213> ORGANISM: Homo sapiens

<400> SEQUENCE: 77

Ala Pro Val Arg Ser Leu Asn Cys Thr Leu Arg Asp Ser Gln Gln Lys
1               5                   10                  15

Ser Leu Val Met Ser Gly Pro Tyr Glu Leu Lys Ala Leu His Leu Gln
            20                  25                  30

Gly Gln Asp Met Glu Gln Gln Val Val Phe Ser Met Ser Phe Val Gln
        35                  40                  45

Gly Glu Glu Ser Asn Asp Lys Ile Pro Val Ala Leu Gly Leu Lys Glu
    50                  55                  60

Lys Asn Leu Tyr Leu Ser Cys Val Leu Lys Asp Asp Lys Pro Thr Leu
65                  70                  75                  80

Gln Leu Glu Ser Val Asp Pro Lys Asn Tyr Pro Lys Lys Lys Met Glu
                85                  90                  95

Lys Arg Phe Val Phe Asn Lys Ile Glu Ile Asn Asn Lys Leu Glu Phe
            100                 105                 110

Glu Ser Ala Gln Phe Pro Asn Trp Tyr Ile Ser Thr Ser Gln Ala Glu
        115                 120                 125

Asn Met Pro Val Phe Leu Gly Gly Thr Lys Gly Gly Gln Asp Ile Thr
    130                 135                 140

Asp Phe Thr Met Gln Phe Val Ser Ser
145                 150

<210> SEQ ID NO 78
<211> LENGTH: 113
<212> TYPE: PRT
<213> ORGANISM: Homo sapiens

<400> SEQUENCE: 78

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

```
Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Tyr Phe Asp Tyr Trp Gly Gln Gly Thr Leu Val Thr Val Ser
                100                 105                 110

Ser
```

<210> SEQ ID NO 79
<211> LENGTH: 116
<212> TYPE: PRT
<213> ORGANISM: Homo sapiens

<400> SEQUENCE: 79

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
                20                  25                  30

Tyr Met Ser Trp Ile Arg Gln Ala Pro Gly Lys Gly Leu Glu Trp Val
            35                  40                  45

Ser Tyr Ile Ser Ser Ser Gly Ser Thr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Tyr Ser Gly Trp Tyr Phe Asp Leu Trp Gly Arg Gly Thr Leu Val
                100                 105                 110

Thr Val Ser Ser
            115
```

<210> SEQ ID NO 80
<211> LENGTH: 112
<212> TYPE: PRT
<213> ORGANISM: Homo sapiens

<400> SEQUENCE: 80

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Asp Tyr Trp Gly Gln Gly Thr Leu Val Thr Val Ser Ser
                100                 105                 110
```

<210> SEQ ID NO 81
<211> LENGTH: 114
<212> TYPE: PRT
<213> ORGANISM: Homo sapiens

<400> SEQUENCE: 81

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Tyr Tyr Tyr Gly Met Asp Val Trp Gly Gln Gly Thr Thr Val Thr Val
            100                 105                 110

Ser Ser

<210> SEQ ID NO 82
<211> LENGTH: 123
<212> TYPE: PRT
<213> ORGANISM: Homo sapiens

<400> SEQUENCE: 82

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asp Ile Leu Thr Gly Tyr Tyr Tyr Gly Met Asp Val
            100                 105                 110

Trp Gly Gln Gly Thr Thr Val Thr Val Ser Ser
        115                 120

<210> SEQ ID NO 83
<211> LENGTH: 116
<212> TYPE: PRT
<213> ORGANISM: Homo sapiens

<400> SEQUENCE: 83

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

```
Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Val Thr Tyr Tyr Tyr Gly Met Asp Val Trp Gly Gln Gly Thr Thr Val
            100                 105                 110

Thr Val Ser Ser
            115

<210> SEQ ID NO 84
<211> LENGTH: 117
<212> TYPE: PRT
<213> ORGANISM: Homo sapiens

<400> SEQUENCE: 84

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ser Ser Ser Trp Tyr Phe Asp Tyr Trp Gly Gln Gly Thr Leu
            100                 105                 110

Val Thr Val Ser Ser
            115

<210> SEQ ID NO 85
<211> LENGTH: 116
<212> TYPE: PRT
<213> ORGANISM: Homo sapiens

<400> SEQUENCE: 85

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ser Ser Gly Trp Phe Asp Tyr Trp Gly Gln Gly Thr Leu Val
            100                 105                 110

Thr Val Ser Ser
            115
```

```
<210> SEQ ID NO 86
<211> LENGTH: 124
<212> TYPE: PRT
<213> ORGANISM: Homo sapiens

<400> SEQUENCE: 86

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Thr Arg Glu Tyr Ser Ser Ser Tyr Tyr Tyr Gly Met Asp
            100                 105                 110

Val Trp Gly Gln Gly Thr Thr Val Thr Val Ser Ser
        115                 120

<210> SEQ ID NO 87
<211> LENGTH: 120
<212> TYPE: PRT
<213> ORGANISM: Homo sapiens

<400> SEQUENCE: 87

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Glu Tyr Ser Ser Ser Tyr Gly Met Asp Val Trp Gly Gln
            100                 105                 110

Gly Thr Thr Val Thr Val Ser Ser
        115                 120

<210> SEQ ID NO 88
<211> LENGTH: 116
<212> TYPE: PRT
<213> ORGANISM: Homo sapiens

<400> SEQUENCE: 88

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Ile
        35                  40                  45
```

```
Gly Arg Ile Tyr Thr Ser Gly Ser Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Tyr Ser Ser Trp Tyr Phe Asp Leu Trp Gly Arg Gly Thr Leu Val
                100                 105                 110

Thr Val Ser Ser
        115

<210> SEQ ID NO 89
<211> LENGTH: 116
<212> TYPE: PRT
<213> ORGANISM: Homo sapiens

<400> SEQUENCE: 89

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
                20                  25                  30

Gly Tyr Tyr Trp Ser Trp Ile Arg Gln Pro Pro Gly Lys Gly Leu Glu
            35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Tyr Tyr Gly Met Asp Val Trp Gly Gln Gly Thr Thr Val
                100                 105                 110

Thr Val Ser Ser
        115

<210> SEQ ID NO 90
<211> LENGTH: 125
<212> TYPE: PRT
<213> ORGANISM: Homo sapiens

<400> SEQUENCE: 90

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
                20                  25                  30

Ser Ala Ala Trp Asn Trp Ile Arg Gln Ser Pro Ser Arg Gly Leu Glu
            35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gln Gln Leu Val Tyr Tyr Tyr Tyr Gly Met
                100                 105                 110

Asp Val Trp Gly Gln Gly Thr Thr Val Thr Val Ser Ser
        115                 120                 125
```

-continued

<210> SEQ ID NO 91
<211> LENGTH: 111
<212> TYPE: PRT
<213> ORGANISM: Homo sapiens

<400> SEQUENCE: 91

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Ile Gln Leu Pro Thr Phe Gly Gln Gly Thr Arg Leu Glu Ile Lys
            100                 105                 110

<210> SEQ ID NO 92
<211> LENGTH: 107
<212> TYPE: PRT
<213> ORGANISM: Homo sapiens

<400> SEQUENCE: 92

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys His Gln Ser Ser Ser Leu Pro Phe
                85                  90                  95

Thr Phe Gly Pro Gly Thr Lys Val Asp Ile Lys
            100                 105

<210> SEQ ID NO 93
<211> LENGTH: 106
<212> TYPE: PRT
<213> ORGANISM: Homo sapiens

<400> SEQUENCE: 93

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

```
Pro Glu Asp Phe Ala Val Tyr Tyr Cys Gln Gln Tyr Gly Ser Ser Thr
                85                  90                  95

Phe Gly Gln Gly Thr Lys Val Glu Ile Lys
            100                 105

<210> SEQ ID NO 94
<211> LENGTH: 107
<212> TYPE: PRT
<213> ORGANISM: Homo sapiens

<400> SEQUENCE: 94

Gln Ser Ala Leu Thr Gln Pro Ala Ser Val Ser Gly Ser Pro Gly Gln
  1               5                  10                  15

Ser Ile Thr Ile Ser Cys Thr Gly Thr Ser Ser Asp Val Gly Gly Tyr
                 20                  25                  30

Asn Tyr Val Ser Trp Tyr Gln Gln His Pro Gly Lys Ala Pro Lys Leu
             35                  40                  45

Met Ile Tyr Glu Val Ser Asn Arg Pro Ser Gly Val Ser Asn Arg Phe
         50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                85                  90                  95

Val Phe Gly Gly Gly Thr Lys Leu Thr Val Leu
            100                 105

<210> SEQ ID NO 95
<211> LENGTH: 108
<212> TYPE: PRT
<213> ORGANISM: Homo sapiens

<400> SEQUENCE: 95

Gln Ser Ala Leu Thr Gln Pro Ala Ser Val Ser Gly Ser Pro Gly Gln
  1               5                  10                  15

Ser Ile Thr Ile Ser Cys Thr Gly Thr Ser Ser Asp Val Gly Ser Tyr
                 20                  25                  30

Asn Leu Val Ser Trp Tyr Gln Gln His Pro Gly Lys Ala Pro Lys Leu
             35                  40                  45

Met Ile Tyr Glu Gly Ser Lys Arg Pro Ser Gly Val Ser Asn Arg Phe
         50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Cys Ser Tyr Ala Gly Ser
                85                  90                  95

Ser Val Phe Gly Gly Gly Thr Lys Leu Thr Val Leu
            100                 105

<210> SEQ ID NO 96
<211> LENGTH: 110
<212> TYPE: PRT
<213> ORGANISM: Homo sapiens

<400> SEQUENCE: 96

Gln Ser Ala Leu Thr Gln Pro Ala Ser Val Ser Gly Ser Pro Gly Gln
  1               5                  10                  15

Ser Ile Thr Ile Ser Cys Thr Gly Thr Ser Ser Asp Val Gly Ser Tyr
                 20                  25                  30
```

Asn Leu Val Ser Trp Tyr Gln Gln His Pro Gly Lys Ala Pro Lys Leu
            35                  40                  45

Met Ile Tyr Glu Gly Ser Lys Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Cys Ser Tyr Ala Gly Ser
                 85                  90                  95

Ser Thr Trp Val Phe Gly Gly Gly Thr Lys Leu Thr Val Leu
                100                 105                 110

<210> SEQ ID NO 97
<211> LENGTH: 106
<212> TYPE: PRT
<213> ORGANISM: Homo sapiens

<400> SEQUENCE: 97

Ser Tyr Glu Leu Thr Gln Pro Pro Ser Val Ser Val Ser Pro Gly Gln
 1               5                  10                  15

Thr Ala Ser Ile Thr Cys Ser Gly Asp Lys Leu Gly Asp Lys Tyr Ala
             20                  25                  30

Cys Trp Tyr Gln Gln Lys Pro Gly Gln Ser Pro Val Leu Val Ile Tyr
         35                  40                  45

Gln Asp Ser Lys Arg Pro Ser Gly Ile Pro Glu Arg Phe Ser Gly Ser
     50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Gln Ala Trp Asp Ser Ser Thr Val Val
                 85                  90                  95

Phe Gly Gly Gly Thr Lys Leu Thr Val Leu
                100                 105

<210> SEQ ID NO 98
<211> LENGTH: 108
<212> TYPE: PRT
<213> ORGANISM: Homo sapiens

<400> SEQUENCE: 98

Ser Ser Glu Leu Thr Gln Asp Pro Ala Val Ser Val Ala Leu Gly Gln
 1               5                  10                  15

Thr Val Arg Ile Thr Cys Gln Gly Asp Ser Leu Arg Ser Tyr Tyr Ala
             20                  25                  30

Ser Trp Tyr Gln Gln Lys Pro Gly Gln Ala Pro Val Leu Val Ile Tyr
         35                  40                  45

Gly Lys Asn Asn Arg Pro Ser Gly Ile Pro Asp Arg Phe Ser Gly Ser
     50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys Asn Ser Arg Asp Ser Ser Gly Asn His
                 85                  90                  95

Leu Val Phe Gly Gly Gly Thr Lys Leu Thr Val Leu
                100                 105

<210> SEQ ID NO 99
<211> LENGTH: 108
<212> TYPE: PRT
<213> ORGANISM: Homo sapiens -continued

```
<400> SEQUENCE: 99

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Lys Tyr Ala
                20                  25                  30

Tyr Trp Tyr Gln Gln Lys Ser Gly Gln Ala Pro Val Leu Val Ile Tyr
            35                  40                  45

Glu Asp Ser Lys Arg Pro Ser Gly Ile Pro Glu Arg Phe Ser Gly Ser
        50                  55                  60

Ser Ser Gly Thr Met Ala Thr Leu Thr Ile Ser Gly Ala Gln Val Glu
65                  70                  75                  80

Asp Glu Ala Asp Tyr Tyr Cys Tyr Ser Thr Asp Ser Ser Gly Asn His
                85                  90                  95

Arg Val Phe Gly Gly Gly Thr Lys Leu Thr Val Leu
                100                 105

<210> SEQ ID NO 100
<211> LENGTH: 108
<212> TYPE: PRT
<213> ORGANISM: Homo sapiens

<400> SEQUENCE: 100

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Lys Tyr Ala
                20                  25                  30

Tyr Trp Tyr Gln Gln Lys Ser Gly Gln Ala Pro Val Leu Val Ile Tyr
            35                  40                  45

Glu Asp Ser Lys Arg Pro Ser Gly Ile Pro Glu Arg Phe Ser Gly Ser
        50                  55                  60

Ser Ser Gly Thr Met Ala Thr Leu Thr Ile Ser Gly Ala Gln Val Glu
65                  70                  75                  80

Asp Glu Ala Asp Tyr Tyr Cys Tyr Ser Thr Asp Ser Ser Gly Asn His
                85                  90                  95

Arg Val Phe Gly Gly Gly Thr Lys Leu Thr Val Leu
                100                 105
```